United States Patent
Beck et al.

(10) Patent No.: US 11,530,220 B2
(45) Date of Patent: Dec. 20, 2022

(54) SUBSTITUTED IMIDAZO[1,5-A]PYRAZINES AND [1,2,4]TRIAZOLO[4,3-A]PYRAZINES FOR THE MODULATION OF AHR

(71) Applicant: IDEAYA BIOSCIENCES, INC., South San Francisco, CA (US)

(72) Inventors: Hilary Plake Beck, South San Francisco, CA (US); Marcos Gonzalez-Lopez, South San Francisco, CA (US); James Clifford Sutton, Jr., South San Francisco, CA (US)

(73) Assignee: IDEAYA BIOSCIENCES, INC., South San Francisco, CA (US)

( * ) Notice: Subject to any disclaimer, the term of this patent is extended or adjusted under 35 U.S.C. 154(b) by 29 days.

(21) Appl. No.: 16/967,100

(22) PCT Filed: Feb. 5, 2019

(86) PCT No.: PCT/US2019/016711
§ 371 (c)(1),
(2) Date: Aug. 3, 2020

(87) PCT Pub. No.: WO2019/156989
PCT Pub. Date: Aug. 15, 2019

(65) Prior Publication Data
US 2021/0079001 A1    Mar. 18, 2021

Related U.S. Application Data

(60) Provisional application No. 62/626,849, filed on Feb. 6, 2018.

(51) Int. Cl.
*A61K 31/4985* (2006.01)
*C07D 487/04* (2006.01)
*A61K 45/06* (2006.01)

(52) U.S. Cl.
CPC ............ *C07D 487/04* (2013.01); *A61K 45/06* (2013.01)

(58) Field of Classification Search
CPC .................. A61K 31/4985; C07D 487/04
USPC .............................. 514/249; 544/350
See application file for complete search history.

(56) References Cited

FOREIGN PATENT DOCUMENTS

| WO | 2005035532 A1 | 4/2005 | |
|---|---|---|---|
| WO | 2010059401 A2 | 5/2010 | |
| WO | 2018191476 A1 | 10/2018 | |
| WO | 2018195397 A2 | 10/2018 | |
| WO | WO-2019156989 A1 * | 8/2019 | ............ A61P 35/00 |

OTHER PUBLICATIONS

Jordan, V. C. Nature Reviews: Drug Discovery, 2, 2003, 205.*
Dbrwald, F. Zaragoza. Side Reactions in Organic Synthesis: A Guide to Successful Synthesis Design, Weinheim: WILEY-VCH Verlag GmbH & Co. KGaA, 2005, Preface.*
Vippagunta, et al. Advanced Drug Delivery Reviews, 48, 2001, 18.*
International Search Report for PCT/US2019/016711, dated May 14, 2019, 5 pages.
Written Opinion of the International Searching Authority for PCT/US2019/016711, dated May 14, 2019, 8 pages.

* cited by examiner

*Primary Examiner* — Douglas M Willis
(74) *Attorney, Agent, or Firm* — Mintz, Levin, Cohn, Ferris, Glovsky & Popeo, P.C.

(57) ABSTRACT

Provided herein are compounds, compositions and methods of using the compounds and compositions for the treatment of diseases modulated, as least in part, by AhR. The compounds are represented by formula:

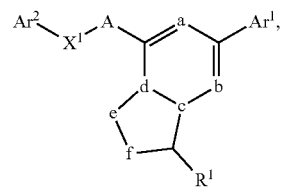

wherein the letters and symbols a, b, c, d, e, f, A, $R^1$, $X^1$, $Ar^1$ and $Ar^2$ have the meanings provided in the specification.

21 Claims, No Drawings

SUBSTITUTED IMIDAZO[1,5-A]PYRAZINES AND [1,2,4]TRIAZOLO[4,3-A]PYRAZINES FOR THE MODULATION OF AHR

CROSS-REFERENCES TO RELATED APPLICATIONS

This application is the U.S. National Stage Entry under § 371 of International Application No. PCT/US2019/016711, filed Feb. 5, 2019, which claims the benefit of priority to U.S. Provisional Application Ser. No. 62/626,849 filed Feb. 6, 2018, each of which is incorporated herein in its entirety by reference.

STATEMENT AS TO RIGHTS TO INVENTIONS MADE UNDER FEDERALLY SPONSORED RESEARCH AND DEVELOPMENT

NOT APPLICABLE

REFERENCE TO A "SEQUENCE LISTING," A TABLE, OR A COMPUTER PROGRAM LISTING APPENDIX SUBMITTED ON A COMPACT DISK

NOT APPLICABLE

BACKGROUND OF THE INVENTION

The aryl hydrocarbon receptor (AhR) is a helix-loop-helix ligand-activated transcription factor that mediates biological responses to aromatic hydrocarbons. AhR is localized in the cytoplasm, where upon binding to a hydrocarbon based ligand agonist such as 2,3,7,8-tetrachlorodibenzo-p-dioxin (TCDD), it migrates to the nucleus and forms a heterodimer with aryl hydrocarbon receptor nuclear translocator (ARNT). Formation of the AhR/ARNT complexes subsequently enables binding to and transcription of the xenobiotic response element (XRE) and associated genes. AhR can also activate a non-XRE dependent protein-protein interaction pathway.

Through its XRE-dependent and independent activity, AhR modulates numerous critical innate and adaptive immune responses. Chief among those responses, AhR agonists promote development of IL-17 producing T-helper cells (Th17) and regulatory T-cells (Tregs). AhR activation further induces trans-differentiation of Th17 cells to Tregs and enhances the suppressive activity of Tregs. Studies have also demonstrated that AhR agonism results in suppression of innate inflammatory responses mediated by macrophages (e.g. Reduced LPS-induced IL-lb, IL-6, IL-12 and TNFa expression) and dendritic cells (DCs) (inhibits activation of DCs and promotes expression of IL-10).

To mount an effective anti-tumor immune response, antigen presenting cells (APCs) are required to process, present and consequently activate helper CD4+ T-cells (Th) and cytotoxic CD8+ T-cells (Tc) which act in concert to effectively lyse tumor cells. Tumor cells have developed several mechanisms to evade the immune mediated lysis of Th and Tc. One such mechanism is the release of high concentrations of kynurenine and other potential AhR ligands in the tumor microenvironment (TME). High AhR ligand concentrations activate the AhR in the TME resulting in suppression of APCs, Th and Tc directly, as well as recruitment, generation and activation of Tregs and Th17 which further suppress the activity of Th and Tc. Through this mechanism, tumor cells are capable of evading anti-tumor immune responses. An antagonist of the AhR pathway would therefore block the AhR-dependent immune evasion mechanisms employed by malignant cells and restore effective anti-tumor immunity.

Recent insights into tumor immunobiology has revealed that malignant cells employ a composite of immune-evasion mechanisms. Blocking or enhancing these mechanisms through a combination of therapeutic applications such as immune check point inhibition and vaccines has been demonstrated pre-clinically and clinically to provide an optimal restoration of the anti-tumor immune response. While it is expected that AhR antagonism in monotherapy will restore anti-tumor immunity, a combination of an AhR modulator with a check point inhibitor and/or vaccine is predicted to work in concert with other therapeutics to potentiate the immunotherapeutic response.

Immune mechanisms regulated by AhR have also been associated with autoimmune and inflammatory diseases such as multiple sclerosis and inflammatory bowel diseases. The activation of AhR by agonists could therefore be beneficial for the therapeutic treatment of autoimmune and inflammatory diseases. While agonists of AhR are described in the art, there remains a need for improved compositions and methods for immunological modulation of treating autoimmune and inflammatory diseases via modulation of AhR.

BRIEF SUMMARY OF THE INVENTION

Provided herein are compounds, compositions and methods of using the compounds and compositions for the treatment of diseases modulated, as least in part, by AhR. The compounds are represented by formula:

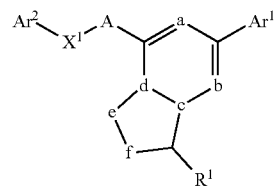

wherein the letters and symbols a, b, c, d, e, f, $R^1$, A, $X^1$, $Ar^1$ and $Ar^2$ have the meanings provided below.

BRIEF DESCRIPTION OF THE DRAWINGS

Not Applicable

DETAILED DESCRIPTION OF THE INVENTION

Before the present invention is further described, it is to be understood that the invention is not limited to the particular embodiments set forth herein, and it is also to be understood that the terminology used herein is for the purpose of describing particular embodiments only, and is not intended to be limiting.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention. Unless defined otherwise, all technical and scientific terms used herein have the same meaning as commonly understood by one of ordinary skill in the art to which this invention belongs.

It must be noted that as used herein and in the appended claims, the singular forms "a," "an," and "the" include plural referents unless the context clearly dictates otherwise. It further noted that the claims may be drafted to exclude any optional element. As such, this statement is intended to serve as antecedent basis for use of such exclusive terminology such as "solely," "only" and the like in connection with the recitation of claim elements, or use of a "negative" limitation.

The publications discussed herein are provided solely for their disclosure prior to the filing date of the present application. Further, the dates of publication provided may be different from the actual publication dates, which may need to be independently confirmed.

General

The present invention is drawn to, inter alia, small molecule compounds having AhR modulator activity, as well as compositions thereof, and methods of using the compounds and compositions for the treatment and prevention of the diseases, disorders and conditions described herein.

Definitions

Unless otherwise indicated, the following terms are intended to have the meaning set forth below. Other terms are defined elsewhere throughout the specification.

The term "alkyl", by itself or as part of another substituent, means, unless otherwise stated, a saturated straight or branched chain hydrocarbon radical, having the number of carbon atoms designated (i.e. $C_{1-8}$ means one to eight carbons). Examples of alkyl groups include methyl, ethyl, n-propyl, isopropyl, n-butyl, t-butyl, isobutyl, sec-butyl, n-pentyl, n-hexyl, n-heptyl, n-octyl, and the like.

The term "deuteroalkyl", by itself or as part of another substituent, refers to an alkyl group wherein from one to five hydrogen atoms have been replaced by deuterium. An example of a "deuteroalkyl" group is —CD$_3$.

The term "alkylene" refers to a divalent alkyl group as defined herein. Examples of alkylene include methylene, ethylene, and the like.

The term "cycloalkyl" refers to hydrocarbon rings having the indicated number of ring atoms (e.g., $C_{3-6}$ cycloalkyl) and being fully saturated or having no more than one double bond between ring vertices. "Cycloalkyl" is also meant to refer to bicyclic and polycyclic hydrocarbon rings such as, for example, bicyclo[2.2.1]heptane, bicyclo[2.2.2]octane, etc.

The term "heterocycloalkyl" refers to a ring having from three to eight carbon ring vertices in which one or more carbon ring vertices are replaced by a ring vertex is selected from N, O, and S, and wherein the nitrogen and sulfur atoms are optionally oxidized, and the nitrogen atom(s) are optionally quaternized. The heterocycloalkyl may be a monocyclic, a bicyclic or a polycylic ring system. Non limiting examples of heterocycloalkyl groups include pyrrolidine, imidazolidine, pyrazolidine, butyrolactam, valerolactam, imidazolidinone, hydantoin, dioxolane, phthalimide, piperidine, 1,4-dioxane, morpholine, thiomorpholine, thiomorpholine-S-oxide, thiomorpholine-S,S-oxide, piperazine, pyran, pyridone, 3-pyrroline, thiopyran, pyrone, tetrahydrofuran, tetrahydrothiophene, quinuclidine, and the like. A heterocycloalkyl group can be attached to the remainder of the molecule through a ring carbon or a heteroatom.

As used herein, a wavy line, "⌇", that intersects a single, double or triple bond in any chemical structure depicted herein, represent the point attachment of the single, double, or triple bond to the remainder of the molecule. Additionally, a bond extending to the center of a ring (e.g., a phenyl ring) is meant to indicate attachment at any of the available ring vertices. One of skill in the art will understand that multiple substituents shown as being attached to a ring will occupy ring vertices that provide stable compounds and are otherwise sterically compatible. For a divalent component, a representation is meant to include either orientation (forward or reverse). For example, the group "—C(O)NH—" is meant to include a linkage in either orientation: —C(O)NH— or —NHC(O)—, and similarly, "—O—CH$_2$CH$_2$—" is meant to include both —O—CH$_2$CH$_2$— and —CH$_2$CH$_2$—O—.

The terms "alkoxy," "alkylamino" and "alkylthio" (or thioalkoxy) are used in their conventional sense, and refer to those alkyl groups attached to the remainder of the molecule via an oxygen atom, an amino group, or a sulfur atom, respectively. Additionally, for dialkylamino groups, the alkyl portions can be the same or different and can also be combined to form a 3-7 membered ring with the nitrogen atom to which each is attached. Accordingly, a group represented as dialkylamino or —NR$^a$R$^b$ is meant to include piperidinyl, pyrrolidinyl, morpholinyl, azetidinyl and the like.

The terms "halo" or "halogen," by themselves or as part of another substituent, mean, unless otherwise stated, a fluorine, chlorine, bromine, or iodine atom. Additionally, terms such as "haloalkyl," are meant to include monohaloalkyl and polyhaloalkyl. For example, the term "$C_{1-4}$ haloalkyl" is meant to include trifluoromethyl, 2,2,2-trifluoroethyl, 4-chlorobutyl, 3-bromopropyl, and the like.

The term "aryl" means, unless otherwise stated, a polyunsaturated, typically aromatic, hydrocarbon group which can be a single ring or multiple rings (up to three rings) which are fused together or linked covalently. Non-limiting examples of aryl groups include phenyl, naphthyl and biphenyl.

The term "heteroaryl" refers to a 5- to 10-membered aromatic ring or fused ring system that contains from one to five heteroatoms selected from N, O, and S, wherein the nitrogen and sulfur atoms are optionally oxidized, and the nitrogen atom(s) are optionally quaternized. A heteroaryl group can be attached to the remainder of the molecule through a heteroatom. Non-limiting examples of heteroaryl groups include pyridyl, pyridazinyl, pyrazinyl, pyrimindinyl, triazinyl, quinolinyl, quinoxalinyl, quinazolinyl, cinnolinyl, phthalazinyl, benzotriazinyl, purinyl, benzimidazolyl, benzopyrazolyl, benzotriazolyl, benzisoxazolyl, isobenzofuryl, isoindolyl, indolizinyl, benzotriazinyl, thienopyridinyl, thienopyrimidinyl, pyrazolopyrimidinyl, imidazopyridines, benzothiaxolyl, benzofuranyl, benzothienyl, indolyl, quinolyl, isoquinolyl, isothiazolyl, pyrazolyl, indazolyl, pteridinyl, imidazolyl, triazolyl, tetrazolyl, oxazolyl, isoxazolyl, thiadiazolyl, pyrrolyl, thiazolyl, furyl, thienyl and the like.

As used herein, the term "heteroatom" is meant to include oxygen (O), nitrogen (N), sulfur (S) and silicon (Si).

The term "pharmaceutically acceptable salts" is meant to include salts of the active compounds which are prepared with relatively nontoxic acids or bases, depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of salts derived from pharmaceutically-acceptable inorganic bases include aluminum, ammonium, calcium, copper, ferric, ferrous, lithium, magnesium, manganic, manganous, potassium, sodium, zinc and the like. Salts derived from pharmaceutically-acceptable organic bases include salts of primary, secondary and tertiary amines, including substituted amines, cyclic amines, naturally-occurring amines and the like, such as arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine and the like. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, malonic, benzoic, succinic, suberic, fumaric, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, for example, Berge, S. M., et al, "Pharmaceutical Salts", *Journal of Pharmaceutical Science*, 1977, 66, 1-19). Certain specific compounds of the present invention contain both basic and acidic functionalities that allow the compounds to be converted into either base or acid addition salts.

The neutral forms of the compounds may be regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the present invention.

In addition to salt forms, the present invention provides compounds which are in a prodrug form. Prodrugs of the compounds described herein are those compounds that readily undergo chemical changes under physiological conditions to provide the compounds of the present invention. Additionally, prodrugs can be converted to the compounds of the present invention by chemical or biochemical methods in an ex vivo environment. For example, prodrugs can be slowly converted to the compounds of the present invention when placed in a transdermal patch reservoir with a suitable enzyme or chemical reagent.

Certain compounds of the present invention can exist in unsolvated forms as well as solvated forms, including hydrated forms. In general, the solvated forms are equivalent to unsolvated forms and are intended to be encompassed within the scope of the present invention. Certain compounds of the present invention may exist in multiple crystalline or amorphous forms. In general, all physical forms are equivalent for the uses contemplated by the present invention and are intended to be within the scope of the present invention.

Certain compounds of the present invention possess asymmetric carbon atoms (optical centers) or double bonds; the racemates, diastereomers, geometric isomers, regioisomers and individual isomers (e.g., separate enantiomers) are all intended to be encompassed within the scope of the present invention. When a stereochemical depiction is shown, it is meant to refer the compound in which one of the isomers is present and substantially free of the other isomer. 'Substantially free of' another isomer indicates at least an 80/20 ratio of the two isomers, more preferably 90/10, or 95/5 or more. In some embodiments, one of the isomers will be present in an amount of at least 99%.

The compounds of the present invention may also contain unnatural proportions of atomic isotopes at one or more of the atoms that constitute such compounds. Unnatural proportions of an isotope may be defined as ranging from the amount found in nature to an amount consisting of 100% of the atom in question. For example, the compounds may incorporate radioactive isotopes, such as for example tritium ($^3$H), iodine-125 ($^{125}$I) or carbon-14 ($^{14}$C), or non-radioactive isotopes, such as deuterium ($^2$H) or carbon-13 ($^{13}$C). Such isotopic variations can provide additional utilities to those described elsewhere within this application. For instance, isotopic variants of the compounds of the invention may find additional utility, including but not limited to, as diagnostic and/or imaging reagents, or as cytotoxic/radiotoxic therapeutic agents. Additionally, isotopic variants of the compounds of the invention can have altered pharmacokinetic and pharmacodynamic characteristics which can contribute to enhanced safety, tolerability or efficacy during treatment. All isotopic variations of the compounds of the present invention, whether radioactive or not, are intended to be encompassed within the scope of the present invention.

The terms "patient" or "subject" are used interchangeably to refer to a human or a non-human animal (e.g., a mammal). In one embodiment, the patient is human.

The terms "administration", "administer" and the like, as they apply to, for example, a subject, cell, tissue, organ, or biological fluid, refer to contact of, for example, an AhR modulator, a pharmaceutical composition comprising same, or a diagnostic agent to the subject, cell, tissue, organ, or biological fluid. In the context of a cell, administration includes contact (e.g., in vitro or ex vivo) of a reagent to the cell, as well as contact of a reagent to a fluid, where the fluid is in contact with the cell.

The terms "treat", "treating", treatment" and the like refer to a course of action (such as administering an AhR modulator or a pharmaceutical composition comprising same) initiated after a disease, disorder or condition, or a symptom thereof, has been diagnosed, observed, and the like so as to eliminate, reduce, suppress, mitigate, or ameliorate, either temporarily or permanently, at least one of the underlying causes of a disease, disorder, or condition afflicting a subject, or at least one of the symptoms associated with a disease, disorder, condition afflicting a subject. Thus, treatment includes inhibiting (e.g., arresting the development or further development of the disease, disorder or condition or clinical symptoms association therewith) an active disease.

The term "in need of treatment" as used herein refers to a judgment made by a physician or other caregiver that a subject requires or will benefit from treatment. This judgment is made based on a variety of factors that are in the realm of the physician's or caregiver's expertise.

The terms "prevent", "preventing", "prevention" and the like refer to a course of action (such as administering an AhR modulator or a pharmaceutical composition comprising same) initiated in a manner (e.g., prior to the onset of a disease, disorder, condition or symptom thereof) so as to prevent, suppress, inhibit or reduce, either temporarily or permanently, a subject's risk of developing a disease, disorder, condition or the like (as determined by, for example, the absence of clinical symptoms) or delaying the onset thereof, generally in the context of a subject predisposed to having a particular disease, disorder or condition. In certain instances, the terms also refer to slowing the progression of the disease, disorder or condition or inhibiting progression thereof to a harmful or otherwise undesired state.

The term "in need of prevention" as used herein refers to a judgment made by a physician or other caregiver that a subject requires or will benefit from preventative care. This judgment is made based on a variety of factors that are in the realm of a physician's or caregiver's expertise.

The phrase "therapeutically effective amount" refers to the administration of an agent to a subject, either alone or as part of a pharmaceutical composition and either in a single dose or as part of a series of doses, in an amount capable of having any detectable, positive effect on any symptom, aspect, or characteristic of a disease, disorder or condition when administered to the subject. The therapeutically effective amount can be ascertained by measuring relevant physiological effects, and it can be adjusted in connection with the dosing regimen and diagnostic analysis of the subject's condition, and the like. By way of example, measurement of the serum level of an AhR modulator (or, e.g., a metabolite thereof) at a particular time post-administration may be indicative of whether a therapeutically effective amount has been used.

The phrase "in a sufficient amount to effect a change" means that there is a detectable difference between a level of an indicator measured before (e.g., a baseline level) and after administration of a particular therapy. Indicators include any objective parameter (e.g., serum concentration) or subjective parameter (e.g., a subject's feeling of well-being).

The terms "inhibitors" and "antagonists", or "activators" and "agonists" refer to inhibitory or activating molecules, respectively, for example, for the activation of, e.g., a ligand, receptor, cofactor, gene, cell, tissue, or organ. Inhibitors are molecules that decrease, block, prevent, delay activation, inactivate, desensitize, or down-regulate, e.g., a gene, protein, ligand, receptor, or cell. Activators are molecules that increase, activate, facilitate, enhance activation, sensitize, or up-regulate, e.g., a gene, protein, ligand, receptor, or cell. An inhibitor may also be defined as a molecule that reduces, blocks, or inactivates a constitutive activity. An "agonist" is a molecule that interacts with a target to cause or promote an increase in the activation of the target. An "antagonist" is a molecule that opposes the action(s) of an agonist. An antagonist prevents, reduces, inhibits, or neutralizes the activity of an agonist, and an antagonist can also prevent, inhibit, or reduce constitutive activity of a target, e.g., a target receptor, even where there is no identified agonist.

The terms "modulate", "modulation" and the like refer to the ability of a molecule (e.g., an activator or an inhibitor) to increase or decrease the function or activity of AhR, either directly or indirectly. A modulator may act alone, or it may use a cofactor, e.g., a protein, metal ion, or small molecule. Examples of modulators include small molecule compounds and other bioorganic molecules.

The "activity" of a molecule may describe or refer to the binding of the molecule to a ligand or to a receptor; to catalytic activity; to the ability to stimulate gene expression or cell signaling, differentiation, or maturation; to antigenic activity; to the modulation of activities of other molecules; and the like. The term "proliferative activity" encompasses an activity that promotes, that is necessary for, or that is specifically associated with, for example, normal cell division, as well as cancer, tumors, dysplasia, cell transformation, metastasis, and angiogenesis.

"Substantially pure" indicates that a component makes up greater than about 50% of the total content of the composition, and typically greater than about 60% of the total content. More typically, "substantially pure" refers to compositions in which at least 75%, at least 85%, at least 90% or more of the total composition is the component of interest. In some cases, the component of interest will make up greater than about 90%, or greater than about 95% of the total content of the composition.

AhR and Modulation Thereof

Identification of AhR Modulators Possessing Desirable Characteristics

The present invention is drawn, in part, to the identification of AhR modulators with at least one property or characteristic that is of therapeutic relevance. Candidate AhR modulators can be identified by using, for example, an art-accepted assay or model, examples of which are will be apparent to the skilled artisan. The assay used to determine the AhR modulatory activity of the compounds described herein is set forth in the Experimental section.

After identification, candidate modulators can be further evaluated by using techniques that provide data regarding characteristics of the modulators (e.g., pharmacokinetic parameters). Comparisons of the candidate modulators to a reference standard (which may the "best-of-class" of current modulators) are indicative of the potential viability of such candidates.

AhR modulators that can serve as reference or benchmark compounds include CH223191, StemRegenin-1, kynurenine, ITE, GNF351, and CB7993113. Other reference compounds subsequently identified by the skilled artisan can also be used to assess the viability of candidate AhR modulators.

Compounds

Provided herein are compound having the formula (I):

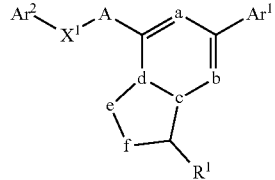

or a pharmaceutically acceptable salt, solvate or hydrate thereof, wherein;
  each of ring vertices a, b, c, d, e and f is independently selected from the group consisting of C, CH and N;
  the ring having vertices c, d, e and f has two double bonds
  only one of c and d is N;
  from one to three of a, b, e and f are N;
  $R^1$ is selected from the group consisting of $C_{1-6}$ alkyl, $C_{1-6}$ haloalkyl, $C_{1-6}$ hydroxyalkyl, $C_{3-7}$ cycloalkyl and $C_{3-7}$ heterocycloalkyl;
  A is NH or O;
  $X^1$ is $C_{1-6}$ alkylene;

Ar¹ is a 5- to 9-membered heteroaryl group having at least one nitrogen atom as a ring member, which is substituted with from 0 to 3 members independently selected from the group consisting of halogen, hydroxyl, deuterium, CN, $C_{1-4}$ alkyl, $C_{1-4}$ haloalkyl, $C_{1-4}$ deuteroalkyl, —$CO_2R^a$, —$CONR^aR^b$, —$C(O)R^a$, —$OC(O)R^a$, —$OC(O)NR^aR^b$, —$NR^bC(O)R^a$, —$NR^bC(O)_2R^c$, —$NR^aC(O)NR^aR^b$, —$NR^aR^b$, —$OR^a$, —$S(O)_{0-2}R^a$ and —$S(O)_2NR^aR^b$;

Ar² is selected from the group consisting of:
(i) phenyl, which is substituted with from 0 to 3 members independently selected from the group consisting of halogen, deuterium, $C_{1-4}$ alkyl, $C_{1-4}$ haloalkyl, $C_{1-4}$ deuteroalkyl, CN, —$CO_2R^a$, —$CONR^aR^b$, —$C(O)R^c$, —$OC(O)R^a$, —$OC(O)NR^aR^b$, —$NR^bC(O)R^a$, —$NR^bC(O)_2R^c$, —$NR^aC(O)NR^aR^b$, —$NR^aR^b$, —$OR^a$, —$S(O)_{0-2}R^a$ and —$S(O)_2NR^aR^b$; and
(ii) 5- to 9-membered heteroaryl, which is substituted with from 0 to 3 members independently selected from the group consisting of halogen, deuterium, $C_{1-4}$ alkyl, $C_{1-4}$ haloalkyl, $C_{1-4}$ deuteroalkyl, oxo, CN, —$CO_2R^a$, —$CONR^aR^b$, —$C(O)R^c$, —$OC(O)NR^aR^b$, —$NR^bC(O)R^a$, —$OC(O)R^a$, —$NR^bC(O)_2R^c$, —$NR^aC(O)NR^aR^b$, —$NR^aR^b$, —$OR^a$, —$S(O)_{0-2}R^a$ and —$S(O)_2NR^aR^b$;

wherein
each $R^a$ and $R^b$ is independently selected from the group consisting of hydrogen, $C_{1-4}$ alkyl, and $C_{1-4}$ haloalkyl, or when attached to the same nitrogen atom are optionally combined with the nitrogen atom to form a four-, five- or six-membered ring having from 0 to 2 additional heteroatoms as ring members selected from N, O, S, SO or $SO_2$, and each $R^c$ is independently selected from the group consisting of $C_{1-4}$ alkyl and $C_{1-4}$ haloalkyl.

In one group of embodiments, the compounds of formula (I) are those wherein Ar¹ is selected from the group consisting of pyridinyl, pyrimidinyl, pyrazinyl, pyridazinyl, pyrazolyl, imidazolyl, 1,2,3-triazolyl, 1,2,4-triazolyl and tetrazolyl, each of which is substituted with 0 to 3 members independently selected from the group consisting of halogen, hydroxyl, deuterium, CN, $C_{1-4}$ alkyl, $C_{1-4}$ haloalkyl, $C_{1-4}$ deuteroalkyl, —$CO_2R^a$, —$CONR^aR^b$, —$C(O)R^a$, —$OC(O)R^a$, —$OC(O)NR^aR^b$, —$NR^bC(O)R^a$, —$NR^bC(O)_2R^c$, —$NR^aC(O)NR^aR^b$, —$NR^aR^b$, —$OR^a$, —$S(O)_{0-2}R^a$ and —$S(O)_2NR^aR^b$. In further selected embodiments, the compounds of formula (I) are those wherein Ar¹ is selected from the group consisting of:

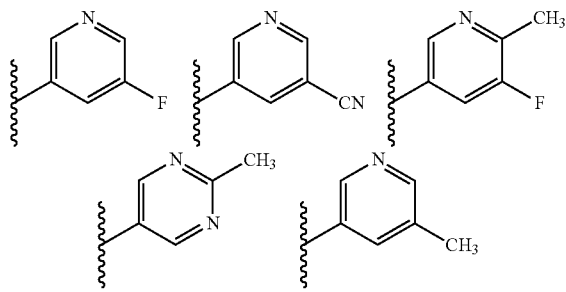

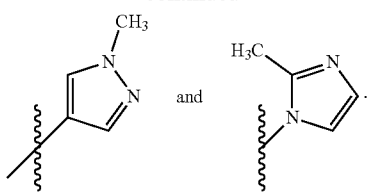

In another group of embodiments, the compounds of formula (I) are those wherein Ar² is phenyl, which is substituted with from 0 to 3 members independently selected from the group consisting of halogen, deuterium, $C_{1-4}$ alkyl, $C_{1-4}$ haloalkyl, $C_{1-4}$ deuteroalkyl, —$CO_2R^a$, —$CONR^aR^b$, —$C(O)R^c$, —$OC(O)R^a$, —$OC(O)NR^aR^b$, —$NR^bC(O)R^a$, —$NR^bC(O)_2R^c$, —$NR^aC(O)NR^aR^b$, —$NR^aR^b$, —$OR^a$, —$S(O)_{0-2}R^a$ and —$S(O)_2NR^aR^b$. In still further selected embodiments, Ar² is phenyl and is substituted with from 0 to 3 members independently selected from the group consisting of $C_{1-4}$ alkyl, —$CO_2R^a$, —$CONR^aR^b$, —$OC(O)R^a$, —$OC(O)NR^aR^b$, —$NR^bC(O)R^a$, —$NR^bC(O)_2R^c$, —$NR^aR^b$, and —$OR^a$. In still further selected embodiments, Ar² is phenyl and is substituted with 0 to 3 members independently selected from the group consisting of OH and $C(O)NH_2$.

In yet another group of embodiments, the compounds of formula (I) are those wherein Ar² is 5- to 9-membered heteroaryl, which is substituted with from 0 to 3 members independently selected from the group consisting of halogen, deuterium, $C_{1-4}$ alkyl, $C_{1-4}$ haloalkyl, $C_{1-4}$ deuteroalkyl, CN, —$CO_2R^a$, —$CONR^aR^b$, —$C(O)R^c$, —$OC(O)R^a$, —$OC(O)NR^aR^b$, —$NR^bC(O)R^a$, —$NR^bC(O)_2R^c$, —$NR^aC(O)NR^aR^b$, —$NR^aR^b$, —$OR^a$, —$S(O)_{0-2}R^a$ and —$S(O)_2NR^aR^b$. In some selected embodiments, Ar² is selected from the group consisting of benzopyrazolyl, benzimidazolyl, indolyl, pyrrolyl, 1H-pyrrolo[3,2-b]pyridinyl and 1H-pyrrolo[2,3-b]pyridinyl, each of which is substituted with from 0 to 3 members independently selected from the group consisting of halogen, deuterium, $C_{1-4}$ alkyl, $C_{1-4}$ haloalkyl, $C_{1-4}$ deuteroalkyl, oxo, —$CO_2R^a$, —$CONR^aR^b$, —$C(O)R^c$, —$OC(O)NR^aR^b$, —$NR^bC(O)R^a$, —$OC(O)R^a$, —$NR^bC(O)_2R^c$, —$NR^aC(O)NR^aR^b$, —$NR^aR^b$, —$OR^a$, —$S(O)_{0-2}R^a$ and —$S(O)_2NR^aR^b$. In still further selected embodiments, Ar² is selected from the group consisting of:

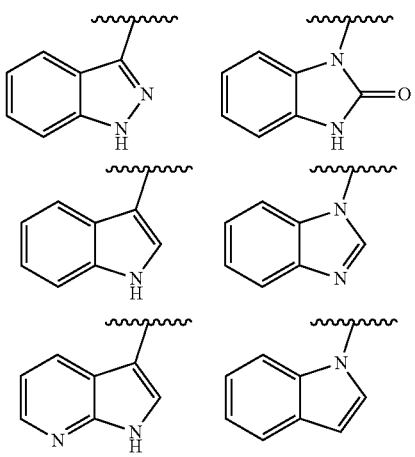

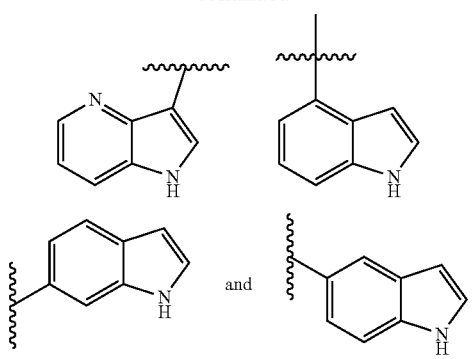

each of which is substituted with from 0 to 3 members independently selected from the group consisting of halogen, $C_{1-4}$ alkyl, $C_{1-4}$ haloalkyl, CN, —$CO_2R^a$, —$CONR^aR^b$, —$C(O)R^c$, —$OC(O)NR^aR^b$, and —$OR^a$.

In another group of embodiments, $Ar^2$ is pyrrole, which is substituted with from 0 to 3 members selected from the group consisting of halogen, $C_{1-4}$ alkyl, $C_{1-4}$ haloalkyl, CN, —$CO_2R^a$, —$CONR^aR^b$, —$C(O)R^c$, —$OC(O)NR^aR^b$, and —$OR^a$.

In still other embodiments, compounds of formula (I) and any of the embodiments described above, the compounds provided herein are represented by formulae Ia, Ib, Ic, Id, Ie, If, Ig, Ih, Ii and Ij:

Ia

Ib

Ic

Id

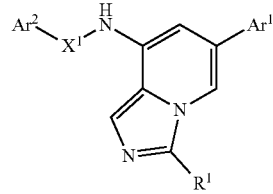

Ie

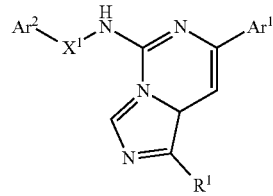

If

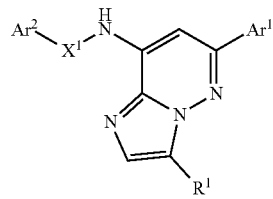

Ig

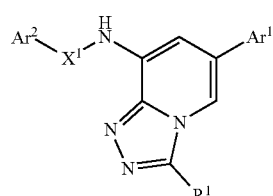

Ih

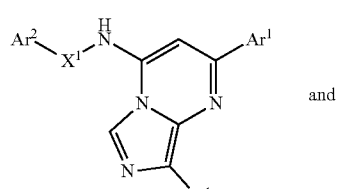

Ii and

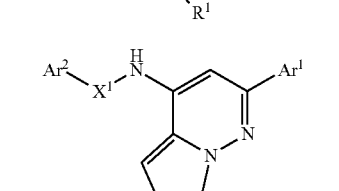

Ij

In further selected embodiments, compounds are represented by formulae Ib, Id, Ie, If, Ig, Ih, Ii and Ij. In some embodiments, compounds are represented by formula Ia. In some embodiments, compounds are represented by formula Ib. In some embodiments, compounds are represented by formula Ic. In some embodiments, compounds are represented by formula Id. In some embodiments, compounds are represented by formula Ie. In some embodiments, compounds are represented by formula If. In some embodiments, compounds are represented by formula Ig. In some embodiments, compounds are represented by formula Ih. In some embodiments, compounds are represented by formula Ii. In some embodiments, compounds are represented by formula Ij.

In some selected embodiments, compounds are provided having formula I (and any of the selected embodiments), as well as formulae Ia, Ib, Ic, Id, Ie, If, Ig, Ih, Ii and Ij (and any of the selected embodiments) wherein $R^1$ is isopropyl or 1-hydroxyprop-2-yl.

In some selected embodiments, compounds are provided having formula I (and any of the selected embodiments), as well as formulae Ia, Ib, Ic, Id, Ie, If, Ig, Ih, Ii and Ij (and any of the selected embodiments) wherein $R^1$ is isopropyl.

In some selected embodiments, compounds are provided having formula I (and any of the selected embodiments), as well as formulae Ia, Ib, Ic, Id, Ie, If, Ig, Ih, Ii and Ij (and any of the selected embodiments) wherein $X^1$ is —$CH_2$—.

In some selected embodiments, compounds are provided having formula I (and any of the selected embodiments), as well as formulae Ia, Ib, Ic, Id, Ie, If, Ig, Ih, Ii and Ij (and any of the selected embodiments) wherein $X^1$ is —$CH_2CH_2$—.

In some selected embodiments, compounds are provided having formula I (and any of the selected embodiments), as well as formulae Ia, Ib, Ic, Id, Ie, If, Ig, Ih, Ii and Ij (and any of the selected embodiments) wherein $X^1$ is —$CH(CH_3)CH_2$—.

In some selected embodiments, provided herein are compounds in Table 1 having +++ or ++++ activity.

Therapeutic and Prophylactic Uses

The present invention contemplates the use of the AhR modulators described herein in the treatment or prevention of a broad range of diseases, disorders and/or conditions, and/or the symptoms thereof. While particular uses are described in detail hereafter, it is to be understood that the present invention is not so limited. Furthermore, although general categories of particular diseases, disorders and conditions are set forth hereafter, some of the diseases, disorders and conditions may be a member of more than one category, and others may not be a member of any of the disclosed categories.

Oncology-related Disorders. In accordance with the present invention, an AhR modulator can be used to treat or prevent a proliferative condition or disorder, including a cancer, for example, cancer of the uterus, cervix, breast, prostate, testes, gastrointestinal tract (e.g., esophagus, oropharynx, stomach, small or large intestines, colon, or rectum), kidney, renal cell, bladder, bone, bone marrow, skin, head or neck, liver, gall bladder, heart, lung, pancreas, salivary gland, adrenal gland, thyroid, brain (e.g., gliomas), ganglia, central nervous system (CNS) and peripheral nervous system (PNS), and cancers of the hematopoietic system and the immune system (e.g., spleen or thymus). The present invention also provides methods of treating or preventing other cancer-related diseases, disorders or conditions, including, for example, immunogenic tumors, non-immunogenic tumors, dormant tumors, virus-induced cancers (e.g., epithelial cell cancers, endothelial cell cancers, squamous cell carcinomas and papillomavirus), adenocarcinomas, lymphomas, carcinomas, melanomas, leukemias, myelomas, sarcomas, teratocarcinomas, chemically-induced cancers, metastasis, and angiogenesis. The invention contemplates reducing tolerance to a tumor cell or cancer cell antigen, e.g., by modulating activity of a regulatory T-cell and/or a CD8+ T-cell (see, e.g., Ramirez-Montagut, et al. (2003) Oncogene 22:3180-87; and Sawaya, et al. (2003) New Engl. J. Med. 349:1501-09). In particular embodiments, the tumor or cancer is colon cancer, ovarian cancer, breast cancer, melanoma, lung cancer, glioblastoma, or leukemia. The use of the term(s) cancer-related diseases, disorders and conditions is meant to refer broadly to conditions that are associated, directly or indirectly, with cancer, and includes, e.g., angiogenesis and precancerous conditions such as dysplasia.

In certain embodiments, a cancer be metastatic or at risk of becoming metastatic, or may occur in a diffuse tissue, including cancers of the blood or bone marrow (e.g., leukemia). In some further embodiments, the compounds of the invention can be used to overcome T-cell tolerance.

In some embodiments, the present invention provides methods for treating a proliferative condition, cancer, tumor, or precancerous condition with an AhR modulator and at least one additional therapeutic or diagnostic agent, examples of which are set forth elsewhere herein.

Immune-related Disorders and Disorders with an Inflammatory Component. As used herein, terms such as "immune disease", "immune condition", "immune disorder", "inflammatory disease", "inflammatory condition", "inflammatory disorder" and the like are meant to broadly encompass any immune-related condition (e.g., an autoimmune disease) or a disorder with an inflammatory component that can be treated by the AhR modulators described herein such that some therapeutic benefit is obtained. Such conditions frequently are inextricably intertwined with other diseases, disorders and conditions. By way of example, an "immune condition" may refer to proliferative conditions, such as cancer, tumors, and angiogenesis; including infections (acute and chronic), tumors, and cancers that resist eradication by the immune system.

The AhR modulators provided herein can be used to increase or enhance an immune response; to improve immunization, including increasing vaccine efficacy; and to increase inflammation. Immune deficiencies associated with immune deficiency diseases, immunosuppressive medical treatment, acute and/or chronic infection, and aging can be treated using the compounds disclosed herein. The AhR modulators can also be used to stimulate the immune system of patients suffering from iatrogenically-induced immune suppression, including those who have undergone bone marrow transplants, chemotherapy, or radiotherapy.

In particular embodiments of the present disclosure, the AhR modulators are used to increase or enhance an immune response to an antigen by providing adjuvant activity. In a particular embodiment, at least one antigen or vaccine is administered to a subject in combination with at least one AhR modulator as provided herein to prolong an immune response to the antigen or vaccine. Therapeutic compositions are also provided which include at least one antigenic agent or vaccine component, including, but not limited to, viruses, bacteria, and fungi, or portions thereof, proteins, peptides, tumor-specific antigens, and nucleic acid vaccines, in combination with at least one AhR modulator as provided herein.

Microbial-related Disorders. By inhibiting the immunosuppressive and anti-inflammatory activity of AhR, the present disclosure contemplates the use of the AhR modulators described herein in the treatment and/or prevention of any viral, bacterial, fungal, parasitic or other infective disease, disorder or condition for which treatment with an AhR modulator may be beneficial. Examples of such diseases and disorders include HIV and AIDS, staphylococcal and streptococcal infections (e.g., *Staphylococcus aureus* and *Streptococcus sanguinis*, respectively), *leishmania, toxoplasma, trichomonas*, giardia, *Candida albicans, Bacillus anthracia*, and *Pseudomonas aeruginosa*. Compounds of the invention can be used to treat sepsis, decrease or inhibit bacterial growth, and reduce or inhibit inflammatory cytokines.

CNS-related and Neurological Disorders. Inhibition of AhR may also be an important treatment strategy for patients with neurological, neuropsychiatric, neurodegenerative or other diseases, disorders and conditions having some association with the central nervous system, including disorders associated with impairment of cognitive function and motor function. Examples include Parkinson's disease, extra pyramidal syndrome (EPS), dystonia, akathisia, tardive dyskinesia, restless leg syndrome (RLS), epilepsy, periodic limb movement in sleep (PLMS), attention deficit disorders, depression, anxiety, dementia, Alzheimer's disease, Huntington's disease, multiple sclerosis, cerebral ischemia, hemorrhagic stroke, subarachnoid hemorrhage, and traumatic brain injury.

Other Disorders. Embodiments provided herein also contemplate the administration of the AhR modulators described herein to a subject for the treatment or prevention of any other disorder that may benefit from at least some level of AhR modulation. Such diseases, disorders and conditions include, for example, cardiovascular (e.g., cardiac ischemia), gastrointestinal (e.g., Crohn's disease), metabolic (e.g., diabetes), hepatic (e.g., hepatic fibrosis, NASH, and NAFLD), pulmonary (e.g., COPD and asthma), ophthalmologic (e.g., diabetic retinopathy), and renal (e.g., renal failure) disorders.

In some embodiments, the AhR modulators provided herein may be used to inhibit statin-induced adenosine production, or reduce or decrease increases in blood glucose caused by a statin in a subject taking a statin (e.g., lovastatin and pravastatin)

Pharmaceutical Compositions

The AhR modulators provided herein may be in the form of compositions suitable for administration to a subject. In general, such compositions are "pharmaceutical compositions" comprising an AhR modulator(s) and one or more pharmaceutically acceptable or physiologically acceptable diluents, carriers or excipients. In certain embodiments, the AhR modulator is present in a therapeutically acceptable amount. The pharmaceutical compositions may be used in the methods of the present invention; thus, for example, the pharmaceutical compositions can be administered ex vivo or in vivo to a subject in order to practice the therapeutic and prophylactic methods and uses described herein.

The pharmaceutical compositions of the present invention can be formulated to be compatible with the intended method or route of administration; exemplary routes of administration are set forth herein. Furthermore, the pharmaceutical compositions may be used in combination with other therapeutically active agents or compounds as described herein in order to treat or prevent the diseases, disorders and conditions as contemplated by the present invention.

The pharmaceutical compositions containing the active ingredient (e.g., a modulator of AhR function) may be in a form suitable for oral use, for example, as tablets, capsules, troches, lozenges, aqueous or oily suspensions, dispersible powders or granules, emulsions, hard or soft capsules, or syrups, solutions, microbeads or elixirs. Pharmaceutical compositions intended for oral use may be prepared according to any method known to the art for the manufacture of pharmaceutical compositions, and such compositions may contain one or more agents such as, for example, sweetening agents, flavoring agents, coloring agents and preserving agents in order to provide pharmaceutically elegant and palatable preparations. Tablets, capsules and the like contain the active ingredient in admixture with non-toxic pharmaceutically acceptable excipients which are suitable for the manufacture of tablets. These excipients may be, for example, diluents, such as calcium carbonate, sodium carbonate, lactose, calcium phosphate or sodium phosphate; granulating and disintegrating agents, for example corn starch, or alginic acid; binding agents, for example starch, gelatin or acacia, and lubricating agents, for example magnesium stearate, stearic acid or talc.

The tablets, capsules and the like suitable for oral administration may be uncoated or coated by known techniques to delay disintegration and absorption in the gastrointestinal tract and thereby provide a sustained action. For example, a time-delay material such as glyceryl monostearate or glyceryl distearate may be employed. They may also be coated by techniques known in the art to form osmotic therapeutic tablets for controlled release. Additional agents include biodegradable or biocompatible particles or a polymeric substance such as polyesters, polyamine acids, hydrogel, polyvinyl pyrrolidone, polyanhydrides, polyglycolic acid, ethylene-vinylacetate, methylcellulose, carboxymethylcellulose, protamine sulfate, or lactide/glycolide copolymers, polylactide/glycolide copolymers, or ethylenevinylacetate copolymers in order to control delivery of an administered composition. For example, the oral agent can be entrapped in microcapsules prepared by coacervation techniques or by interfacial polymerization, by the use of hydroxymethylcellulose or gelatin-microcapsules or poly (methylmethacrolate) microcapsules, respectively, or in a colloid drug delivery system. Colloidal dispersion systems include macromolecule complexes, nano-capsules, microspheres, microbeads, and lipid-based systems, including oil-in-water emulsions, micelles, mixed micelles, and liposomes. Methods for the preparation of the above-mentioned formulations will be apparent to those skilled in the art.

Formulations for oral use may also be presented as hard gelatin capsules wherein the active ingredient is mixed with an inert solid diluent, for example, calcium carbonate, calcium phosphate, kaolin or microcrystalline cellulose, or as soft gelatin capsules wherein the active ingredient is mixed with water or an oil medium, for example peanut oil, liquid paraffin, or olive oil.

Aqueous suspensions contain the active materials in admixture with excipients suitable for the manufacture thereof. Such excipients can be suspending agents, for example sodium carboxymethylcellulose, methylcellulose, hydroxy-propylmethylcellulose, sodium alginate, polyvinylpyrrolidone, gum tragacanth and gum acacia; dispersing or wetting agents, for example a naturally-occurring phosphatide (e.g., lecithin), or condensation products of an alkylene oxide with fatty acids (e.g., polyoxy-ethylene stearate), or condensation products of ethylene oxide with long chain aliphatic alcohols (e.g., for heptadecaethyleneoxycetanol), or condensation products of ethylene oxide with partial esters derived from fatty acids and a hexitol (e.g., polyoxyethylene sorbitol monooleate), or condensation products of ethylene oxide with partial esters derived from fatty acids and hexitol anhydrides (e.g., polyethylene sorbitan monooleate). The aqueous suspensions may also contain one or more preservatives.

Oily suspensions may be formulated by suspending the active ingredient in a vegetable oil, for example *arachis* oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified herein.

The pharmaceutical compositions of the present invention may also be in the form of oil-in-water emulsions. The oily phase may be a vegetable oil, for example olive oil or *arachis* oil, or a mineral oil, for example, liquid paraffin, or mixtures of these. Suitable emulsifying agents may be naturally occurring gums, for example, gum acacia or gum tragacanth; naturally occurring phosphatides, for example, soy bean, lecithin, and esters or partial esters derived from fatty acids; hexitol anhydrides, for example, sorbitan monooleate; and condensation products of partial esters with ethylene oxide, for example, polyoxyethylene sorbitan monooleate.

The pharmaceutical compositions typically comprise a therapeutically effective amount of an AhR modulator as provided herein and one or more pharmaceutically and physiologically acceptable formulation agents. Suitable pharmaceutically acceptable or physiologically acceptable diluents, carriers or excipients include, but are not limited to, antioxidants (e.g., ascorbic acid and sodium bisulfate), preservatives (e.g., benzyl alcohol, methyl parabens, ethyl or n-propyl, p-hydroxybenzoate), emulsifying agents, suspending agents, dispersing agents, solvents, fillers, bulking agents, detergents, buffers, vehicles, diluents, and/or adjuvants. For example, a suitable vehicle may be physiological saline solution or citrate buffered saline, possibly supplemented with other materials common in pharmaceutical compositions for parenteral administration. Neutral buffered saline or saline mixed with serum albumin are further exemplary vehicles. Those skilled in the art will readily recognize a variety of buffers that can be used in the pharmaceutical compositions and dosage forms contemplated herein. Typical buffers include, but are not limited to, pharmaceutically acceptable weak acids, weak bases, or mixtures thereof. As an example, the buffer components can be water soluble materials such as phosphoric acid, tartaric acids, lactic acid, succinic acid, citric acid, acetic acid, ascorbic acid, aspartic acid, glutamic acid, and salts thereof. Acceptable buffering agents include, for example, a Tris buffer, N-(2-Hydroxyethyl)piperazine-N'-(2-ethanesulfonic acid) (HEPES), 2-(N-Morpholino)ethanesulfonic acid (MES), 2-(N-Morpholino)ethanesulfonic acid sodium salt (MES), 3-(N-Morpholino)propanesulfonic acid (MOPS), and N-tris[Hydroxymethyl]methyl-3-aminopropanesulfonic acid (TAPS).

After a pharmaceutical composition has been formulated, it may be stored in sterile vials as a solution, suspension, gel, emulsion, solid, or dehydrated or lyophilized powder. Such formulations may be stored either in a ready-to-use form, a lyophilized form requiring reconstitution prior to use, a liquid form requiring dilution prior to use, or other acceptable form. In some embodiments, the pharmaceutical composition is provided in a single-use container (e.g., a single-use vial, ampoule, syringe, or autoinjector (similar to, e.g., an EpiPen®)), whereas a multi-use container (e.g., a multi-use vial) is provided in other embodiments.

Formulations can also include carriers to protect the composition against rapid degradation or elimination from the body, such as a controlled release formulation, including liposomes, hydrogels, prodrugs and microencapsulated delivery systems. For example, a time delay material such as glyceryl monostearate or glyceryl stearate alone, or in combination with a wax, may be employed. Any drug delivery apparatus may be used to deliver an AhR modulator, including implants (e.g., implantable pumps) and catheter systems, slow injection pumps and devices, all of which are well known to the skilled artisan.

Depot injections, which are generally administered subcutaneously or intramuscularly, may also be utilized to release the AhR modulators disclosed herein over a defined period of time. Depot injections are usually either solid- or oil-based and generally comprise at least one of the formulation components set forth herein. One of ordinary skill in the art is familiar with possible formulations and uses of depot injections.

The pharmaceutical compositions may be in the form of a sterile injectable aqueous or oleagenous suspension. This suspension may be formulated according to the known art using those suitable dispersing or wetting agents and suspending agents mentioned herein. The sterile injectable preparation may also be a sterile injectable solution or suspension in a non-toxic parenterally-acceptable diluent or solvent, for example, as a solution in 1,3-butane diol. Acceptable diluents, solvents and dispersion media that may be employed include water, Ringer's solution, isotonic sodium chloride solution, Cremophor EL™ (BASF, Parsippany, N.J.) or phosphate buffered saline (PBS), ethanol, polyol (e.g., glycerol, propylene glycol, and liquid polyethylene glycol), and suitable mixtures thereof. In addition, sterile, fixed oils are conventionally employed as a solvent or suspending medium. For this purpose any bland fixed oil may be employed, including synthetic mono- or diglycerides. Moreover, fatty acids such as oleic acid, find use in the preparation of injectables. Prolonged absorption of particular injectable formulations can be achieved by including an agent that delays absorption (e.g., aluminum monostearate or gelatin).

The present invention contemplates the administration of the AhR modulators in the form of suppositories for rectal administration. The suppositories can be prepared by mixing the drug with a suitable non-irritating excipient which is solid at ordinary temperatures but liquid at the rectal temperature and will therefore melt in the rectum to release the drug. Such materials include, but are not limited to, cocoa butter and polyethylene glycols.

The AhR modulators contemplated by the present invention may be in the form of any other suitable pharmaceutical composition (e.g., sprays for nasal or inhalation use) currently known or developed in the future.

Routes of Administration

The present invention contemplates the administration of one or more AhR modulators as provided herein, and compositions thereof, in any appropriate manner. Suitable routes of administration include oral, parenteral (e.g., intramuscular, intravenous, subcutaneous (e.g., injection or implant), intraperitoneal, intracisternal, intraarticular, intraperitoneal, intracerebral (intraparenchymal) and intracerebroventricular), nasal, vaginal, sublingual, intraocular, rectal, topical (e.g., transdermal), buccal and inhalation. Depot injections, which are generally administered subcutaneously or intramuscularly, may also be utilized to release the AhR modulators disclosed herein over a defined period of time.

Particular embodiments of the present invention contemplate oral administration.

Combination Therapy

The present invention contemplates the use of AhR modulators in combination with one or more active therapeutic agents (e.g., chemotherapeutic agents) or other prophylactic or therapeutic modalities (e.g., radiation). In such combination therapy, the various active agents frequently have different, complementary mechanisms of action. Such combination therapy may be especially advantageous by allowing a dose reduction of one or more of the agents, thereby reducing or eliminating the adverse effects associated with one or more of the agents. Furthermore, such combination therapy may have a synergistic therapeutic or prophylactic effect on the underlying disease, disorder, or condition.

As used herein, "combination" is meant to include therapies that can be administered separately, for example, formulated separately for separate administration (e.g., as may be provided in a kit), and therapies that can be administered together in a single formulation (i.e., a "co-formulation").

In certain embodiments, the AhR modulators are administered or applied sequentially, e.g., where one agent is administered prior to one or more other agents. In other embodiments, the AhR modulators are administered simultaneously, e.g., where two or more agents are administered at or about the same time; the two or more agents may be present in two or more separate formulations or combined into a single formulation (i.e., a co-formulation). Regardless of whether the two or more agents are administered sequentially or simultaneously, they are considered to be administered in combination for purposes of the present invention.

The AhR modulators of the present invention may be used in combination with at least one other (active) agent in any manner appropriate under the circumstances. In one embodiment, treatment with the at least one active agent and at least one AhR modulator of the present invention is maintained over a period of time. In another embodiment, treatment with the at least one active agent is reduced or discontinued (e.g., when the subject is stable), while treatment with an AhR modulator of the present invention is maintained at a constant dosing regimen. In a further embodiment, treatment with the at least one active agent is reduced or discontinued (e.g., when the subject is stable), while treatment with an AhR modulator of the present invention is reduced (e.g., lower dose, less frequent dosing or shorter treatment regimen). In yet another embodiment, treatment with the at least one active agent is reduced or discontinued (e.g., when the subject is stable), and treatment with the AhR modulator of the present invention is increased (e.g., higher dose, more frequent dosing or longer treatment regimen). In yet another embodiment, treatment with the at least one active agent is maintained and treatment with the AhR modulator of the present invention is reduced or discontinued (e.g., lower dose, less frequent dosing or shorter treatment regimen). In yet another embodiment, treatment with the at least one active agent and treatment with the AhR modulator of the present invention are reduced or discontinued (e.g., lower dose, less frequent dosing or shorter treatment regimen).

Oncology-related Disorders. The present invention provides methods for treating and/or preventing a proliferative condition, cancer, tumor, or precancerous disease, disorder or condition with an AhR modulator and at least one additional therapeutic or diagnostic agent.

In certain embodiments, the present invention provides methods for tumor suppression of tumor growth comprising administration of an AhR modulator described herein in combination with a signal transduction inhibitor (STI) to achieve additive or synergistic suppression of tumor growth. As used herein, the term "signal transduction inhibitor" refers to an agent that selectively inhibits one or more steps in a signaling pathway. Examples of signal transduction inhibitors (STIs) useful in methods described herein include, but are not limited to: (i) bcr/abl kinase inhibitors (e.g., GLEEVEC); (ii) epidermal growth factor (EGF) receptor inhibitors, including kinase inhibitors and antibodies; (iii) her-2/neu receptor inhibitors (e.g., HERCEPTIN); (iv) inhibitors of Akt family kinases or the Akt pathway (e.g., rapamycin); (v) cell cycle kinase inhibitors (e.g., flavopiridol); and (vi) phosphatidyl inositol kinase inhibitors. Agents involved in immunomodulation can also be used in combination with one or more AhR modulators described herein for the suppression of tumor growth in cancer patients.

Examples of chemotherapeutic agents include, but are not limited to, alkylating agents such as thiotepa and cyclosphosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethylenethiophosphaoramide and trimethylolomelamime; nitrogen mustards such as chiorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, ranimustine; antibiotics such as aclacinomysins, actinomycin, authramycin, azaserine, bleomycins, cactinomycin, calicheamicin, carabicin, caminomycin, carzinophilin, chromomycins, dactinomycin, daunorubicin, detorubicin, 6-diazo-5-oxo-L-norleucine, doxorubicin, epirubicin, esorubicin, idarubicin, marcellomycin, mitomycins, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogs such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine, 5-FU; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; amsacrine; bestrabucil; bisantrene; edatraxate; defofamine; demecolcine; diaziquone; elformithine; elliptinium acetate; etoglucid; gallium nitrate; hydroxyurea; lentinan; lonidamine; mitoguazone; mitoxantrone; mopidamol; nitracrine; pentostatin; phenamet; pirarubicin; podophyllinic acid; 2-ethylhydrazide; procarbazine; razoxane; sizofiran; spirogermanium; tenuazonic acid; triaziquone; 2,2',2"-trichlorotriethylamine; urethan; vindesine; dacarbazine; mannomustine; mitobronitol; mitolactol; pipobroman; gacytosine; arabinoside (Ara-C); cyclophosphamide; thiotepa; taxoids, e.g., paclitaxel and doxetaxel; chlorambucil; gemcitabine; 6-thioguanine; mercaptopurine; methotrexate; platinum and platinum coordination complexes such as cisplatin and carboplatin; vinblastine; etoposide (VP-16); ifosfamide; mitomycin C; mitoxantrone; vincristine; vinorelbine; navelbine; novantrone; teniposide; daunomycin; aminopterin; xeloda; ibandronate; CPT11; topoisomerase inhibitors; difluoromethylornithine (DMFO); retinoic acid; esperamicins; capecitabine; and pharmaceutically acceptable salts, acids or derivatives of any of the above.

Chemotherapeutic agents also include anti-hormonal agents that act to regulate or inhibit hormonal action on tumors such as anti-estrogens, including for example tamoxifen, raloxifene, aromatase inhibiting 4(5)-imidazoles, 4-hydroxytamoxifen, trioxifene, keoxifene, onapristone, and toremifene; and antiandrogens such as flutamide, nilutamide, bicalutamide, enzalutamide, apalutamide, abiraterone acetate, leuprolide, and goserelin; and pharmaceutically acceptable salts, acids or derivatives of any of the above. In certain embodiments, combination therapy comprises administration of a hormone or related hormonal agent.

Additional treatment modalities that may be used in combination with an AhR modulator include radiotherapy, a monoclonal antibody against a tumor antigen, a complex of a monoclonal antibody and toxin, a T-cell adjuvant, bone marrow transplant, or antigen presenting cells (e.g., dendritic cell therapy).

Immune Checkpoint Inhibitors. The present invention contemplates the use of the modulators of AhR function described herein in combination with immune checkpoint inhibitors.

The tremendous number of genetic and epigenetic alterations that are characteristic of all cancers provides a diverse set of antigens that the immune system can use to distinguish tumor cells from their normal counterparts. In the case of T cells, the ultimate amplitude (e.g., levels of cytokine production or proliferation) and quality (e.g., the type of immune response generated, such as the pattern of cytokine production) of the response, which is initiated through antigen recognition by the T-cell receptor (TCR), is regulated by a balance between co-stimulatory and inhibitory signals (immune checkpoints). Under normal physiological conditions, immune checkpoints are crucial for the prevention of autoimmunity (i.e., the maintenance of self-tolerance) and also for the protection of tissues from damage when the immune system is responding to pathogenic infection. The expression of immune checkpoint proteins can be dysregulated by tumors as an important immune resistance mechanism.

Examples of immune checkpoints include but are not limited to CTLA-4, PD-1/L1, BTLA, TIM3, LAG3, OX40, 41BB, VISTA, CD96, TGFβ, CD73, CD39, A2AR, A2BR, IDO1, TDO2, Arginase, B7-H3, B7-H4. Cell-based modulators of anti-cancer immunity are also contemplated. Examples of such modulators include but are not limited to chimeric antigen receptor T-cells, tumor infiltrating T-cells and dendritic-cells.

The present invention contemplates the use of the AhR modulators described herein in combination with inhibitors of the aforementioned immune-checkpoint receptors and ligands, as well as yet-to-be-described immune-checkpoint receptors and ligands. Certain modulators of immune checkpoints are currently available, whereas others are in late-stage development. To illustrate, when it was approved for the treatment of melanoma in 2011, the fully humanized CTLA4 monoclonal antibody ipilimumab (YERVOY; Bristol-Myers Squibb) became the first immune checkpoint inhibitor to receive regulatory approval in the US. Fusion proteins comprising CTLA4 and an antibody (CTLA4-Ig; abatcept (ORENCIA; Bristol-Myers Squibb)) have been used for the treatment of rheumatoid arthritis, and other fusion proteins have been shown to be effective in renal transplantation patients that are sensitized to Epstein Barr Virus. PD1 antibodies are under development (e.g., nivolumab (Bristol-Myers Squibb) and lambrolizumab (Merck)), and anti-PDL1 antibodies are also being evaluated (e.g., MPDL3280A (Roche)). Nivolumab has shown promise in patients with melanoma, lung and kidney cancer.

The present invention encompasses pharmaceutically acceptable salts, acids or derivatives of any of the above.

Metabolic and Cardiovascular Diseases. The present invention provides methods for treating and/or preventing certain cardiovascular- and/or metabolic-related diseases, disorders and conditions, as well as disorders associated therewith, with an AhR modulator and at least one additional therapeutic or diagnostic agent.

Examples of therapeutic agents useful in combination therapy for the treatment of hypercholesterolemia (and atherosclerosis as well) include statins (e.g., CRESTOR, LESCOL, LIPITOR, MEVACOR, PRAVACOL, and ZOCOR), which inhibit the enzymatic synthesis of cholesterol; bile acid resins (e.g., COLESTID, LO-CHOLEST, PREVALITE, QUESTRAN, and WELCHOL), which sequester cholesterol and prevent its absorption; ezetimibe (ZETIA), which blocks cholesterol absorption; fabric acid (e.g., TRICOR), which reduces triglycerides and may modestly increase HDL; niacin (e.g., NIACOR), which modestly lowers LDL cholesterol and triglycerides; and/or a combination of the aforementioned (e.g., VYTORIN (ezetimibe with simvastatin). Alternative cholesterol treatments that may be candidates for use in combination with the AhR modulators described herein include various supplements and herbs (e.g., garlic, policosanol, and guggul).

The present invention encompasses pharmaceutically acceptable salts, acids or derivatives of any of the above.

Immune-related Disorders and Disorders Having an Inflammatory Component. The present invention provides methods for treating and/or preventing immune-related diseases, disorders and conditions; and diseases, disorders and conditions having an inflammatory component; with an AhR modulator and at least one additional therapeutic or diagnostic agent.

Examples of therapeutic agents useful in combination therapy are specific to the underlying disease, disorder or condition, and are known to the skilled artisan.

Microbial Diseases. The present invention provides methods for treating and/or preventing viral, bacterial, fungal and parasitic diseases, disorders and conditions, as well as disorders associated therewith, with an AhR modulator and at least one additional therapeutic or diagnostic agent (e.g., one or more other antiviral agents and/or one or more agents not associated with viral therapy).

Such combination therapy includes anti-viral agents targeting various viral life-cycle stages and having different mechanisms of action, including, but not limiting to, the following: inhibitors of viral uncoating (e.g., amantadine and rimantidine); reverse transcriptase inhibitors (e.g., acyclovir, zidovudine, and lamivudine); agents that target integrase; agents that block attachment of transcription factors to viral DNA; agents (e.g., antisense molecules) that impact translation (e.g., fomivirsen); agents that modulate translation/ribozyme function; protease inhibitors; viral assembly modulators (e.g., rifampicin); antiretrovirals such as, for example, nucleoside analogue reverse transcriptase inhibitors (e.g., azidothymidine (AZT), ddl, ddC, 3TC, d4T); non-nucleoside reverse transcriptase inhibitors (e.g., efavirenz, nevirapine); nucleotide analogue reverse transcriptase inhibitors; and agents that prevent release of viral particles (e.g., zanamivir and oseltamivir). Treatment and/or prevention of certain viral infections (e.g., HIV) frequently entail a group ("cocktail") of antiviral agents.

Other antiviral agents contemplated for use in combination with an AhR modulator include, but are not limited to, the following: abacavir, adefovir, amantadine, amprenavir, ampligen, arbidol, atazanavir, atripla, boceprevirertet, cidofovir, combivir, darunavir, delavirdine, didanosine, docosanol, edoxudine, emtricitabine, enfuvirtide, entecavir, famciclovir, fosamprenavir, foscarnet, fosfonet, ganciclovir, ibacitabine, imunovir, idoxuridine, imiquimod, indinavir, inosine, various interferons (e.g., peginterferon alfa-2a), lopinavir, loviride, maraviroc, moroxydine, methisazone, nelfinavir, nexavir, penciclovir, peramivir, pleconaril, podophyllotoxin, raltegravir, ribavirin, ritonavir, pyramidine, saquinavir, stavudine, telaprevir, tenofovir, tipranavir, trifluridine, trizivir, tromantadine, truvada, valaciclovir, valganciclovir, vicriviroc, vidarabine, viramidine, and zalcitabine.

The present invention contemplates the use of the AhR modulators described herein in combination with antiparasitic agents. Such agents include, but are not limited to, thiabendazole, pyrantel pamoate, mebendazole, praziquantel, niclosamide, bithionol, oxamniquine, metrifonate, ivermectin, albendazole, eflornithine, melarsoprol, pentamidine, benznidazole, nifurtimox, and nitroimidazole. The skilled artisan is aware of other agents that may find utility for the treatment of parasitic disorders.

Embodiments of the present invention contemplate the use of the AhR modulators described herein in combination with agents useful in the treatment or prevention of bacterial disorders. Antibacterial agents can be classified in various manners, including based on mechanism of action, based on chemical structure, and based on spectrum of activity. Examples of antibacterial agents include those that target the bacterial cell wall (e.g., cephalosporins and penicillins) or the cell membrane (e.g., polymyxins), or interfere with essential bacterial enzymes (e.g., sulfonamides, rifamycins, and quinolines). Most antibacterial agents that target protein synthesis (e.g., tetracyclines and macrolides) are bacteriostatic, whereas agents such as the aminoglycoside are bactericidal. Another means of categorizing antibacterial agents is based on their target specificity; "narrow-spectrum" agents target specific types of bacteria (e.g., Gram-positive bacteria such as *Streptococcus*), while "broad-spectrum" agents have activity against a broader range of bacteria. The skilled artisan is aware of types of anti-bacterial agents that are appropriate for use in specific bacterial infections.

Embodiments of the present invention contemplate the use of the AhR modulators described herein in combination with agents useful in the treatment or prevention of fungal disorders. Antifungal agents include polyenes (e.g., amphotericin, nystatin, and pimaricin); azoles (e.g., fluconazole, itraconazole, and ketoconazole); allylamines (e.g., naftifine, and terbinafine) and morpholines (e.g., amorolfine); and antimetabolies (e.g., 5-fluorocytosine).

The present invention encompasses pharmaceutically acceptable salts, acids or derivatives of the agents (and members of the classes of agents) set forth above.

Dosing

The AhR modulators provided herein may be administered to a subject in an amount that is dependent upon, for example, the goal of administration (e.g., the degree of resolution desired); the age, weight, sex, and health and physical condition of the subject to which the formulation is being administered; the route of administration; and the nature of the disease, disorder, condition or symptom thereof. The dosing regimen may also take into consideration the existence, nature, and extent of any adverse effects associated with the agent(s) being administered. Effective dosage amounts and dosage regimens can readily be determined from, for example, safety and dose-escalation trials, in vivo studies (e.g., animal models), and other methods known to the skilled artisan.

In general, dosing parameters dictate that the dosage amount be less than an amount that could be irreversibly toxic to the subject (the maximum tolerated dose (MTD)) and not less than an amount required to produce a measurable effect on the subject. Such amounts are determined by, for example, the pharmacokinetic and pharmacodynamic parameters associated with ADME, taking into consideration the route of administration and other factors.

An effective dose (ED) is the dose or amount of an agent that produces a therapeutic response or desired effect in some fraction of the subjects taking it. The "median effective dose" or $ED_{50}$ of an agent is the dose or amount of an agent that produces a therapeutic response or desired effect in 50% of the population to which it is administered. Although the $ED_{50}$ is commonly used as a measure of reasonable expectance of an agent's effect, it is not necessarily the dose that a clinician might deem appropriate taking into consideration all relevant factors. Thus, in some situations the effective amount is more than the calculated $ED_{50}$, in other situations the effective amount is less than the calculated $ED_{50}$, and in still other situations the effective amount is the same as the calculated $ED_{50}$.

In addition, an effective dose of an AhR modulator, as provided herein, may be an amount that, when administered in one or more doses to a subject, produces a desired result relative to a healthy subject. For example, for a subject experiencing a particular disorder, an effective dose may be one that improves a diagnostic parameter, measure, marker and the like of that disorder by at least about 5%, at least about 10%, at least about 20%, at least about 25%, at least about 30%, at least about 40%, at least about 50%, at least about 60%, at least about 70%, at least about 80%, at least about 90%, or more than 90%, where 100% is defined as the diagnostic parameter, measure, marker and the like exhibited by a normal subject.

In certain embodiments, the AhR modulators contemplated by the present invention may be administered (e.g., orally) at dosage levels of about 0.01 mg/kg to about 50 mg/kg, or about 1 mg/kg to about 25 mg/kg, of subject body weight per day, one or more times a day, to obtain the desired therapeutic effect.

For administration of an oral agent, the compositions can be provided in the form of tablets, capsules and the like containing from 1.0 to 1000 milligrams of the active ingredient, particularly 1.0, 3.0, 5.0, 10.0, 15.0, 20.0, 25.0, 50.0, 75.0, 100.0, 150.0, 200.0, 250.0, 300.0, 400.0, 500.0, 600.0, 750.0, 800.0, 900.0, and 1000.0 milligrams of the active ingredient.

In certain embodiments, the dosage of the desired AhR modulator is contained in a "unit dosage form". The phrase "unit dosage form" refers to physically discrete units, each unit containing a predetermined amount of the AhR modulator, either alone or in combination with one or more additional agents, sufficient to produce the desired effect. It will be appreciated that the parameters of a unit dosage form will depend on the particular agent and the effect to be achieved.

Kits

The present invention also contemplates kits comprising an AhR modulator, and pharmaceutical compositions thereof. The kits are generally in the form of a physical structure housing various components, as described below, and may be utilized, for example, in practicing the methods described above.

A kit can include one or more of the AhR modulators disclosed herein (provided in, e.g., a sterile container), which may be in the form of a pharmaceutical composition suitable for administration to a subject. The AhR modulators can be provided in a form that is ready for use (e.g., a tablet or capsule) or in a form requiring, for example, reconstitution or dilution (e.g., a powder) prior to administration. When the AhR modulators are in a form that needs to be reconstituted or diluted by a user, the kit may also include diluents (e.g., sterile water), buffers, pharmaceutically acceptable excipients, and the like, packaged with or separately from the AhR modulators. When combination therapy is contemplated, the kit may contain the several agents separately or they may already be combined in the kit. Each component of the kit may be enclosed within an individual container, and all of the various containers may be within a single package. A kit of the present invention may be designed for conditions necessary to properly maintain the components housed therein (e.g., refrigeration or freezing).

A kit may contain a label or packaging insert including identifying information for the components therein and instructions for their use (e.g., dosing parameters, clinical pharmacology of the active ingredient(s), including mechanism of action, pharmacokinetics and pharmacodynamics, adverse effects, contraindications, etc.). Labels or inserts can include manufacturer information such as lot numbers and expiration dates. The label or packaging insert may be, e.g., integrated into the physical structure housing the components, contained separately within the physical structure, or affixed to a component of the kit (e.g., an ampule, tube or vial).

Labels or inserts can additionally include, or be incorporated into, a computer readable medium, such as a disk (e.g., hard disk, card, memory disk), optical disk such as CD- or DVD-ROM/RAM, DVD, MP3, magnetic tape, or an electrical storage media such as RAM and ROM or hybrids of these such as magnetic/optical storage media, FLASH media or memory-type cards. In some embodiments, the actual instructions are not present in the kit, but means for obtaining the instructions from a remote source, e.g., via the internet, are provided.

EXAMPLES

The following examples are put forth so as to provide those of ordinary skill in the art with a complete disclosure and description of how to make and use the present invention, and are not intended to limit the scope of what the inventors regard as their invention, nor are they intended to represent that the experiments below were performed or that they are all of the experiments that may be performed. It is to be understood that exemplary descriptions written in the present tense were not necessarily performed, but rather the descriptions can be performed to generate data and the like of a nature described therein. Efforts have been made to ensure accuracy with respect to numbers used (e.g., amounts, temperature, etc.), but some experimental errors and deviations should be accounted for.

Unless indicated otherwise, parts are parts by weight, molecular weight is weight average molecular weight, temperature is in degrees Celsius (° C.), and pressure is at or near atmospheric. Standard abbreviations are used, including the following: μg=microgram; μl or μL=microliter; μM=micromolar; mM=millemolar; aa=amino acid(s); Ac$_2$O=acetic anhydride; AcCl=acetylchloride; ACN=acetonitrile; AIBN=2,2'-Azobis(2-methylpropionitrile); BID=twice daily; BINAP=2,2'-bis(diphenylphosphino)-1,1'-binaphthyl; Boc$_2$O or (Boc)$_2$O=di-tert-butyl dicarbonate; bp=base pair(s); BSA=bovine serum albumin; BW=body weight; d=doublet; dd=doublet of doublets; DEAD=diethyl azodicarboxylate; DIBAL=diisobutylaluminium hydride DIEA=N,N-diisopropylethylamine; DIPEA=N,N-diisopropylethylamine; dl or dL=deciliter; DMA=dimethylacetamide; DMAP=dimethylaminopyridine; DME=1,2-dimethoxyethane; DMEM=Dulbeco's Modification of Eagle's Medium; DMF=N,N-dimethylformamide; DMSO=dimethylsulfoxide; dppf=1,1'-Bis(diphenylphosphino)ferrocene; DTT=dithiothreitol; EDTA=ethylenediaminetetraacetic acid; ES=electrospray; EtOAc=ethyl acetate; EtOH=ethanol; g=gram; h or hr=hour(s); HATU=2-(1H-7-azabenzotriazol-1-yl)-1,1,3,3-tetramethyluronium hexafluorophosphate; HEPES=4-(2-hydroxyethyl)-1-piperazineethylanesulfonic acid; HOAc=acetic acid; HPLC=high performance liquid chromatography; HPLC=high pressure liquid chromatography; i.m.=intramuscular(ly); i.p.=intraperitoneal(ly); IHC=immunohistochemistry; IPA=isopropyl alcohol; kb=kilobase(s); kDa=kilodalton; kg=kilogram; 1 or L=liter; LC=liquid chromatography; LCMS=liquid chromatography and mass spectrometry; m/z=mass to charge ratio; M=molar; m=multiplet; MeCN=acetonitrile; MeOH=methanol; MeSO$_2$Cl=methanesulfonylchloride; mg=milligram; min=minute(s); min=minutes; ml or mL=milliliter; mM=millimolar; MS=mass spectrometry; MsCl=methanesulfonylchloride; N=normal; NADPH=nicotinamide adenine dinucleotide phosphate; NBS=N-bromosuccinamide; ng=nanogram; nm=nanometer; nM=nanomolar; NMP=N-methylpyrrolidone; NMR=nuclear magnetic resonance; ns=not statistically significant; nt=nucleotides(s); PBS=phosphate-buffered saline; Pd/C=palladium on carbon; Pd$_2$(dba)$_3$=Tris (debenzylideneactone) dipalladium; Pd(dppf)Cl$_2$=1,1'-bis (diphenylphosphino)ferrocene-palladium(11)dichloride; PE=petroleum ether; QD=daily; QM=monthly; QW=weekly; rac=racemic; Rt=retention time; s=singlet; s or sec=second(s); sat.=saturated; SC or SQ=subcutaneous (ly); t=triplet; TBAB=tetra-n-butylammonium bromide; TEA=triethylamine; TFA=trifluoroacetic acid; THF=tetrahydrofuran; TLC=thin layer chromatography; TMSCl=trimethylsilylchloride; TsOH=p-toluenesulfonic acid; U=unit; wt=wildtype.

Instrumentation

All masses reported are those of the protonated parent ions (M+H)$^+$ unless recorded otherwise.

Example 1

Synthesis of 4-(2-{[6-(5-methyl(3-pyridyl)-3-isopropyl-4-hydro-1,2,4-triazolo[4,3-a]pyrazin-8-yl]amino}ethyl)phenol

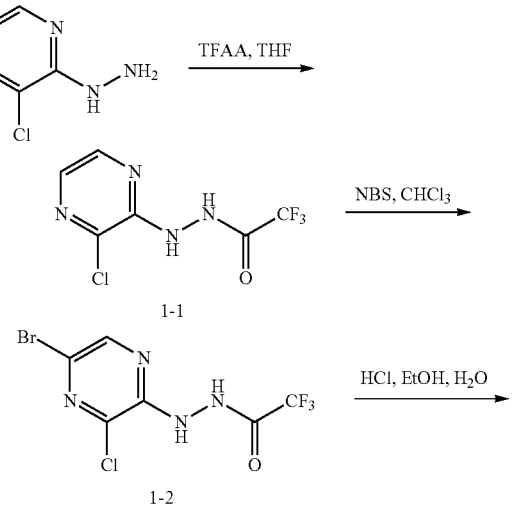

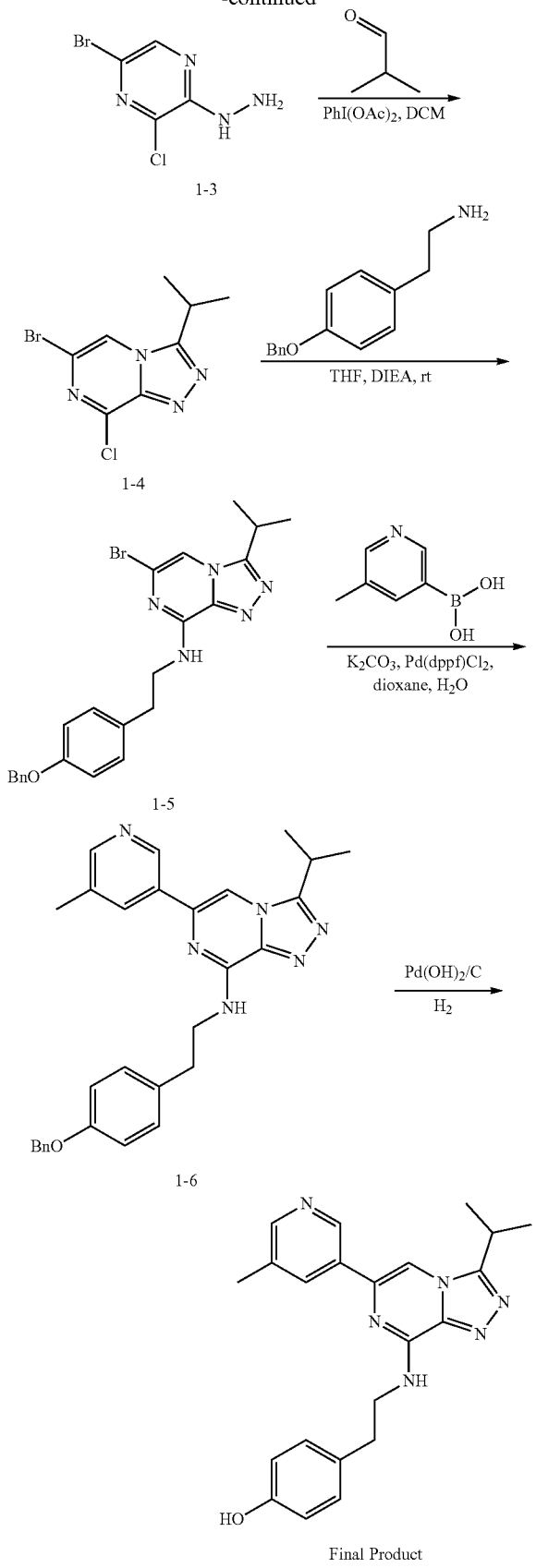

Step 1

Into a 500-mL 3-necked round-bottom flask, was added 2-chloro-3-hydrazinylpyrazine (5.0 g, 34.59 mmol, 1.00 equiv) in tetrahydrofuran (100 mL). While stirring this solution at 0° C. a solution of TFAA (8.0 g, 38.09 mmol, 1.10 equiv) in tetrahydrofuran (100 mL) was added dropwise. The resulting solution was stirred for 1 h and then washed with sodium chloride(aq). The resulting solution was extracted with ethyl acetate and the organic layers were combined and concentrated under vacuum. Purification by flash chromatography (silica gel column with ethyl acetate: petroleum ether (1:5)) provided 7.3 g (88%) of 1-1 as a white solid.

Step 2

Into a 500-mL 3-necked round-bottom flask, was added a solution of 1-1 (7.3 g, 30.34 mmol, 1.00 equiv) in chloroform (200 mL). While cooling the solution to 0° C., NBS (8.1 g, 45.51 mmol, 1.50 equiv) was added as a solid in several portions. The resulting solution was stirred for 1 h at 25° C. and then concentrated under vacuum. Purification by flash chromatography (silica gel column with ethyl acetate/petroleum ether (1:5)) provided 4.1 g (42%) of 1-2 as a yellow solid.

Step 3

Into a 250-mL 3-necked round-bottom flask, was placed a solution of 1-2 (4.1 g, 12.83 mmol, 1.00 equiv) in ethanol (80 mL), and hydrogen chloride (10 mL). The resulting solution was stirred for 2 second at 90° C. in an oil bath and then diluted with water. The pH value of the solution was adjusted to 8 with sodium bicarbonate. The resulting solution was extracted with ethyl acetate and the organic layers were combined and concentrated under vacuum. Purification by flash chromatography (silica gel column with ethyl acetate/petroleum ether (1:5)) provided 2.0 g (69%) of 1-3 as a yellow solid.

Step 4

Into a 100-mL 3-necked round-bottom flask, was placed a solution of 1-3 (2.0 g, 8.95 mmol, 1.00 equiv) in dichloromethane (20 mL), and 2-methylpropanal (1.3 g, 18.03 mmol, 2.00 equiv). The resulting solution was stirred for 12 h at 25° C. Then PhI(OAc)$_2$ (0.89 g, 1.30 equiv) was added into the solution with stirring and the reaction mixture heated for an additional 2 h at 25° C. The resulting solution was diluted with water. The solution was extracted with dichloromethane and the organic layers combined and concentrated under vacuum. Purification by flash chromatography (silica gel column with ethyl acetate/petroleum ether (1:5)) provided 1.82 g (74%) of 1-4 as a yellow solid.

Step 5

Into a 50-mL 3-necked round-bottom flask, was placed a solution of 1-4 (500 mg, 1.81 mmol, 1.00 equiv) in tetrahydrofuran (10 mL), 2-[4-(benzyloxy)phenyl]ethan-1-amine (822 mg, 3.62 mol, 2.00 equiv), and DIEA (700 mg, 5.42 mmol, 3.00 equiv). The resulting solution was stirred for 2 h at 25° C. and then diluted with water. The resulting solution was extracted with ethyl acetate and the organic layers combined and concentrated under vacuum. Purification by flash chromatography (silica gel column with dichloromethane/methanol (30:1)) provided 740 mg (87%) of 1-5 as a solid.

Step 6

Into a 10-mL vial purged and maintained with an inert atmosphere of nitrogen, was placed a solution of 1-5 (150 mg, 0.32 mmol, 1.00 equiv) in dioxane (2 mL), (5-methylpyridin-3-yl)boronic acid (88.2 mg, 0.644 mmol, 2.00 equiv), a solution of potassium carbonate (138 mg, 1.00 mmol, 3.00 equiv) in water (0.5 mL), and Pd(dppf)Cl$_2$ (731.7 mg, 1.00 mmol, 0.10 equiv) under N$_2$. The resulting solution was stirred for 4 h at 110° C. The resulting solution was diluted with water and extracted with ethyl acetate and the organic layers combined and concentrated under vacuum. Purification by flash chromatography (silica gel column with dichloromethane/methanol (20:1)) provided 130 mg (84%) of 1-6 as a white solid.

Step 7

Into a 100-mL round-bottom flask, was placed a solution of 1-6 (120 mg, 0.25 mmol, 1.00 equiv) in methanol (30 mL) and THF (6 ml), and Pd(OH)$_2$/C (30 mg). The resulting solution was stirred under H$_2$ pressure for 5 hours at 25° C. The solids were filtered out and the filtrate was concentrated under vacuum. Purification by flash chromatography (silica gel column with chloroform/methanol (30:1)) followed by recrystallization of the resulting solid from methanol:ACN:MTBE in the ratio of 1:2:10 provided 60 mg (62%) of the final product as a white solid. LCMS-(ES, m/z): [M+H]+ 389; H-NMR (400 MHz, DMSO, ppm): δ 1.40-1.42 (d, J=6.8 Hz, 6H), 2.40 (s, 3H), 2.89-2.90 (t, 2H), 3.51-3.61 (m, 1H), 3.71-3.79 (m, 2H), 6.68-6.70 (d, J=8.4 Hz, 2H), 7.09-7.11 (d, J=8.4 Hz, 2H), 8.26 (s, 1H), 8.30-8.35 (m, 2H), 8.42 (s, 1H), 9.09-9.10 (d, J=1.6 Hz, 1H), 9.17 (s, 1H).

Example 2

Synthesis of 5-(8-{[2-(4-hydroxyphenyl)ethyl]amino}-3-isopropyl-4-hydro-1,2,4-triazolo[4,3-a]pyrazin-6-yl)pyridine-3-carbonitrile

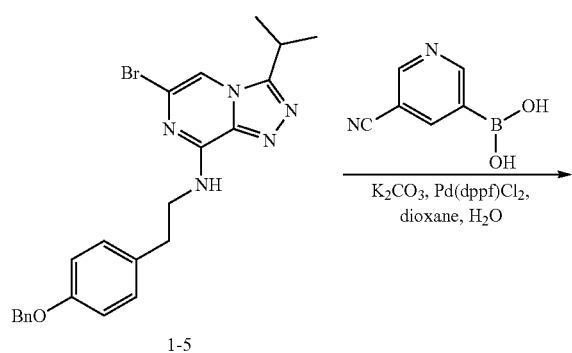

1-5

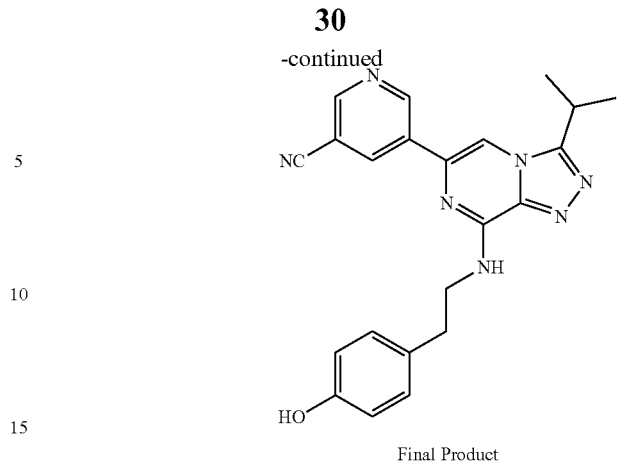

Final Product

Step 1

Into a 25-mL 3-necked round-bottom flask, was placed a solution of 1-5 (450 mg, 0.99 mmol, 1.00 equiv) in dioxane (6 mL), a solution of potassium carbonate (266 mg, 1.92 mmol, 2.00 equiv) in water (0.5 mL), Pd(dppf)Cl$_2$ (71 mg, 0.10 mmol, 0.10 equiv), and (5-cyanopyridin-3-yl)boronic acid (428 mg, 2.89 mmol, 3.00 equiv) under N$_2$. The resulting solution was stirred for 2 h at 80° C. in an oil bath and then diluted with water. The resulting solution was extracted with ethyl acetate and the organic layers combined and concentrated under vacuum. Purification by flash chromatography (silica gel column with dichloromethane/methanol (30:1)) provided 100 mg (22%) of 2-1 as a white solid.

Step 2

Into a 100-mL round-bottom flask, was placed a solution of 2-1 (100 mg, 0.20 mmol, 1.00 equiv) in methanol (20 mL), Pd/C (25 mg) and H$_2$ (g) was introduced. The resulting solution was stirred for 9 h at 25° C. and the solids were filtered out. The resulting mixture was concentrated under vacuum. Purification by flash chromatography (silica gel column with dichloromethane/methanol (40:1)) provided 18.1 mg (22%) of final compound as a white solid. LCMS (ES, m/z): [M+H]+ 400; H-NMR (400 MHz, DMSO, ppm): δ 1.42-1.44 (d, J=6.8 Hz, 6H), 2.88-2.92 (t, J=7.2 Hz, 2H), 3.53-3.60 (m, 1H), 3.75-3.76 (t, J=6.4 Hz, 2H), 6.67-6.70 (d, J=8.4 Hz, 2H), 7.09-7.11 (d, J=8.0 Hz, 2H), 8.42-8.47 (m, 1H), 8.55 (s, 1H), 8.93-8.94 (t, J=2.0 Hz, 1H), 9.03-9.04 (d, J=2.0 Hz, 1H), 9.17 (s, 1H), 9.56-9.57 (d, J=2.0 Hz, 1H).

Example 3

Synthesis of (2-indol-3-ylethyl)[6-(5-methyl(3-pyridyl)-3-isopropyl(4-hydro-1,2,4-triazolo[4,3-a]pyrazin-8-yl)]amine

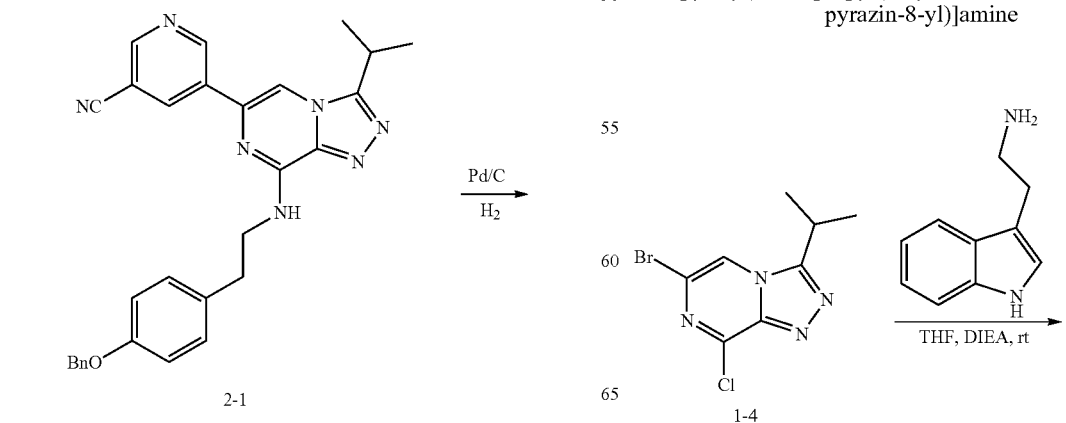

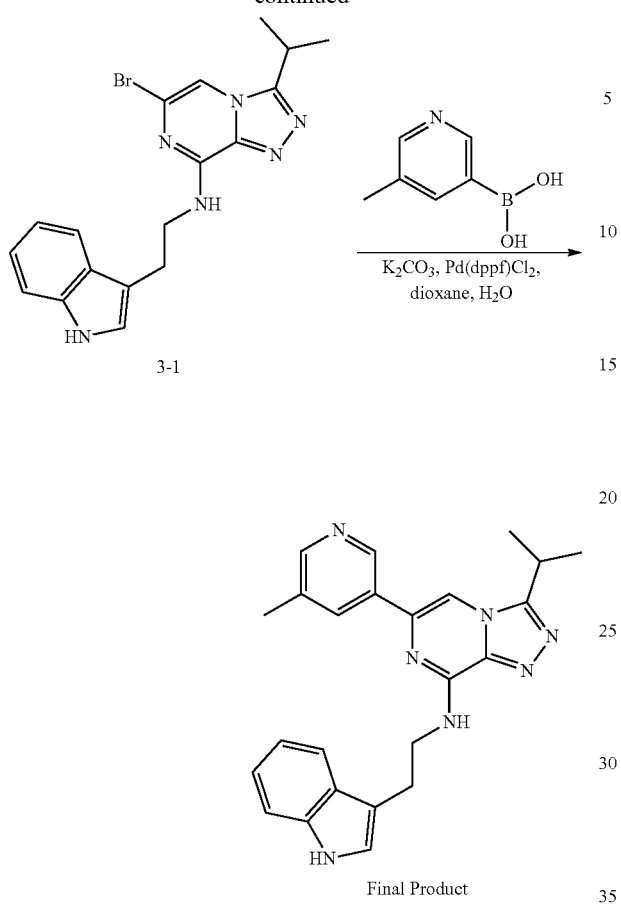

Example 4

Synthesis of 5-{8-[(2-indol-3-ylethyl)amino]-3-isopropyl-4-hydro-1,2,4-triazolo[4,3-a]pyrazin-6-yl}pyridine-3-carbonitrile

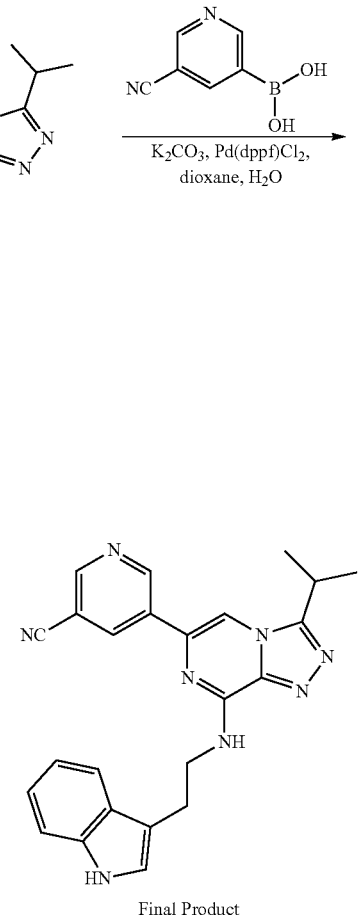

Step 1

Into a 8-mL vial, was placed 1-4 (280 mg, 1.02 mmol, 1 equiv), 2-(1H-indol-3-yl)ethan-1-amine (162.8 mg, 1.02 mmol, 1 equiv), THF (4 mL, 49.37 mmol, 48.584 equiv), and DIEA (262.7 mg, 2.03 mmol, 2 equiv). The resulting solution was stirred overnight at room temperature and then quenched with water. The resulting solution was extracted with ethyl acetate and the organic layer concentrated. Purification by flash chromatography (silica gel column with ethyl acetate/petroleum ether (1:5)) provided 260 mg (64.08%) of 3-1 as a white solid.

Step 2

Into a 8-mL vial, was placed 3-1 (130 mg, 0.33 mmol, 1 equiv), (5-methylpyridin-3-yl)boronic acid (66.9 mg, 0.49 mmol, 1.5 equiv), $K_2CO_3$ (90.0 mg, 0.65 mmol, 2 equiv), dioxane (2 mL), $H_2O$ (0.5 mL), and Pd(dppf)$Cl_2$ (23.8 mg, 0.03 mmol, 0.1 equiv). The resulting solution was stirred overnight at 100° C. and then diluted with water. The resulting solution was extracted with ethyl acetate and the organic layer concentrated. Purification by flash chromatography (silica gel column with ethyl acetate/petroleum ether (1:1)) provided 82.8 mg (61.80%) of final compound as a white solid. LCMS (ES, m/z): [M+H]+ 412; H-NMR (400 MHz, DMSO, ppm): δ 1.41-1.43 (d, 6H), 2.37 (s, 3H), 3.11-3.15 (t, 2H), 3.58-3.65 (m, 1H), 3.87-3.89 (m, 2H), 6.94-6.98 (t, 1H), 7.05-7.09 (t, 1H), 7.23-7.24 (d, 1H), 7.33-7.35 (d, 1H), 7.66-7.68 (d, 1H), 8.27 (s, 1H), 8.35 (s, 1H), 8.39-8.43 (t, 2H), 9.12 (s, 1H), 10.84 (s, 1H).

Step 1

Compound 3-1 (120 mg, 0.30 mmol, 1 equiv), (5-cyanopyridin-3-yl)boronic acid (66.7 mg, 0.45 mmol, 1.5 equiv), $K_2CO_3$ (83.1 mg, 0.60 mmol, 2 equiv), dioxane (2 mL), $H_2O$ (0.5 mL), and Pd(dppf)$Cl_2$ (22.0 mg, 0.03 mmol, 0.1 equiv) were placed in a round bottom flask. The resulting solution was stirred overnight at 100° C. and then diluted with water. The resulting solution was extracted with ethyl acetate and the organic layer was concentrated. Purification by flash chromatography (silica gel column with ethyl acetate/petroleum ether (1:1)) provided 66.6 mg (52.45%) of the final product as a light yellow solid. LCMS (ES, m/z): [M+H]+ 423; H-NMR (400 MHz, DMSO, ppm): δ 1.42-1.44 (d, 6H), 3.10-3.14 (t, 2H), 3.56-3.60 (m, 1H), 3.88-3.90 (m, 2H), 6.96-7.00 (t, 1H), 7.04-7.08 (t, 1H), 7.22-7.23 (d, 1H), 7.32-7.34 (d, 1H), 7.64-7.66 (d, 1H), 8.53 (s, 1H), 8.90-8.91 (t, 1H), 9.03-9.04 (d, 1H), 9.55-9.56 (d, 1H), 10.82 (s, 1H).

Example 5

Synthesis of 4-(2-{[6-(5-methyl(3-pyridyl)-3-isopropyl-4-hydroimidazo[1,2-a]pyrazin-8-yl]amino}ethyl)phenol

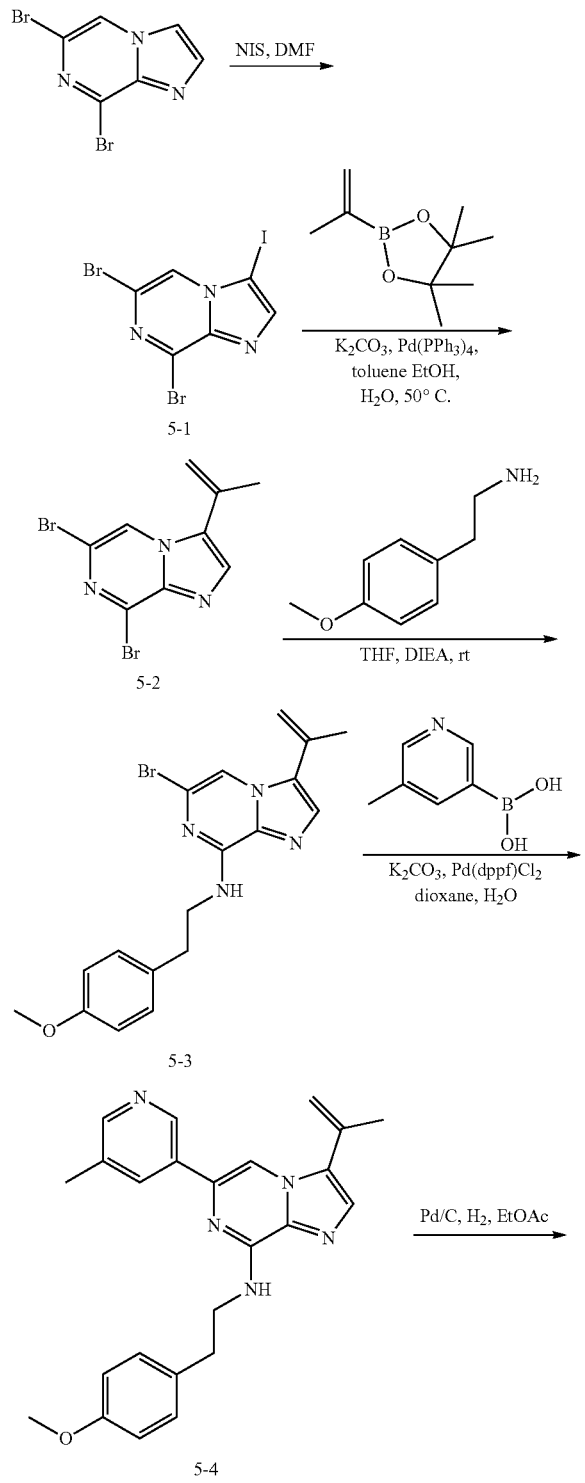

Step 1

Into a 250-mL 3-necked round-bottom flask purged and maintained with an inert atmosphere of nitrogen, were placed 6,8-dibromoimidazo[1,2-a]pyrazine (5 g, 18.06 mmol, 1.00 equiv) and N,N-dimethylformamide (125 mL). This was followed by the addition of NIS (4.3 g, 19.11 mmol, 1.05 equiv), in portions at room temperature. The resulting solution was stirred overnight at 60° C. in an oil bath. The reaction mixture was cooled to room temperature with a water/ice bath and then quenched with water. The resulting solution was extracted with ethyl acetate and the organic layers combined and concentrated under vacuum. Purification by flash chromatography (silica gel column with ethyl acetate/petroleum ether (1/2)) provided 2.8 g (38%) of 5-1 as a white solid.

Step 2

Into a 250-mL 3-necked round-bottom flask purged and maintained with an inert atmosphere of nitrogen, was placed 5-1 (2.8 g, 6.95 mmol, 1.00 equiv), toluene (60 mL), 4,4,5,5-tetramethyl-2-(prop-1-en-2-yl)-1,3,2-dioxaborolane (5.87 g, 34.93 mmol, 5.00 equiv), ethanol (30 mL), water (15 mL), potassium carbonate (1.93 g, 13.96 mmol, 2.00 equiv), and Pd(PPh$_3$)$_4$ (810 mg, 0.70 mmol, 0.10 equiv). The resulting solution was stirred overnight at 50° C. in an oil bath and then concentrated under vacuum. Purification by flash chromatography (silica gel column with ethyl acetate/petroleum ether (1/8)) provided 1.6 g crude of 5-2 as a yellow solid.

Step 3

Into a 8-mL sealed tube purged and maintained with an inert atmosphere of nitrogen, was placed 5-2 (100 mg, 0.32 mmol, 1.00 equiv), tetrahydrofuran (2 mL), 2-(4-methoxyphenyl)ethan-1-amine (238 mg, 1.57 mmol, 5.00 equiv), and DIEA (203 mg, 1.57 mmol, 5.00 equiv). The resulting solution was stirred for 2 h at room temperature and then quenched with water. The resulting solution was extracted with ethyl acetate and the organic layers combined and concentrated under vacuum. Purification by flash chromatography (silica gel Prep-TLC with ethyl acetate/petroleum ether (1/5)) provided 125 mg crude of 5-3 as a yellow solid.

Step 4

Into a 8-mL sealed tube purged and maintained with an inert atmosphere of nitrogen, was placed 5-3 (100 mg, 0.26 mmol, 1.00 equiv), dioxane (2 mL), water (0.5 mL), (5-methylpyridin-3-yl)boronic acid (106.5 mg, 0.78 mmol, 3.00 equiv), potassium carbonate (71.5 mg, 0.52 mmol, 2.00 equiv), and Pd(dppf)Cl$_2$ (19.0 mg, 0.03 mmol, 0.10 equiv). The resulting solution was stirred for 5 h at 80° C. in an oil bath and then quenched with water. The resulting solution was extracted with ethyl acetate and the organic layers combined and concentrated under vacuum. Purification by flash chromatography (silica gel Prep-TLC with dichloromethane/methanol (20/1)) provided 105 mg crude of 5-4 as a white solid.

Step 5

Into a 50-mL round-bottom flask, was placed 5-4 (100 mg, 0.25 mmol, 1.00 equiv), ethyl acetate (30 mL), and Palladium on carbon (20 mg). H$_2$(g) was introduced into the reaction mixture and the resulting solution was stirred for 2 h at room temperature. The solids were filtered out and the filtrate was concentrated under vacuum to provide 100 mg (99%) of 5-5 as a white solid.

Step 6

Into a 8-mL sealed tube purged and maintained with an inert atmosphere of nitrogen, was placed 5-5 (95 mg, 0.24 mmol, 1.00 equiv) in dichloromethane (2 mL). BBr$_3$ (592.3 mg, 10.00 equiv) was added dropwise with stirring at 0° C. The resulting solution was stirred for 2 h at 0° C. in a water/ice bath. The pH value of the solution was adjusted to 8 with sodium bicarbonate (aq). The resulting solution was extracted with dichloromethane and the organic layers combined and concentrated under vacuum. Purification by Prep-TLC (dichloromethane/methanol (20/1)) provided 32.3 mg (35%) of final product as a yellow solid. LCMS (ES, m/z): [M+H]$^+$ 388; H-NMR (400 MHz, DMSO, ppm): δ 1.33-1.35 (d, 6H), 2.40 (s, 3H), 2.87-2.90 (t, 2H), 3.38-3.45 (m, 1H), 3.68-3.74 (m, 2H), 6.69-6.71 (d, 2H), 7.09-7.11 (d, 2H), 7.33 (s, 1H), 7.57-7.60 (t, 1H), 8.27 (s, 2H), 8.40 (s, 1H), 9.11 (s, 1H), 9.17 (s, 1H).

Example 6

Synthesis of 5-(8-{[2-(4-hydroxyphenyl)ethyl]amino}-3-isopropyl-4-hydroimidazo[1,2-a]pyrazin-6-yl)pyridine-3-carbonitrile

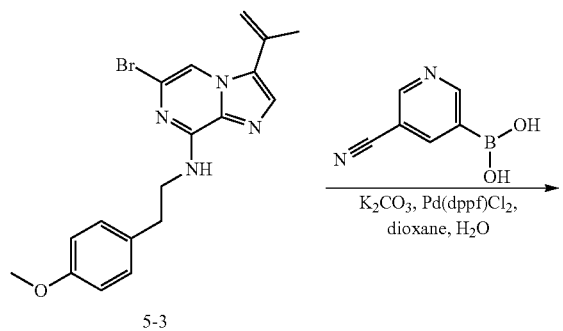

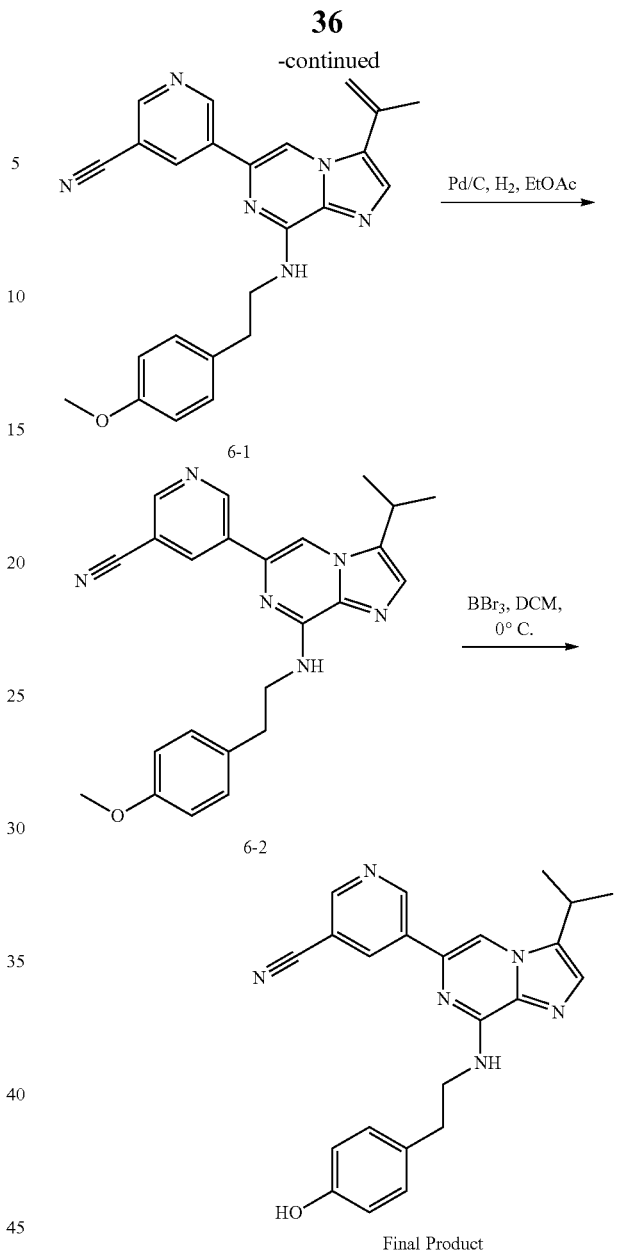

Step 1

Into a 50-mL 3-necked round-bottom flask under nitrogen, was placed 5-3 (200 mg, 0.52 mmol, 1.00 equiv), dioxane (4 mL), water (1 mL), (5-cyanopyridin-3-yl)boronic acid (230 mg, 1.55 mmol, 3.00 equiv), potassium carbonate (143 mg, 1.03 mmol, 2.00 equiv), and Pd(dppf)Cl$_2$ (38 mg, 0.05 mmol, 0.10 equiv). The resulting solution was stirred for 5 h at 80° C. in an oil bath and then quenched with water. The resulting solution was extracted with ethyl acetate and the organic layers combined and concentrated under vacuum. Purification by Prep-TLC (acetate/petroleum ether (1/3)) provided 200 mg (94%) of 6-1 as a white solid.

Step 2

Into a 100-mL round-bottom flask, was placed 6-1 (180 mg, 0.44 mmol, 1.00 equiv), ethyl acetate (45 mL), Palladium on carbon (45 mg) and H$_2$(g) was introduced into the reaction mixture. The resulting solution was stirred for 2 h at room temperature. The solids were filtered out and the resulting mixture was concentrated under vacuum to provide 180 mg (100%) of 6-2 as a white solid.

Step 3

Into a 8-mL sealed tube under nitrogen atmosphere, was placed 6-2 (170 mg, 0.41 mmol, 1.00 equiv) and dichloromethane (4 mL). BBr₃ (1.03 g, 10.00 equiv) was added dropwise with stirring at 0° C. and the resulting solution was stirred for 2 h at 0° C. in a water/ice bath. The pH value of the solution was adjusted to 8 with sodium bicarbonate (aq). The resulting solution was extracted with 2×20 mL of dichloromethane and the organic layers combined and concentrated under vacuum. Purification by Prep-TLC (dichloromethane/methanol (20/1)) provided 84.0 mg (51%) of final product as a white solid. LCMS (ES, m/z): [M+H]⁺ 399; H-NMR (300 MHz, DMSO, ppm): δ 1.34-1.36 (d, 6H), 2.86-2.91 (t, 2H), 3.38-3.45 (m, 1H), 3.70-3.77 (m, 2H), 6.68-6.71 (d, 2H), 7.09-7.11 (d, 2H), 7.37 (s, 1H), 7.72-7.76 (t, 1H), 8.50 (s, 1H), 8.95-9.00 (q, 2H), 9.18 (s, 1H), 9.58-9.59 (d, 1H).

Example 7

Synthesis of (2-indol-3-ylethyl)[6-(5-methyl(3-pyridyl))-3-isopropyl-(4-hydroimidazo[1,2-a]pyrazin-8-yl)]amine

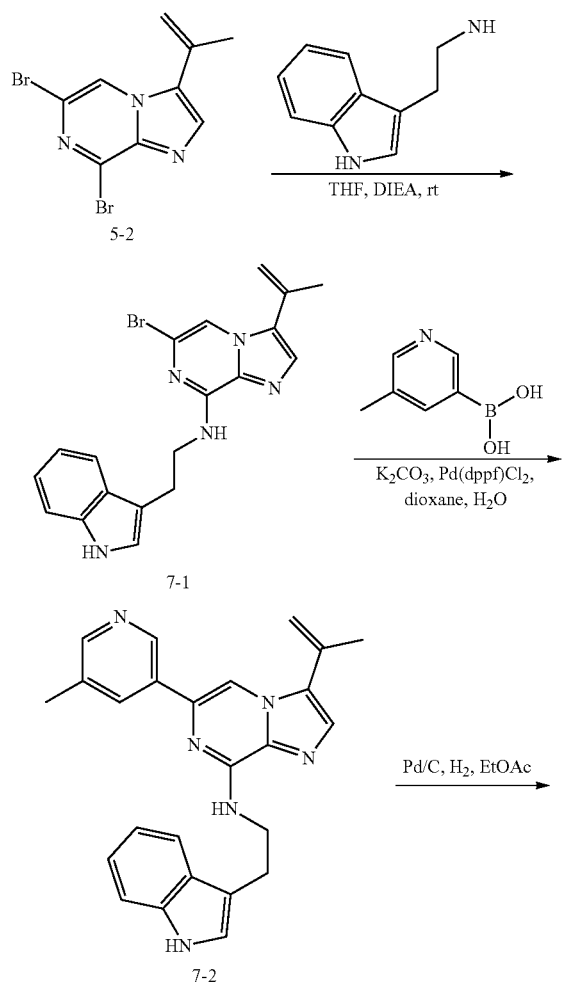

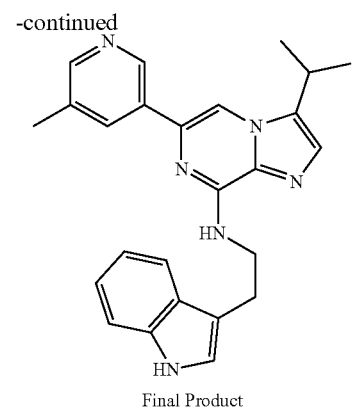

Final Product

Step 1

Into a 50-mL round-bottom flask under nitrogen atmosphere, was placed 5-2 (600 mg, 1.89 mmol, 1.00 equiv), tetrahydrofuran (15 mL), 2-(1H-indol-3-yl)ethan-1-amine (1.5 g, 9.36 mmol, 5.00 equiv), and DIEA (1.2 g, 9.29 mmol, 5.00 equiv). The resulting solution was stirred for 2 h at room temperature and then quenched with water. The resulting solution was extracted with ethyl acetate and the organic layers combined and concentrated under vacuum. Purification by Prep-TLC (dichloromethane/methanol (30/1)) provided 320 mg (43%) of 7-1 as a yellow solid.

Step 2

Into a 8-mL sealed tube purged and maintained with an inert atmosphere of nitrogen, was placed 7-1 (100 mg, 0.25 mmol, 1.00 equiv), dioxane (2 mL), water (0.5 mL), (5-methylpyridin-3-yl)boronic acid (104 mg, 0.76 mmol, 3.00 equiv), potassium carbonate (69.9 mg, 0.51 mmol, 2.00 equiv), and Pd(dppf)Cl₂ (18.5 mg, 0.03 mmol, 0.10 equiv). The resulting solution was stirred for 5 h at 80° C. in an oil bath and then quenched with water. The resulting solution was extracted with ethyl acetate and the organic layers combined and concentrated under vacuum. Purification by Prep-TLC (dichloromethane/methanol (30/1)) provided 85 mg (82%) of 7-2 as a yellow solid.

Step 3

Into a 100-mL round-bottom flask, was placed 7-2 (85 mg, 0.21 mmol, 1.00 equiv), ethyl acetate (50 mL), Palladium on carbon (20 mg) and H₂(g) was introduced into the reaction mixture. The resulting solution was stirred for 2 h at room temperature. The solids were filtered off and the resulting mixture was concentrated under vacuum. Purification by Prep-TLC (dichloromethane/methanol (30/1)) provided 42.3 mg (50%) of final product as a yellow solid. LCMS (ES, m/z): [M+H]⁺ 411; H-NMR (400 MHz, DMSO, ppm): δ 1.34-1.35 (d, 6H), 2.39 (s, 3H), 3.09-3.13 (t, 2H), 3.39-3.45 (m, 1H), 3.83-3.88 (m, 2H), 6.94-6.98 (t, 1H), 7.05-7.09 (t, 1H), 7.22-7.23 (d, 1H), 7.34-7.35 (d, 2H), 7.66-7.69 (m, 2H), 8.27-8.28 (d, 2H), 8.40 (s, 1H), 9.12 (s, 1H), 10.83 (s, 1H).

Example 8

Synthesis of 5-{8-[(2-indol-3-ylethyl)amino]-3-isopropyl-4-hydroimidazo[1,5-a]pyrazin-6-yl}pyridine-3-carbonitrile

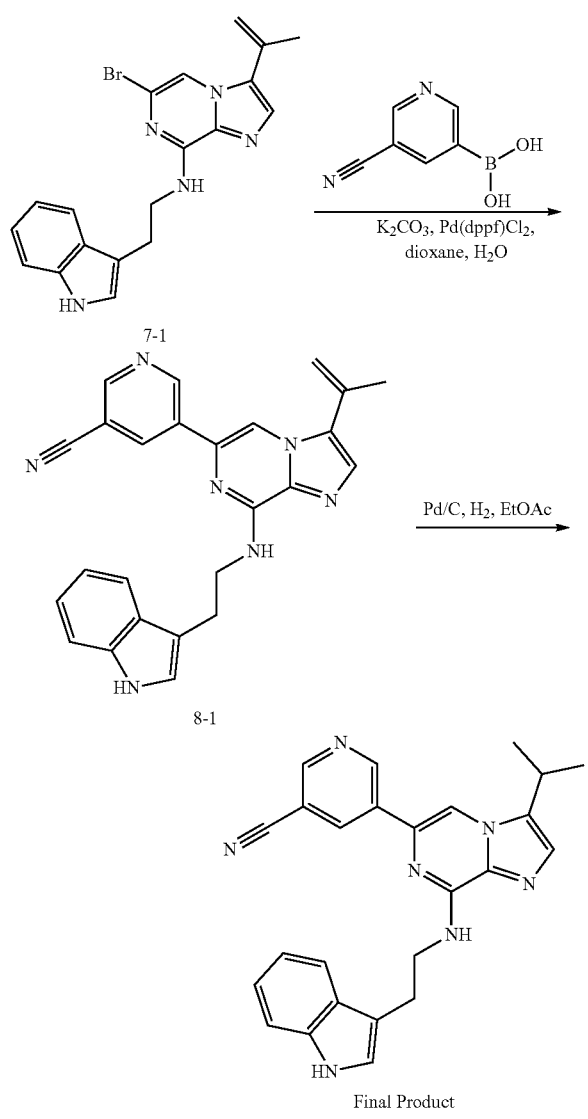

Step 1

Into a 8-mL sealed tube purged and maintained with an inert atmosphere of nitrogen, was placed 7-1 (100 mg, 0.25 mmol, 1.00 equiv), dioxane (2 mL), water (0.5 mL), (5-cyanopyridin-3-yl)boronic acid (112 mg, 0.76 mmol, 3.00 equiv), potassium carbonate (69.9 mg, 0.51 mmol, 2.00 equiv), and Pd(dppf)Cl$_2$ (18.5 mg, 0.03 mmol, 0.10 equiv). The resulting solution was stirred for 5 h at 80° C. in an oil bath and then quenched with water. The resulting solution was extracted with ethyl acetate and the organic layers combined and concentrated under vacuum. The residue was applied onto Prep-TLC with dichloromethane/methanol (50/1) to give 87 mg (82%) of 8-1 as a yellow solid.

Step 2

Into a 500-mL round-bottom flask, was placed 8-1 (87 mg, 0.21 mmol, 1.00 equiv), ethyl acetate (200 mL), Palladium on carbon (20 mg) and H$_2$(g) was introduced into the reaction mixture. The resulting solution was stirred for 2 h at room temperature. The solids were filtered off. The resulting mixture was concentrated under vacuum. Purification by Prep-TLC (dichloromethane/methanol (30/1)) provided 30.9 mg (36%) of final compound as a yellow solid. LCMS (ES, m/z): [M+H]$^+$ 422; H-NMR (400 MHz, DMSO, ppm): δ 1.35-1.37 (d, 6H), 3.08-3.18 (m, 2H), 3.36-3.45 (m, 1H), 3.84-3.91 (m, 2H), 6.97-7.09 (m, 2H), 7.23-7.22 (d, 1H), 7.33-7.37 (m, 2H), 7.66-7.68 (d, 1H), 7.79-7.83 (t, 1H), 8.48 (s, 1H), 8.93-9.01 (m, 2H), 9.59-9.60 (d, 1H), 10.83 (s, 1H).

Example 9

Synthesis of (2-indol-3-ylethyl)[6-(5-methyl(3-pyridyl)-3-isopropyl(4-hydroimidazo[1,5-a]pyrazin-8-yl)]amine

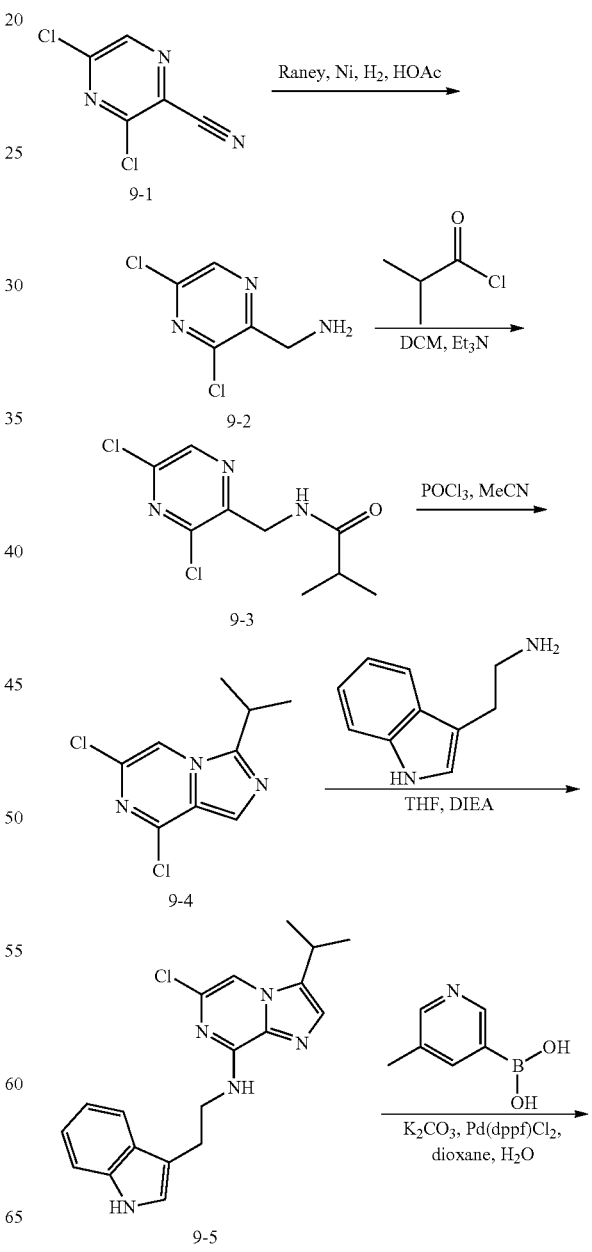

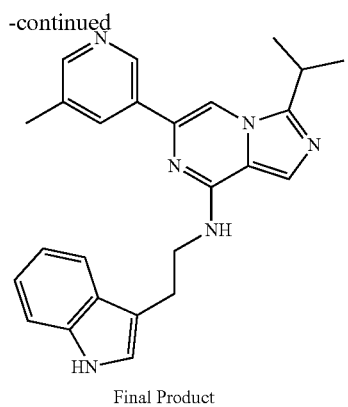

Final Product

Step 1

Into a 25-mL round-bottom flask, was placed 3,5-dichloropyrazine-2-carbonitrile (450 mg, 2.59 mmol, 1.00 equiv), and acetic acid (10 mL), followed Raney Ni (50 mg). H₂ was introduced into the reaction mixture. The resulting solution was stirred overnight at 50° C. in an oil bath. The solid was filtered out and the resulting mixture was concentrated under vacuum to give 560 mg (crude) of 9-2 as a green solid.

Step 2

Into a 25 mL round-bottom flask was placed 9-2 (560 mg, 3.08 mmol, 1 equiv), dichloromethane (5 mL), triethylamine (603 mg, 5.97 mmol, 1.94 equiv), and 2-methylpropanoyl chloride (326 mg, 3.08 mmol, 1.00 equiv). The resulting solution was stirred for 1 h at 0° C. and then quenched with H₂O. The resulting solution was extracted with dichloromethane and concentrated under vacuum. Purification by Prep-TLC (ethyl acetate/petroleum ether (1:1)) provided 9-3 (380 mg, 48.72%) as a yellow solid.

Step 3

Into a 50-mL round-bottom flask, was placed 9-3 (380 mg, 1.5 mol, 1.00 equiv), MeCN (15 mL), DMF (0.5 mL), and POCl₃ (281 mg, 1.8 mol, 1.21 equiv). The resulting solution was heated to reflux for 1 h in an oil bath and then quenched by the addition of 5 mL of NaHCO₃ (aq.). MeCN was evaporated in vacuum and the resulting solution was extracted with EA and the organic layer was concentrated. Purification by Prep-TLC (ethyl acetate/petroleum ether (1:2)) provided 280 mg (70%) of 9-4 as a yellow solid.

Step 4

Into a 8-mL vial, was placed 9-4 (130 mg, 560.0 mmol, 1 equiv), 2-(1H-indol-3-yl)ethan-1-amine (181.039 mg, 1.13 mol, 2 equiv), DIEA (146.041 mg, 1.13 mol, 2 equiv), and THF (4 mL). The resulting solution was stirred overnight at room temperature and then concentrated. Purification by flash chromatography (silica gel column with DCM/MeOH (30:1)) provided 180 mg (90.04%) of 9-5 as a yellow solid.

Step 5

Into a 8-mL vial purged and maintained with an inert atmosphere of nitrogen, was placed 9-5 (180 mg, 0.51 mmol, 1 equiv), (5-methylpyridin-3-yl)boronic acid (140 mg, 1.02 mmol, 2.010 equiv), K₂CO₃ (208 mg, 1.51 mmol, 2.959 equiv), dioxane (4 mL), H₂O (1 mL), and Pd(dppf)Cl₂ (37 mg, 0.05 mmol, 0.1 equiv). The resulting solution was stirred for 6 h at 80° C. The reaction was quenched with water and the resulting solution was extracted with ethyl acetate. Purification by Prep-TLC (DCM/MeOH=20:1) provided 129.1 mg (61.82%) of final product as a white solid. LCMS (ES, m/z): [M+]⁺ 411; H-NMR (400 MHz, DMSO, ppm): δ 1.32-1.34 (d, 6H), 2.37 (s, 3H), 3.09-3.13 (t, 2H), 3.57-3.59 (m, 1H), 3.82-3.84 (m, 2H), 6.97-6.99 (t, 1H), 7.05-7.07 (t, 1H), 7.22 (s, 1H), 7.34-7.36 (d, 1H), 7.64-7.66 (d, 1H), 7.69 (s, 1H), 7.87-7.89 (t, 1H), 8.18 (s, 1H), 8.27 (s, 1H), 8.38-8.39 (d, 1H), 9.11 (s, 1H), 10.84 (s, 1H).

Example 10

Synthesis of 4-(2-{[6-(5-methyl(3-pyridyl))-3-isopropyl-4-hydroimidazo[1,5-a]pyrazin-8-yl]amino}ethyl)phenol

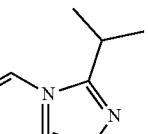

9-4

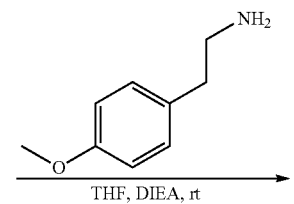

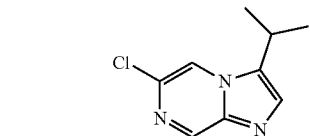

10-1

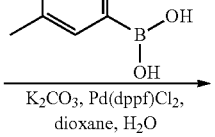

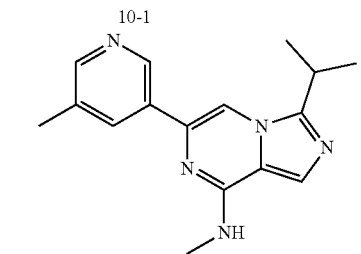

10-2

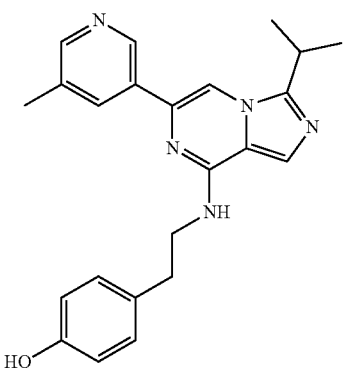

Final Product

Step 1

Into a 8 mL vial were added 9-4 (140 mg, 0.61 mmol, 1 equiv), 2-(4-methoxyphenyl)ethan-1-amine (184.0 mg, 1.22 mol, 2 equiv), THF (2 mL), and DIEA (157.3 mg, 1.22 mmol, 2 equiv) at room temperature. The resulting mixture was stirred overnight at room temperature and then concentrated under vacuum. Purification by Prep-TLC (petroleum ether/ethylacetate=1:1) provided 10-1 (120 mg, 57.19%) as a white solid.

Step 2

Into a 8-mL vial, was placed 10-1 (150 mg, 430.0 mmol, 1 equiv), (5-methylpyridin-3-yl)boronic acid (119.137 mg, 870.0 mmol, 2 equiv), $K_2CO_3$ (120.235 mg, 870.0 mmol, 2 equiv), dioxane (3 mL), $H_2O$ (0.6 mL), and $Pd(dppf)Cl_2$ (31.828 mg, 40.0 mmol, 0.1 equiv). The resulting solution was stirred under $N_2$ for 3 h at 80° C. and then quenched by the addition water. The resulting solution was extracted with ethyl acetate and concentrated under vacuum. Purification by Prep-TLC (dichloromethane/methanol (30:1)) provided 120 mg (68.71%) of 10-2 as a white solid.

Step 3

Into a 25-mL round-bottom flask, was placed 10-2 (120 mg, 300.0 mmol, 1 equiv), DCM (5 mL), followed by the addition of $BBr_3$ (224.626 mg, 900.0 mmol, 3 equiv) dropwise with stirring. The resulting solution was stirred for 3 h at room temperature and then quenched with 5 mL of $NaHCO_3$ (aq.). The resulting solution was extracted with dichloromethane and concentrated under vacuum. Purification by Prep-TLC (DCM/MeOH (15:1)) provided 63.9 mg (55.18%) of final product as a white solid. LCMS (ES, m/z): $[M+H]^+$ 388; H-NMR (400 MHz, DMSO, ppm): δ 1.31-1.33 (d, 6H), 2.38 (s, 3H), 2.86-2.90 (t, 2H), 3.54-3.61 (m, 1H), 3.65-3.71 (m, 2H), 6.69-6.71 (d, 2H), 7.09-7.11 (d, 2H), 7.68 (s, 1H), 7.80-7.83 (m, 1H), 8.18 (s, 1H), 8.26 (s, 1H), 8.37-8.38 (d, 1H), 9.09-9.10 (d, 1H), 9.18 (s, 1H).

Example 11

Synthesis of [2-(7-fluoroindol-3-yl)ethyl][3-isopropyl-6-(2-methylimidazolyl)(4-hydroimidazo[1,2-a]pyrazin-8-yl)]amine

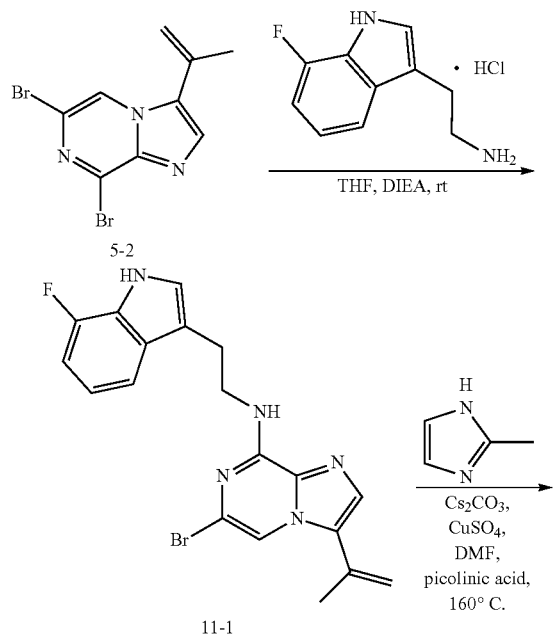

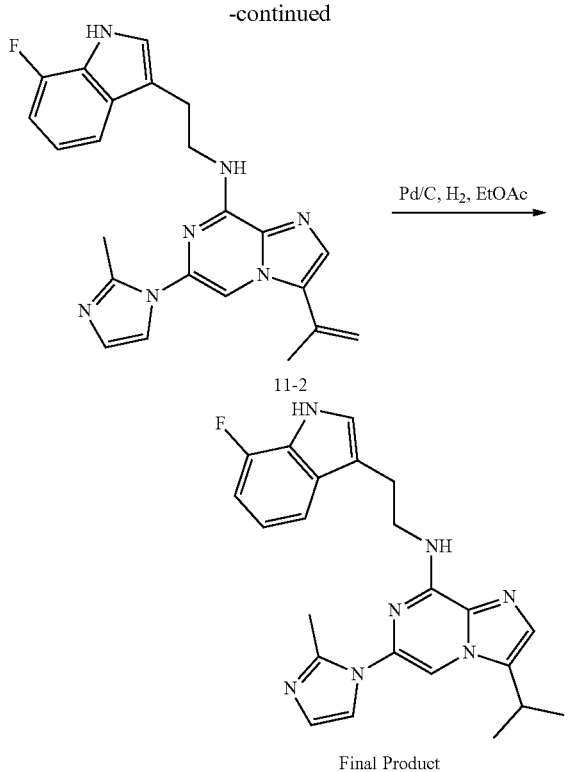

Final Product

Step 1

Into a 5 mL vial were added 5-2 (200 mg, 0.63 mmol, 1 equiv), 2-(7-fluoro-1H-indol-3-yl)ethan-1-amine hydrochloride (135.4 mg, 0.63 mmol, 1 equiv), THF (2 mL), and DIEA (163.1 mg, 1.26 mmol, 2 equiv) at room temperature. The resulting mixture was stirred for 5 h at room temperature and then diluted with water. The resulting mixture was extracted with EA (and the combined organic layer was concentrated under vacuum. Purification by Prep-TLC (petroleum ether/ethylacetate=2:1) to afford 11-1 203.9 mg (77.66%) as a yellow solid.

Step 2

Into an 8 mL vial were added 11-1 (190 mg, 460 mmol, 1 equiv), 2-methyl-1H-imidazole (75.3 mg, 920 mmol, 2 equiv), $Cs_2CO_3$ (479.0 mg, 1.47 mmol, 3 equiv), $CuSO_4$ (234.6 mg, 1.47 mmol, 3 equiv), picolinic acid (181 mg, 1.47 mmol, 3 equiv), and DMF (2 mL). The resulting mixture was stirred for 6 h at 160° C. and the diluted with water. The resulting mixture was extracted with EA. The combined organic layer was concentrated under vacuum. Purification by Prep-TLC ($CH_2Cl_2$/MeOH=20:1) to afford 11-2 96 mg (50.38%) as a yellow solid.

Step 3

To a stirred solution of 11-2 (86 mg, 210 mmol, 1 equiv) in EA (5 mL) was added Pd/C (17.2 mg, 160 mmol, 0.781 equiv), and the reaction was with stirred for 4 h at room temperature under an atmosphere of hydrogen. The resulting mixture was filtered. The filtrate was concentrated under vacuum. Purification by Prep-TLC ($CH_2Cl_2$/MeOH=20:1) to afford final product (42.9 mg, 49.64%) as a white solid. LCMS (ES, m/z): $[M+]^+$ 418; H-NMR (300 MHz, DMSO, ppm): δ 1.30-1.32 (d, 6H), 2.42 (s, 3H), 3.02-3.07 (t, 2H), 3.23 (s, 1H), 3.70-3.76 (m, 2H), 6.85-6.89 (m, 3H), 7.25 (s, 1H), 7.39-7.43 (m, 3H), 7.87 (s, 1H), 7.97-8.01 (m, 1H), 11.28 (s, 1H).

Example 12

Synthesis of [2-(6-fluoroindol-3-yl)ethyl][3-isopropyl-6-(2-methylimidazolyl)(4-hydroimidazo[1,2-a]pyrazin-8-yl)]amine

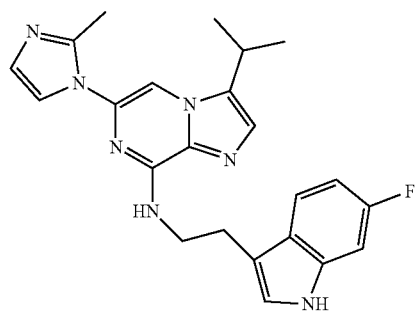

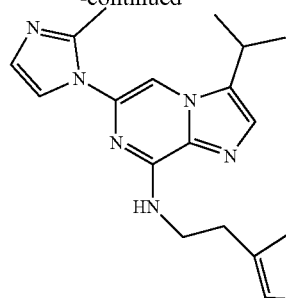

Final Product

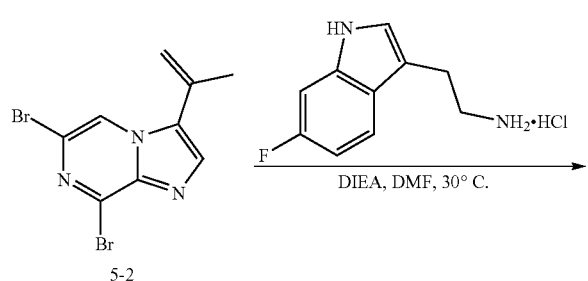

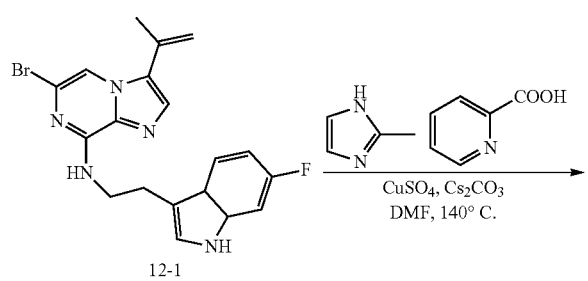

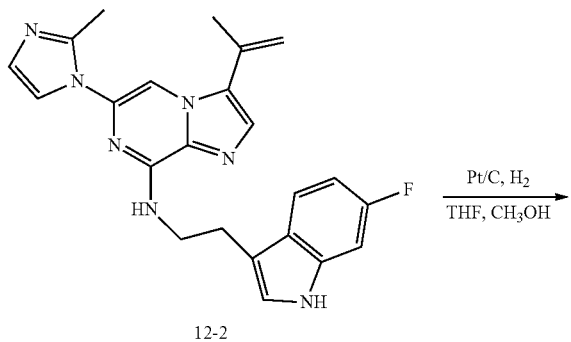

Step 1

Into a 8-mL vial, was placed 5-2 (200 mg, 0.63 mmol, 1.00 equiv), N,N-dimethylformamide (2.0 mL), 2-(6-fluoro-1H-indol-3-yl)ethan-1-amine (136 mg, 0.63 mmol, 1.00 equiv), and DIEA (244 mg, 1.89 mmol, 3.00 equiv). The resulting solution was stirred overnight at 30,° C. The resulting mixture was washed with $H_2O$. The resulting solution was extracted with ethyl acetate and the organic layers combined. Purification by Prep-TLC (dichloromethane/methanol (10/1)) provided 184 mg (70%) of 12-1 as a white solid.

Step 2

Into a 8-mL vial, was placed 12-1 (105 mg, 0.25 mmol, 1.00 equiv), N,N-dimethylformamide (2 mL), 2-methyl-1H-imidazole (416 mg, 5.07 mmol, 20.00 equiv), pyridine-2-carboxylic acid (72 mg, 0.58 mmol, 2.30 equiv), $Cs_2CO_3$ (248 mg, 0.76 mmol, 3.00 equiv), and $CuSO_4$ (141 mg, 0.89 mmol, 3.50 equiv) under $N_2$. The resulting solution was stirred overnight at 140° C. The resulting mixture was washed with $H_2O$. The resulting solution was extracted with ethyl acetate and the organic layers combined. The residue was applied onto TLC with dichloromethane/methanol (10/1) to give 74 mg (68%) of 12-2 as a white solid.

Step 3

Into a 50-mL round-bottom flask, was placed 12-2 (74 mg, 0.18 mmol, 1.00 equiv), tetrahydrofuran (5 mL), methanol (5 mL), and Pt/C (8 mg) and $H_2$ was introduced. The resulting solution was stirred overnight at room temperature. The solids were filtered out and the crude product was purified by Flash-Prep-HPLC under the following conditions: Column C18; mobile phase, $CH_3CN/H_2O=2/10$ increasing to $CH_3CN/H_2O=7/10$ within 40 min; Detector, UV 254 nm. This resulted in 18.4 mg (25%) of final product as a white solid. LCMS (ES, m/z): $[M+H]^+$ 418; H-NMR (400 MHz, DMSO, ppm): δ 1.32-1.31 (d, 6H), 2.33 (s, 3H), 3.04-3.00 (t, 2H), 3.32-3.29 (m, 1H), 3.72-3.71 (t, 2H), 6.78-6.73 (t, 1H), 6.91 (s, 1H), 7.10-7.07 (m, 1H), 7.19 (s, 1H), 7.39 (s, 2H), 7.59-7.56 (m, 1H), 7.88 (s, 1H), 8.05-7.97 (t, 1H), 10.87 (s, 1H).

Example 13

Synthesis of [2-(5-fluoroindol-3-yl)ethyl][3-isopropyl-6-(2-methylimidazolyl)(4-hydroimidazo[1,2-a]-pyrazin-8-yl)]amine

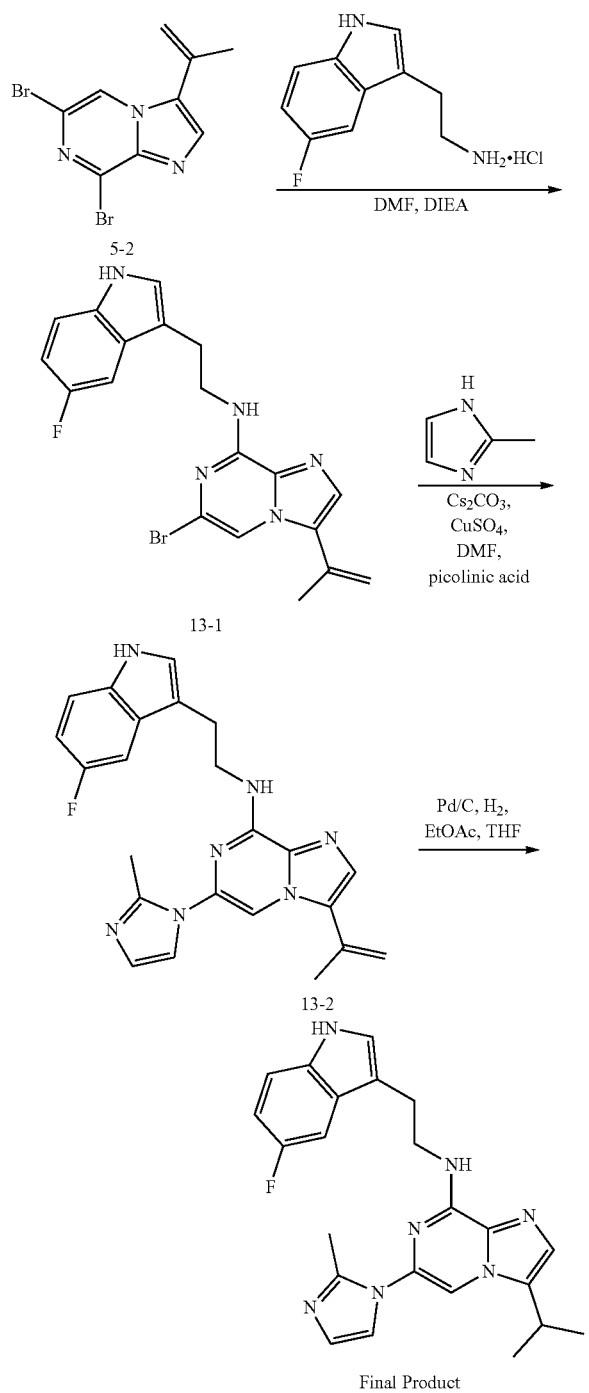

Step 1

To a stirred solution of 5-2 (200 mg, 0.63 mmol, 1 equiv) and 2-(5-fluoro-1H-indol-3-yl)ethan-1-amine (112.4 mg, 630 mmol, 1 equiv) in DMF (2 mL) was added DIEA (240 mg, 1.1 mmol, 1.8 equiv) at room temperature. The resulting mixture was stirred for 4 h at room temperature and then diluted with water. The resulting mixture was extracted with EA and the combined organic layer was concentrated under vacuum. Purification by Prep-TLC (petroleum ether/ethyl-acetate=2:1) to afford 13-1 (210 mg, 80.34%) as a white solid.

Step 2

Into a 8 mL vial were added 13-1 (190 mg, 0.46 mmol, 1 equiv), 2-methyl-1H-imidazole (75.3 mg, 0.92 mmol, 2 equiv), $Cs_2CO_3$ (448.3 mg, 1.38 mmol, 3 equiv), $CuSO_4$ (219.6 mg, 1.38 mmol, 3 equiv), picolinic acid (180 mg, 1.47 mmol, 3 equiv), and DMF (2 mL). The resulting mixture was stirred for 3 h at 140° C. and then diluted with water. The resulting mixture was extracted with EA and the combined organic layer was concentrated under vacuum. Purification by Prep-TLC ($CH_2Cl_2$/MeOH=20:1) afforded 13-2 (90 mg, 47.23%) as a white solid.

Step 3

To a stirred solution of 13-2 (90 mg, 220 mmol, 1 equiv) in THF (2.5 mL) and EA (2.5 mL) was added Pd/C (18 mg). The reaction was stirred for 1 h at room temperature under an atmosphere of hydrogen. The resulting mixture was filtered and the filtrate was concentrated under vacuum. Purification by Prep-TLC ($CH_2Cl_2$/MeOH=20:1) to afford final product 72.3 mg (79.95%) as a white solid. LCMS (ES, m/z): $[M+H]^+$ 418; H-NMR: (400 MHz, DMSO, ppm): δ 1.31-1.32 (d, 6H), 2.44 (s, 3H), 3.00-3.04 (t, 2H), 3.29-3.34 (m, 1H), 3.70-3.75 (m, 2H), 6.86-6.92 (m, 2H), 7.27-7.33 (m, 3H), 7.39 (s, 2H), 7.86 (s, 1H), 7.91-7.94 (m, 1H), 10.89 (s, 1H).

Example 14

Synthesis of [2-(4-fluoroindol-3-yl)ethyl][3-isopropyl-6-(2-methylimidazolyl)(4-hydroimidazo[1,2-a]-pyrazin-8-yl)]amine

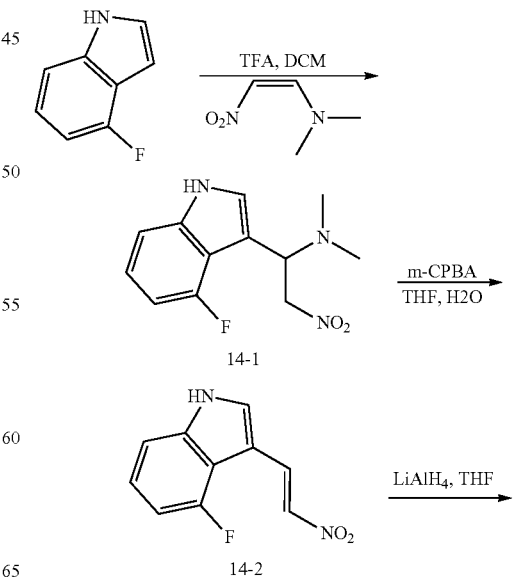

49
-continued

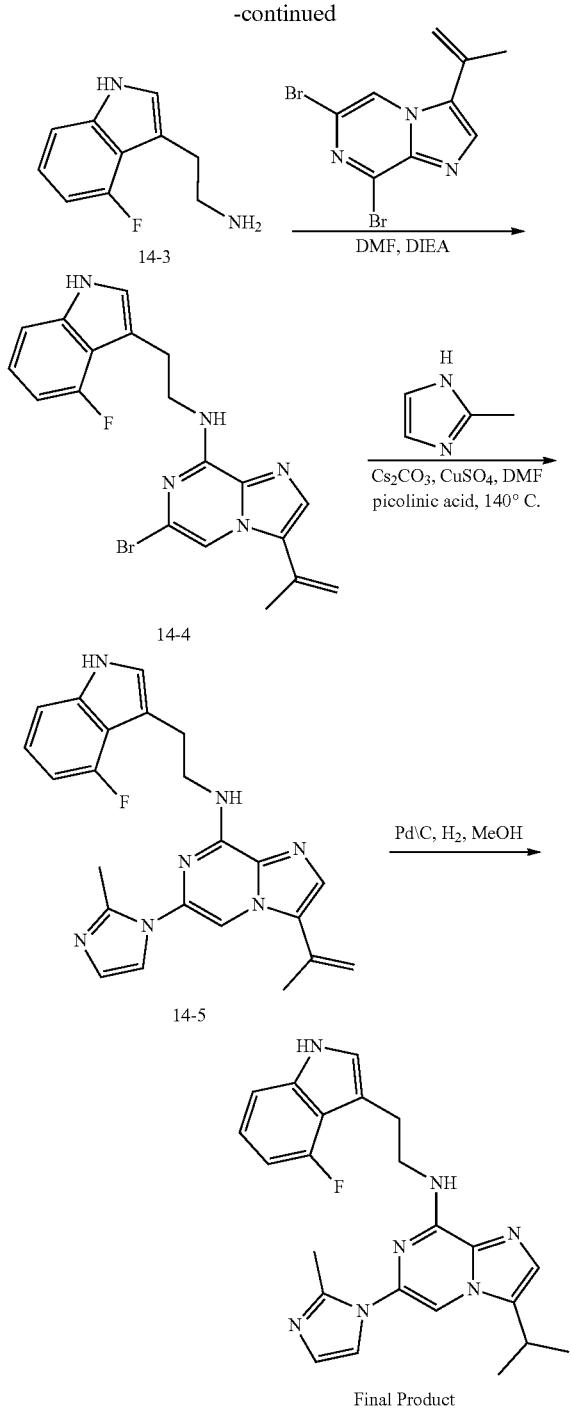

Step 1

Into a 50-mL 3-necked round-bottom flask, was placed N,N-dimethyl-2-nitroethenamine (1.3 g, 11.20 mmol, 1.20 equiv), and trifluoroacetic acid (12 mL), followed by the addition of 4-fluoro-1H-indole (1 g, 7.40 mmol, 1.00 equiv) dropwise with stirring. Dichloromethane (9 mL) was added and the resulting solution was stirred for 3 h at room temperature. The reaction mixture was concentrated under vacuum. Purification by flash chromatography (silica gel column with dichloromethane/methanol (200/1)) provided 1.8 g (97%) of 14-1 as a yellow solid.

Step 2

Into a 50-mL 3-necked round-bottom flask, was placed 14-1 (1.74 g, 6.93 mmol, 1.00 equiv), tetrahydrofuran (20 mL), water (5 mL), and m-CPBA (3.10 g, 17.96 mmol, 2.00 equiv). The resulting solution was stirred for 2 h at room temperature and then concentrated under vacuum. Purification by flash chromatography (dichloromethane/methanol (200/1)) provided 1.02 g (71%) of 14-2 as a yellow solid.

Step 3

Into a 50-mL 3-necked round-bottom flask purged and maintained with an inert atmosphere of nitrogen, was placed 14-2 (650 mg, 3.15 mmol, 1.00 equiv) in tetrahydrofuran (6.5 mL). This was followed by the addition of LiAlH$_4$ (599.5 mg, 15.80 mmol, 5.00 equiv) with stirring at 0° C. The resulting solution was stirred for 4 h at room temperature and then quenched with water/ice. The solids were filtered out. Purification by Prep-TLC (dichloromethane/methanol (10/1)) provided 350 mg (62%) of 14-3 as a white solid.

Step 4

Into a 8-mL vial purged and maintained with an inert atmosphere of nitrogen, was placed 5-2 (200 mg, 0.63 mmol, 1.00 equiv), 2-(4-fluoro-1H-indol-3-yl) ethan-1-amine (140 mg, 0.79 mmol, 1.00 equiv), N,N-dimethylformamide (2 mL), and DIEA (244 mg, 1.89 mmol, 3.00 equiv). The resulting solution was stirred overnight at 30° C. The resulting solution was extracted with 10 mL of ethyl acetate and the organic layers combined. The resulting mixture was washed with water. Purification by Prep-TLC (dichloromethane/methanol (30/1)) provided 150 mg (57%) of 14-4 as a white solid.

Step 5

Into a 8-mL vial purged and maintained with an inert atmosphere of nitrogen, was placed 14-4 (150 mg, 0.36 mmol, 1.00 equiv), N,N-dimethylformamide (2 mL), picolinic acid (153 mg, 2.30 equiv), 2-methyl-1H-imidazole (600 mg, 7.31 mmol, 20.00 equiv), Cs$_2$CO$_3$ (360 mg, 1.10 mmol, 3.00 equiv), and CuSO$_4$ (210 mg, 3.50 equiv). The resulting solution was stirred overnight at 140° C. The resulting solution was extracted with ethyl acetate and the organic layers combined. Purification by Prep-TLC (dichloromethane/methanol (20/1)) provided 92 mg (61%) of 14-5 as a white solid.

Step 6

Into a 50-mL round-bottom flask purged and maintained with an inert atmosphere of nitrogen, was placed 14-5 (92 mg, 0.22 mmol, 1.00 equiv), methanol (2 mL), and Pd/C (18 mg). H$_2$(g) was passed introduced and the resulting solution was stirred for 1 h at room temperature. The solids were filtered out and the resulting mixture was concentrated under vacuum. Purification by Prep-HPLC (Column, XBridge C18 OBD Prep Column, 100 mm, 5 um, 19 mm×250 mm; mobile phase, water (10 mmol/L NH$_4$HCO$_3$) and ACN (44.0% ACN up to 68.0% in 7 min); Detector, UV 254/220 nm) provided 5.9 mg (6%) of final product as a white solid. LCMS-PH (ES, m/z): [M+H]$^+$ 418; H-NMR (300 MHz, DMSO, ppm): δ 1.30-1.32 (d, 6H), 2.50 (s, 3H), 3.12-3.17 (t, 2H), 3.27-3.32 (t, 1H), 3.75-3.81 (m, 2H), 6.66-6.72 (m, 1H), 6.85-6.86 (d, 1H), 6.97-7.04 (m, 1H), 7.15-7.19 (m, 2H), 7.33-7.39 (m, 2H), 7.84-7.89 (m, 2H), 11.09 (s, 1H).

Example 15

Synthesis of [3-isopropyl-6-(2-methylimidazolyl)(4-hydroimidazo[1,2-a]pyrazin-8-yl)](2-pyrrolo[3,2-b]pyridin-3-ylethyl)amine

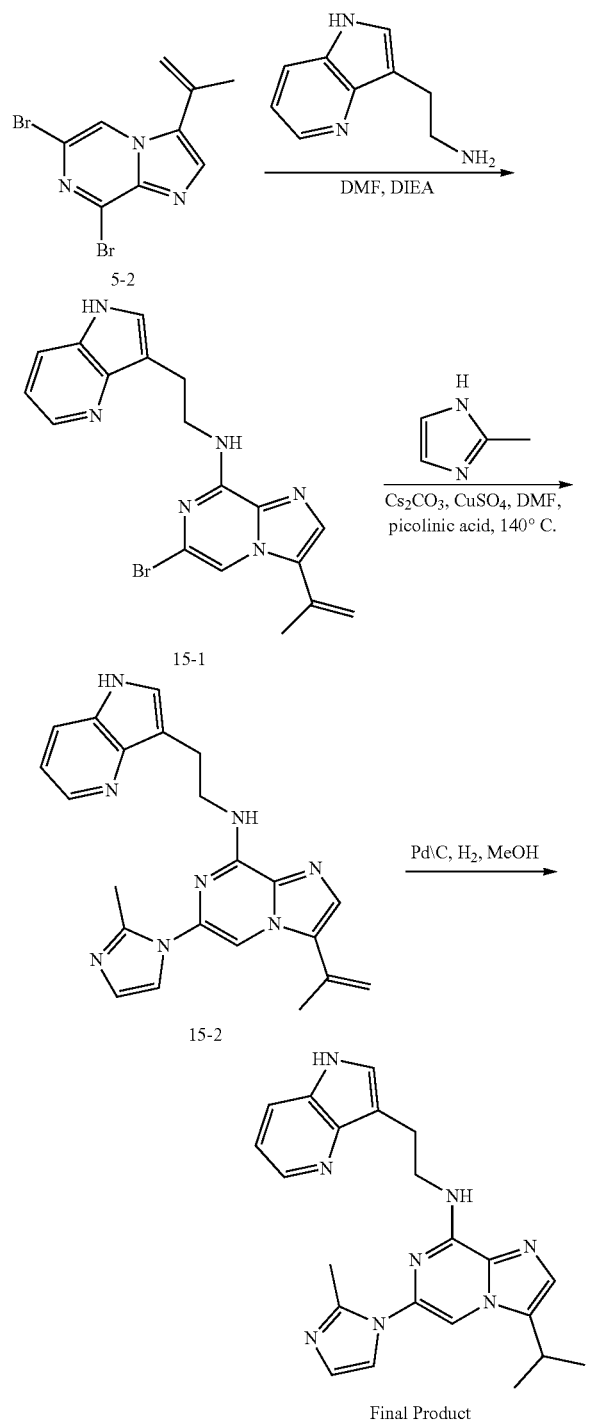

Step 1

Into a 8-mL sealed tube, was placed 5-2 (300 mg, 0.95 mmol, 1.00 equiv), 2-[1H-pyrrolo[3,2-b]pyridin-3-yl]ethan-1-amine (152 mg, 0.94 mmol, 1.00 equiv), DIEA (488 mg, 2.41 mmol, 4.00 equiv), and N,N-dimethylformamide (0.3 mL). The resulting solution was stirred overnight at 30,° C. and then diluted with water. The resulting solution was extracted with ethyl acetate and the organic layers combined. Purification by Prep-TLC (ethyl acetate/petroleum ether (2:3)) provided 180 mg (48%) of 15-1 as a yellow solid.

Step 2

Into a 8-mL sealed tube, was placed 5-1 (180 mg, 0.45 mmol, 1.00 equiv), 2-methyl-1H-imidazole (743 mg, 9.05 mmol, 20.00 equiv), pyridine-2-carboxylic acid (128 mg, 1.04 mmol, 2.30 equiv), $Cs_2CO_3$ (443 mg, 1.36 mmol, 3.00 equiv), N,N-dimethylformamide (2 mL), and $CuSO_4$ (252 mg, 1.58 mmol, 3.50 equiv). The resulting solution was stirred overnight at 140° C. in an oil bath and then diluted with 20 mL of water. The resulting solution was extracted with dichloromethane and the organic layers combined. Purification by Prep-TLC (dichloromethane/methanol (18:1)) provided 90 mg (50%) of 15-2 as a yellow solid.

Step 3

Into a 50-mL round-bottom flask, was placed 15-2 (90 mg, 0.23 mmol, 1.00 equiv.), tetrahydrofuran (2 mL), methanol (2 mL), and Pd/C (18 mg) and $H_2(g)$ was introduced into the solution. The resulting solution was stirred overnight at room temperature and then the solids were filtered out. Purification by Prep-TLC (dichloromethane/methanol (18:1)) provided 49.9 mg (55%) of final product as a white solid. LCMS (ES, m/z): [M+H]⁺ 401; H-NMR (DMSO, 400 MHz, ppm): δ 1.30-1.32 (d, 6H), 2.45 (s, 3H), 3.12-3.18 (m, 2H), 3.29-3.34 (m, 1H), 3.80-3.84 (m, 2H), 6.87 (s, 1H), 7.07-7.11 (m, 1H), 7.38-7.40 (t, 2H), 7.49-7.50 (d, 1H). 7.70-7.73 (m, 1H), 7.85 (s, 1H), 8.20-8.22 (t, 1H), 8.32-8.33 (d, 1H), 11.05 (s, 1H).

Example 16

Synthesis of [3-isopropyl-6-(2-methylimidazolyl)(4-hydroimidazo[1,2-a]pyrazin-8-yl)](2-pyrrolo[2,3-b]pyridin-3-ylethyl)amine

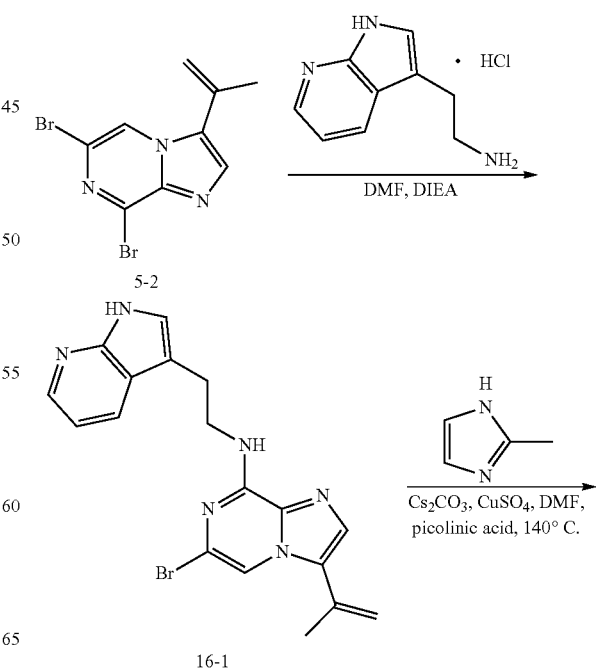

-continued

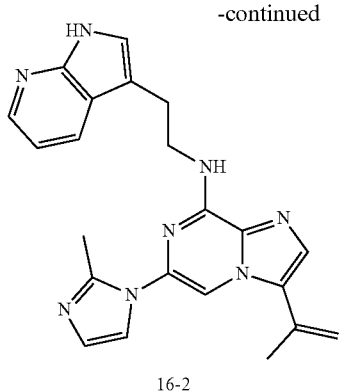

16-2

Pd\C, H₂, MeOH

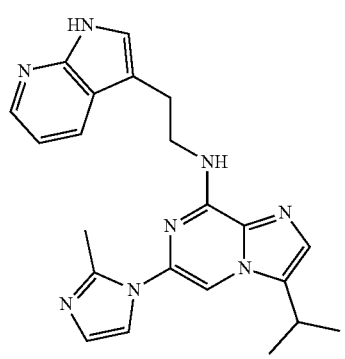

Final Product

The final product was prepared by following the synthetic scheme above and using methods described in preceding examples. LCMS (ES, m/z): [M+H]⁺ 401; H-NMR (DMSO, 400 MHz, ppm): δ 1.31-1.32 (d, 6H), 2.41 (s, 3H), 3.02-3.06 (t, 2H), 3.27-3.33 (m, 1H), 3.71-3.76 (m, 2H), 6.90-6.94 (m, 1H), 6.96-6.97 (m, 1H), 7.31 (d, 2H) 7.38-7.40 (t, 2H), 7.88 (s, 1H). 7.97-8.16 (m, 2H), 8.16-8.18 (d, 1H), 11.33 (s, 1H).

Example 17a and 17b

Synthesis of R)-2-indol-3-yl-isopropyl)[3-isopropyl-6-(2-methylimidazolyl)(4-hydroimidazo[1,2-a]pyrazin-8-yl)]amine and ((1S)-2-indol-3-yl-isopropyl)[3-isopropyl-6-(2-methylimidazolyl)(4-hydroimidazo[1,2-a]-pyrazin-8-yl)]amine

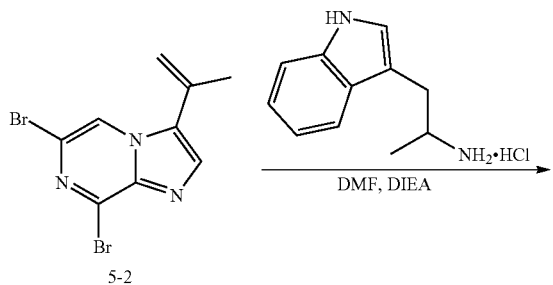

5-2

DMF, DIEA

-continued

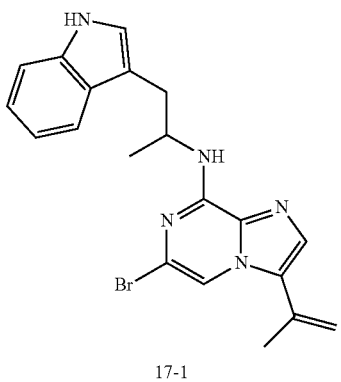

17-1

Cs₂CO₃, CuSO₄, DMF, picolinic acid

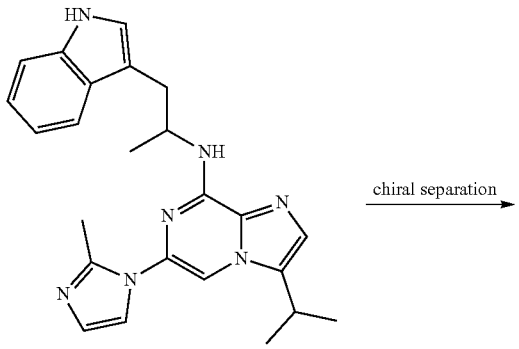

17-2

Pd\C, H₂, MeOH, rt

Final Product chiral separation

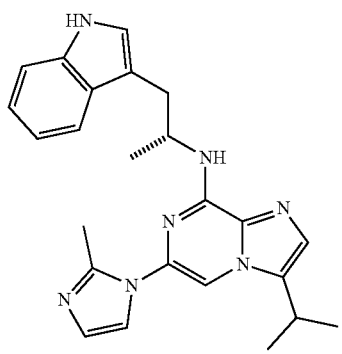

Final Product-a

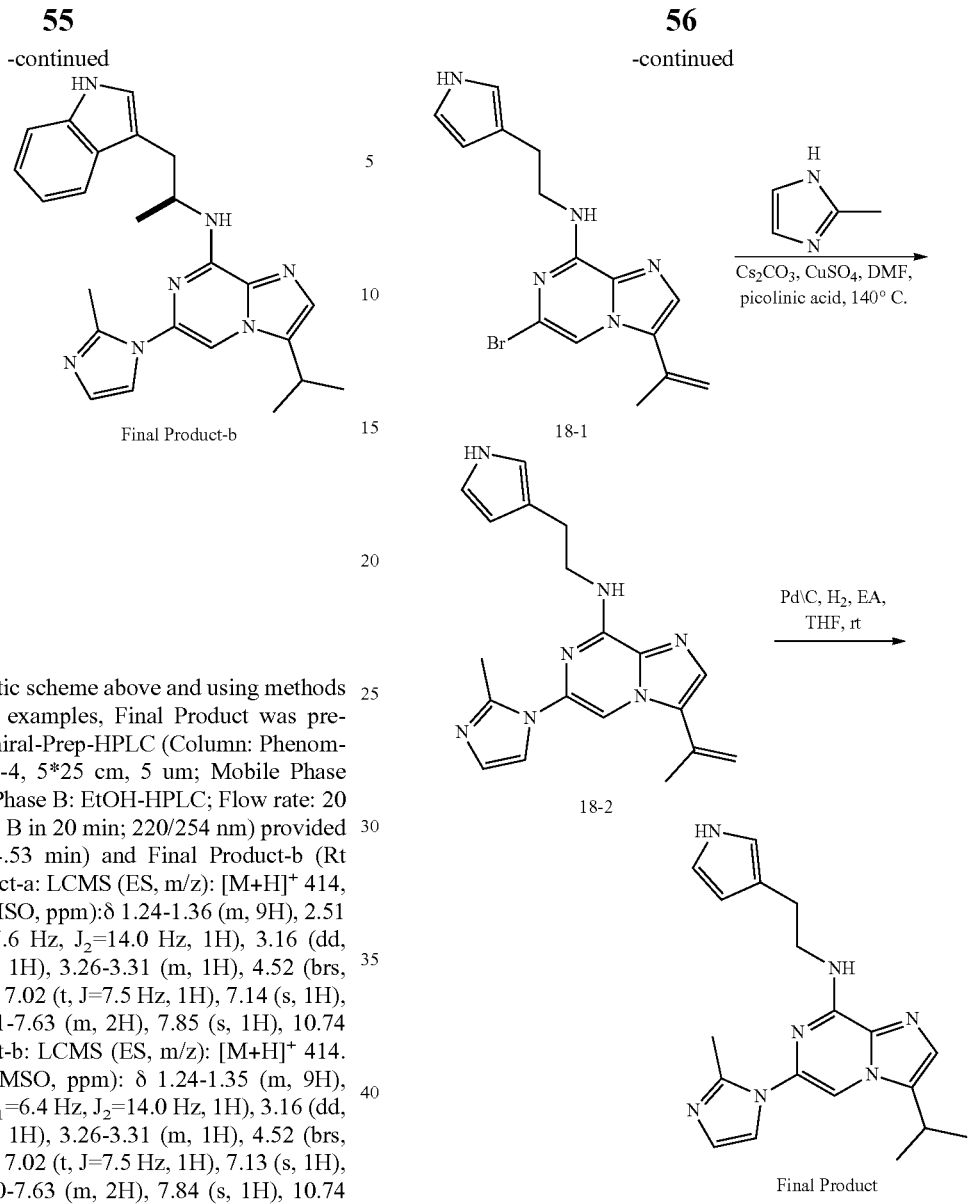

Step 1

Following the synthetic scheme above and using methods described in preceding examples, Final Product was prepared. Separation by Chiral-Prep-HPLC (Column: Phenomenex Lux 5u Cellulose-4, 5*25 cm, 5 um; Mobile Phase A:Hex-HPLC, Mobile Phase B: EtOH-HPLC; Flow rate: 20 mL/min; Gradient: 15% B in 20 min; 220/254 nm) provided Final Product-a (Rt 14.53 min) and Final Product-b (Rt 16.44 min). Final Product-a: LCMS (ES, m/z): [M+H]$^+$ 414, H-NMR (400 MHz, DMSO, ppm):δ 1.24-1.36 (m, 9H), 2.51 (s, 3H), 2.85 (dd, $J_1$=7.6 Hz, $J_2$=14.0 Hz, 1H), 3.16 (dd, $J_1$=6.4 Hz, $J_2$=14.0 Hz, 1H), 3.26-3.31 (m, 1H), 4.52 (brs, 1H), 6.85-6.89 (m, 2H), 7.02 (t, J=7.5 Hz, 1H), 7.14 (s, 1H), 7.28-7.38 (m, 3H), 7.61-7.63 (m, 2H), 7.85 (s, 1H), 10.74 (brs, 1H). Final Product-b: LCMS (ES, m/z): [M+H]$^+$ 414. H-NMR (400 MHz, DMSO, ppm): δ 1.24-1.35 (m, 9H), 2.38 (s, 3H), 2.84 (dd, $J_1$=6.4 Hz, $J_2$=14.0 Hz, 1H), 3.16 (dd, $J_1$=6.4 Hz, $J_2$=14.0 Hz, 1H), 3.26-3.31 (m, 1H), 4.52 (brs, 1H), 6.85-6.89 (m, 2H), 7.02 (t, J=7.5 Hz, 1H), 7.13 (s, 1H), 7.28-7.38 (m, 3H), 7.60-7.63 (m, 2H), 7.84 (s, 1H), 10.74 (brs, 1H).

Example 18

Synthesis of [3-isopropyl-6-(2-methylimidazolyl)(4-hydroimidazo[1,2-a]pyrazin-8-yl)](2-pyrrol-3-yl-ethyl)amine

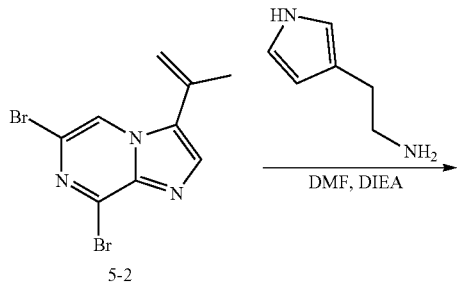

Following the synthetic scheme above and using methods described in preceding examples, Final Product was prepared. LC-MS (ES, m/z): [M+H]$^+$ 350; H-NMR (400 MHz, DMSO, ppm): δ 1.30-1.32 (d, 6H), 2.47 (s, 3H), 2.73-2.77 (t, 2H), 3.27-3.33 (m, 1H), 3.58-3.63 (m, 2H), 5.92-5.93 (d, 1H), 6.59-6.65 (d, 2H), 6.89 (s, 1H), 7.38-7.41 (m, 2H), 7.76-7.79 (m, 1H), 7.86 (s, 1H), 10.50 (s, 1H).

Example 19

Synthesis of 1-(2-{[6-(5-fluoro(3-pyridyl)-3-isopropyl-4-hydroimidazo[1,2-a]pyrazin-8-yl]-amino}ethyl)-3-hydrobenzimidazol-2-one

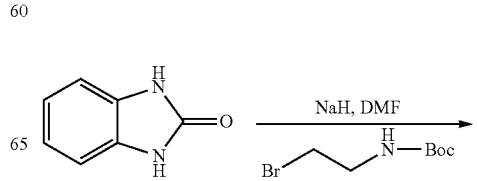

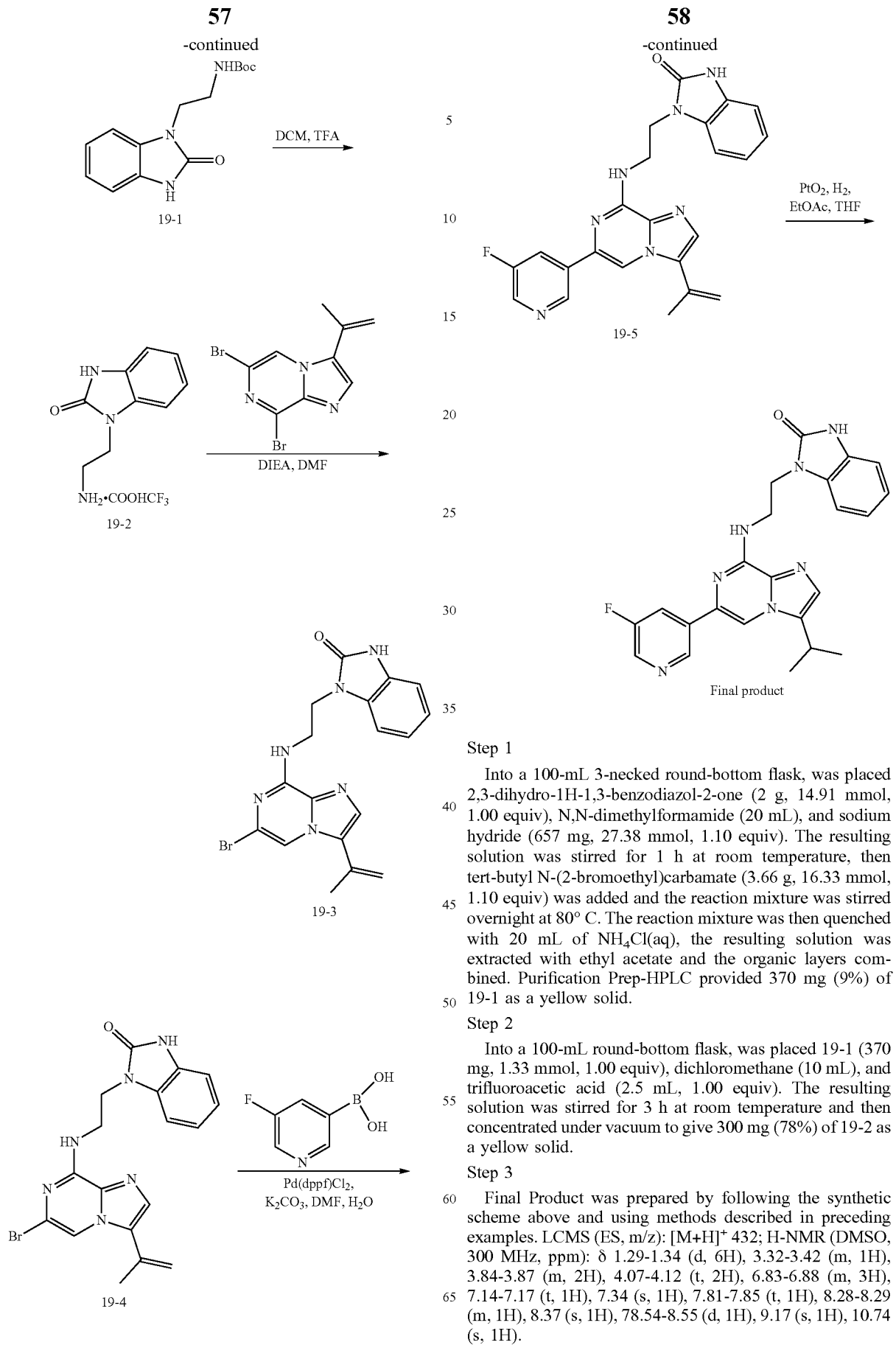

Step 1

Into a 100-mL 3-necked round-bottom flask, was placed 2,3-dihydro-1H-1,3-benzodiazol-2-one (2 g, 14.91 mmol, 1.00 equiv), N,N-dimethylformamide (20 mL), and sodium hydride (657 mg, 27.38 mmol, 1.10 equiv). The resulting solution was stirred for 1 h at room temperature, then tert-butyl N-(2-bromoethyl)carbamate (3.66 g, 16.33 mmol, 1.10 equiv) was added and the reaction mixture was stirred overnight at 80° C. The reaction mixture was then quenched with 20 mL of NH$_4$Cl(aq), the resulting solution was extracted with ethyl acetate and the organic layers combined. Purification Prep-HPLC provided 370 mg (9%) of 19-1 as a yellow solid.

Step 2

Into a 100-mL round-bottom flask, was placed 19-1 (370 mg, 1.33 mmol, 1.00 equiv), dichloromethane (10 mL), and trifluoroacetic acid (2.5 mL, 1.00 equiv). The resulting solution was stirred for 3 h at room temperature and then concentrated under vacuum to give 300 mg (78%) of 19-2 as a yellow solid.

Step 3

Final Product was prepared by following the synthetic scheme above and using methods described in preceding examples. LCMS (ES, m/z): [M+H]$^+$ 432; H-NMR (DMSO, 300 MHz, ppm): δ 1.29-1.34 (d, 6H), 3.32-3.42 (m, 1H), 3.84-3.87 (m, 2H), 4.07-4.12 (t, 2H), 6.83-6.88 (m, 3H), 7.14-7.17 (t, 1H), 7.34 (s, 1H), 7.81-7.85 (t, 1H), 8.28-8.29 (m, 1H), 8.37 (s, 1H), 78.54-8.55 (d, 1H), 9.17 (s, 1H), 10.74 (s, 1H).

Example 20

Synthesis of (2-(1H-indazol-3-yl)ethyl)[6-(5-fluoro (3-pyridyl)-3-isopropyl(4-hydroimidazo[1,2-a]pyrazin-8-yl)]amine

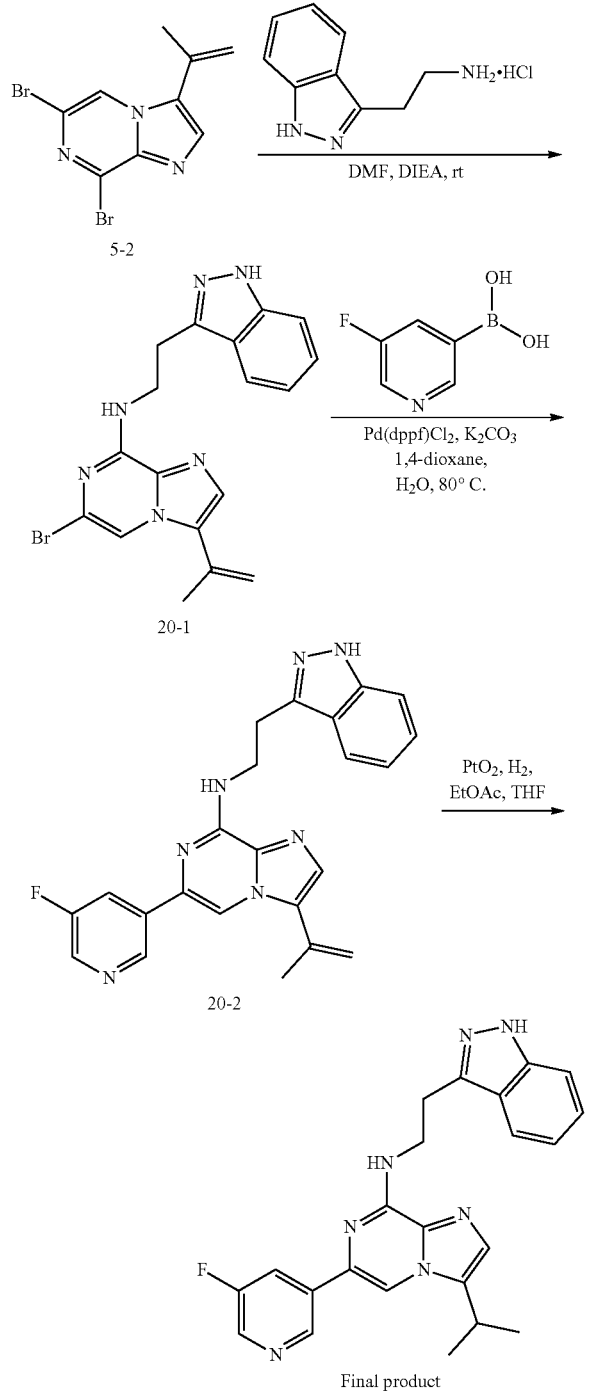

Final Product was prepared by following the synthetic scheme above and using methods described in preceding examples. LCMS (ES, m/z): [M+H]⁺ 416; H-NMR (300 MHz, DMSO, ppm): δ 1.34-1.36 (d, 6H), 3.31-3.33 (m, 1H), 3.36-3.40 (m, 1H), 3.42-3.47 (m, 1H), 3.94-4.01 (m, 2H), 7.03-7.08 (t, 1H), 7.30-7.37 (m, 2H), 7.45-7.48 (d, 1H), 7.78-7.83 (m, 2H), 8.30-8.37 (m, 1H), 8.42 (s, 1H), 8.56-8.57 (d, 1H), 9.22 (s, 1H), 12.74 (s, 1H).

Example 21

Synthesis of 2-(6-(5-fluoro-(3-pyridyl))-8-{[2-(4-fluoroindol-3-yl)ethyl]amino}-4-hydroimidazo[1,2-a]pyrazin-3-yl)propan-1-ol

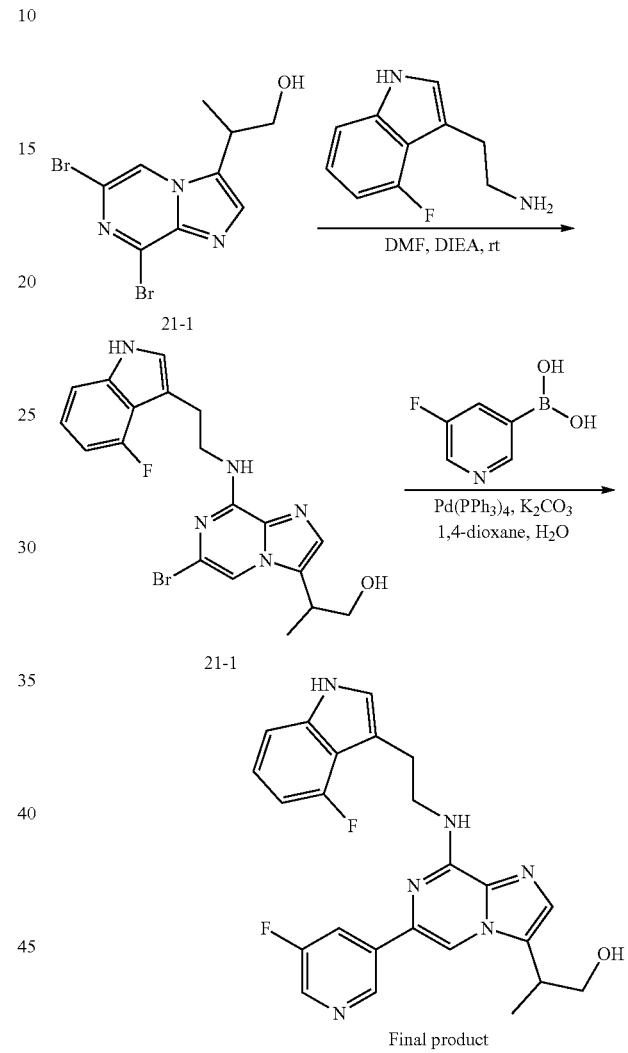

Step 1

To a stirred solution 6,8-dibromo-3-(prop-1-en-2-yl)imidazo[1,2-a]pyrazine (500 mg, 1.58 mmol, 1 equiv) in THF (5 mL) were added BH₃. THF (7.89 mL, 7.9 mol, 5 equiv, 1M). The resulting mixture was stirred for 1 h at room temperature. To the above mixture was added NaOH (1.18 mL, 4M), H₂O₂ (1.067 mL, 11.04 mmol, 7 equiv, 35.5%). The resulting mixture was stirred for additional 4 h at room temperature. The resulting mixture was diluted with H₂O (20 mL). The resulting mixture was extracted with ethyl acetate (2×mL). The combined organic layer was concentrated under reduced pressure. Purification by Prep-TLC (DCM/MeOH=30:1) provided 21-1 (12.1 mg, 2.29%) as a white solid. LCMS (ES, m/z): [M+H]⁺ 336; H-NMR (DMSO, 400 MHz, ppm): δ 1.29-1.31 (d, 3H), 3.39-3.54 (m, 2H), 3.64-3.69 (m, 1H), 4.82-4.84 (t, 1H), 7.79 (s, 1H), 8.89 (s, 1H).

Step 2

Final Product was prepared by following the synthetic scheme above and using methods described in preceding examples LCMS (ES, m/z): [M+H]⁺449; H-NMR (400 MHz, DMSO, ppm): δ 1.23-1.41 (s, 3H), 3.16-3.24 (m, 2H), 3.41-3.43 (m, 1H), 3.56-3.65 (m, 2H), 3.89-3.90 (m, 2H), 4.82-4.85 (t, 1H), 6.68-6.73 (m, 1H), 6.98-7.03 (m, 1H), 7.14-7.16 (d, 1H), 7.21 (s, 1H), 7.35 (s, 1H), 7.65-7.68 (m, 1H), 8.28-8.31 (d, 1H), 8.43 (s, 1H), 8.53-8.54 (d, 1H), 9.18 (s, 1H).

Example 22

Synthesis of [2-(4,6-difluoroindol-3-yl)ethyl][3-isopropyl-6-(2-methylimidazolyl)(4-hydroimidazo[1,2-a]pyrazin-8-yl)]amine

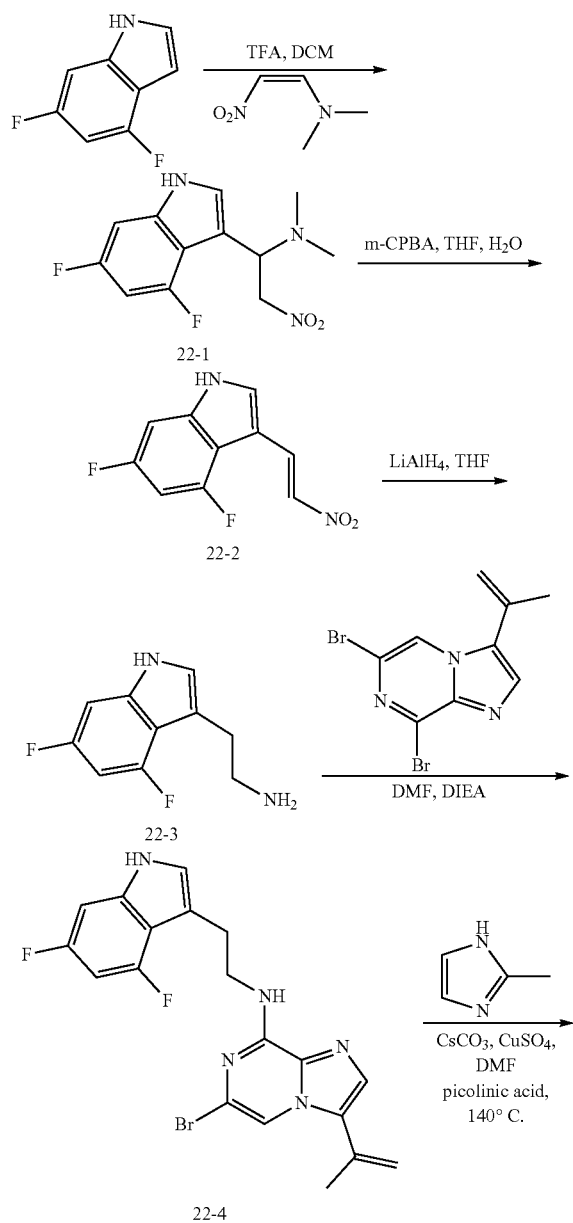

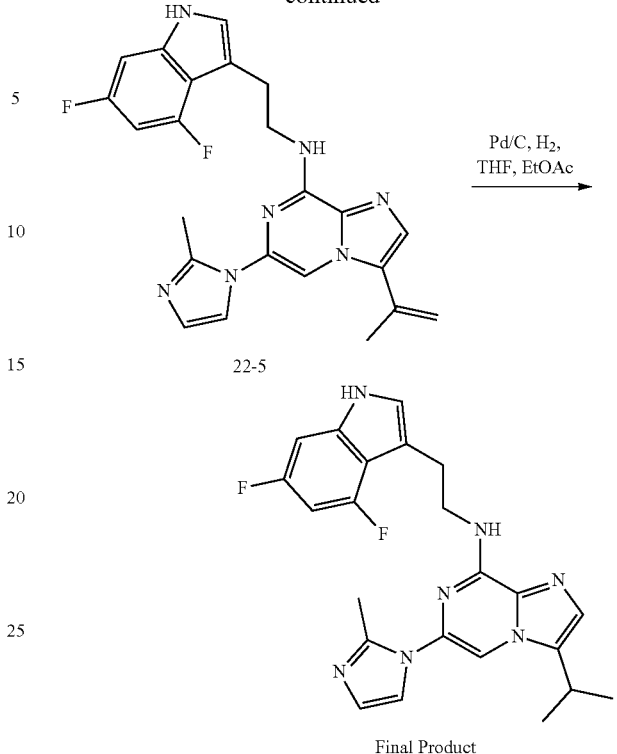

Step 1

Into a 50-mL 3-necked round-bottom flask under nitrogen atmosphere, was placed N,N-dimethyl-2-nitroethenamine (1.77 g, 15.24 mmol, 1.00 equiv), trifluoroacetic acid (15 mL), 4,6-difluoro-1H-indole (2 g, 13.06 mmol, 1.00 equiv), and dichloromethane (12 mL). The resulting solution was stirred for 4 h at room temperature and then concentrated under vacuum. Purification by flash chromatography (silica gel column with ethyl acetate/petroleum ether (1/20)) provided 1.2 g (34%) of 22-1 as a yellow solid.

Step 2

Into a 50-mL 3-necked round-bottom flask, was placed 22-1 (1.2 g, 4.46 mmol, 1.00 equiv), tetrahydrofuran (12 mL), water (3 mL), and m-CPBA (1.53 g, 8.87 mmol, 2.00 equiv). The resulting solution was stirred for 2 h at room temperature. The resulting solution was extracted with dichloromethane and the organic layers combined and concentrated under vacuum. Purification by flash chromatography (silica gel column with ethyl acetate/petroleum ether (1/10)) provided 430 mg (43%) of 22.2 as a yellow solid.

Step 3

Compound 22-2 (1.2 g, 5.35 mmol, 1 equiv.) was added to LiAlH₄ (1015.9 mg, 26.77 mmol, 5 equiv), in THF at room temperature under nitrogen atmosphere. The resulting mixture was stirred at room temperature overnight. The solids were filtered out. The resulting mixture was concentrated under vacuum and purified by Prep-TLC (DCM/MeOH (10/1)) to give 22-3 (420 mg, 39.99%) as a white solid.

Step 4

Final Product was prepared by following the synthetic scheme above and using methods described in preceding examples. LCMS (ES, m/z): [M+H]⁺ 436; H-NMR (300 MHz, DMSO, ppm): δ 1.28-1.32 (d, 6H), 2.50 (s, 3H), 3.09-3.14 (t, 2H), 3.25-3.38 (m, 1H), 3.73-3.80 (m, 2H), 6.68-6.76 (m, 1H), 6.86-6.87 (d, 1H), 6.96-7.00 (m, 1H), 7.17-7.18 (d, 1H), 7.33-7.34 (m, 1H), 7.37-7.39 (m, 1H), 7.84 (s, 1H), 7.87-7.91 (m, 1H), 11.16 (s, 1H).

Example 23

Synthesis of 3-({[3-isopropyl-6-(2-methylimidazolyl)-4-hydroimidazo[1,2-a]pyrazin-8-yl]amino}-methyl)benzamide

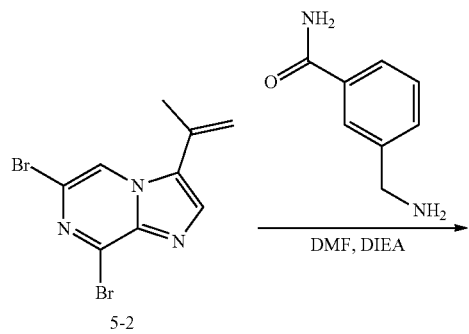

5-2

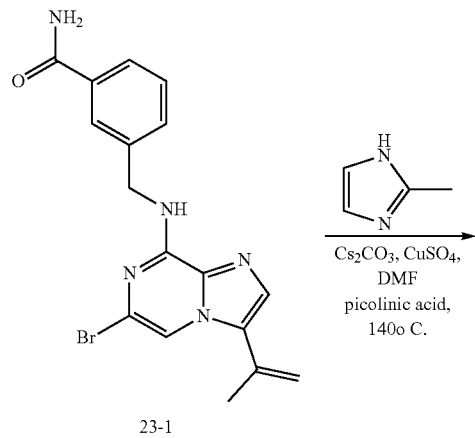

23-1

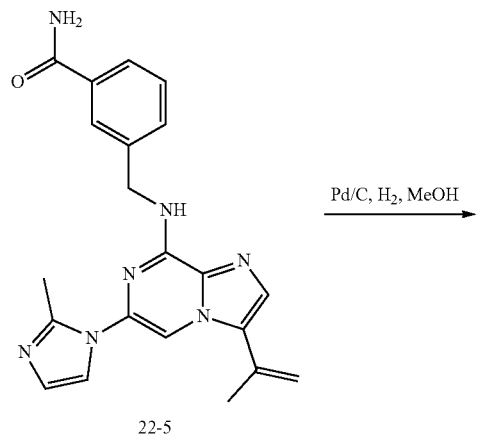

22-5

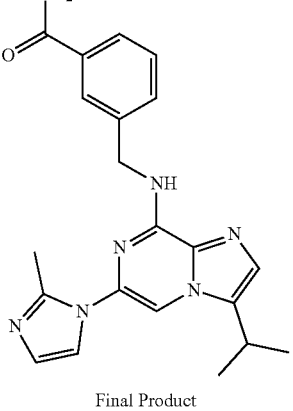

Final Product

Final Product was prepared by following the synthetic scheme above and using methods described in the examples. LCMS (ES, m/z): [M+H]$^+$ 390; H-NMR (DMSO, 300 MHz, ppm): δ 1.31-1.32 (d, 6H), 2.21 (s, 3H), 3.31-3.32 (m, 1H), 4.68-4.70 (d, 2H), 6.84 (s, 1H), 7.31-7.37 (m, 3H), 7.43 (s, 1H), 7.48-7.50 (d, 1H), 7.71-7.7.73 (d, 1H), 7.88-7.92 (m, 3H), 8.53-8.57 (t, 1H).

Example 24

Synthesis of [6-(5-fluoro(3-pyridyl)-3-isopropyl(4-hydroimidazo[1,2-a]pyrazin-8-yl)][2-(4-fluoroindol-3-yl)ethyl]amine

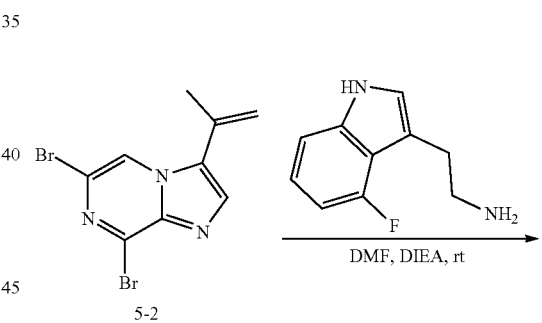

5-2

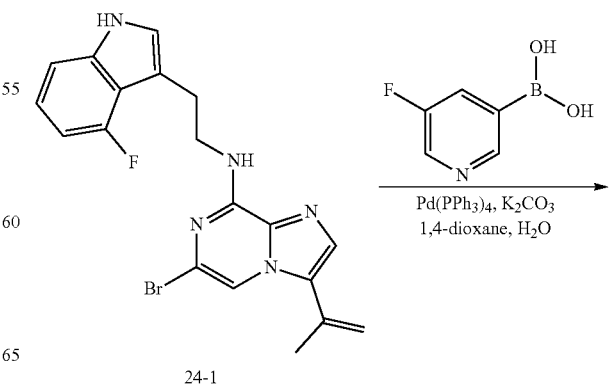

24-1

-continued

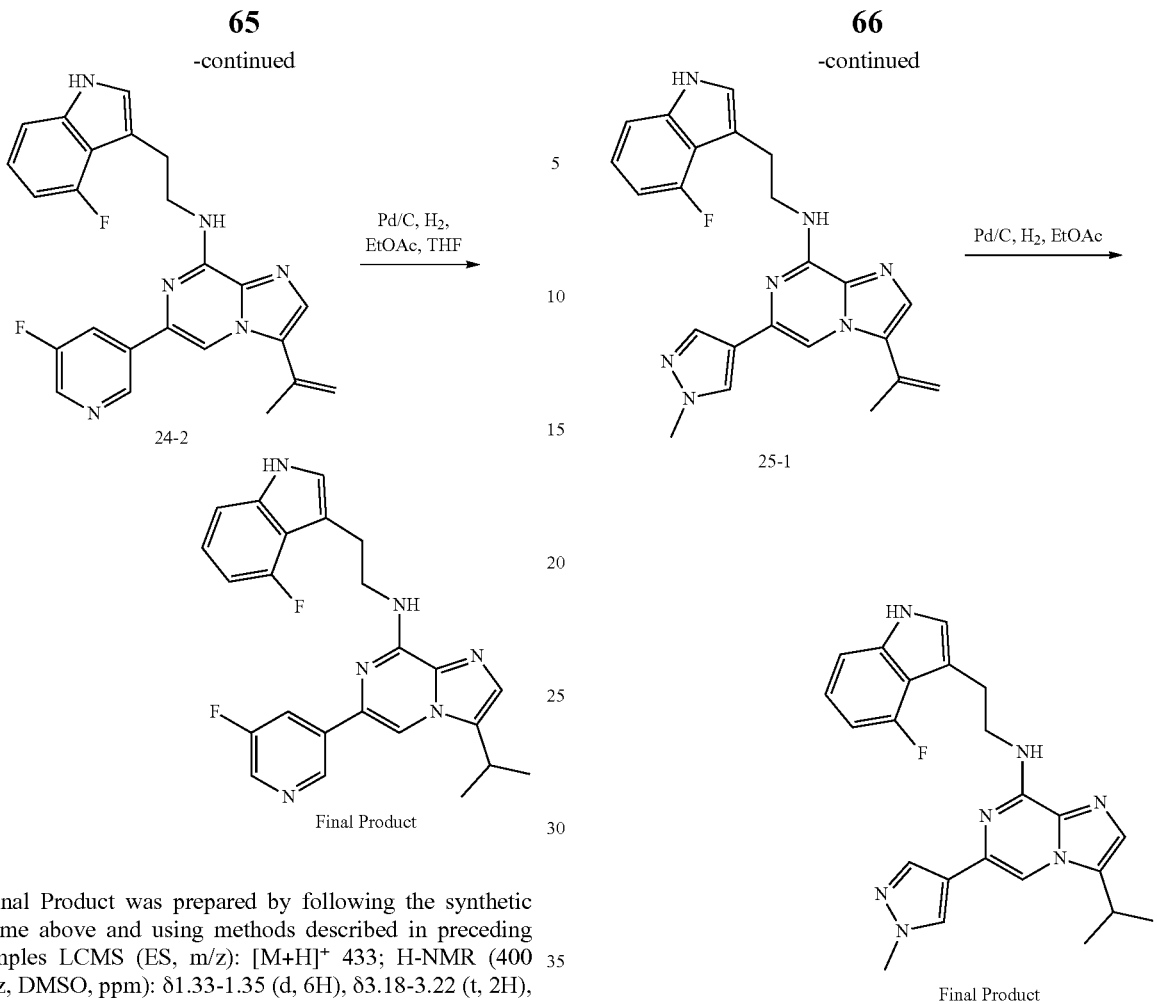

24-2

Final Product

Final Product was prepared by following the synthetic scheme above and using methods described in preceding examples LCMS (ES, m/z): [M+H]⁺ 433; H-NMR (400 MHz, DMSO, ppm): δ1.33-1.35 (d, 6H), δ3.18-3.22 (t, 2H), δ3.40-3.45 (m, 1H), δ3.87-3.92 (m, 2H), δ6.66-6.73 (m, 1H), δ6.98-7.04 (m, 1H), δ7.15-7.17 (d, 1H), δ7.21-7.22 (d, 1H), δ7.35 (s, 1H), δ7.69-7.72 (t, 1H), δ8.31-8.35 (m, 1H), δ8.41 (s, 1H), δ8.54-8.55 (d, 1H), δ9.21 (s, 1H), δ11.14 (s, 1H).

Example 25

Synthesis of [2-(4-fluoroindol-3-yl)ethyl][3-isopropyl-6-(1-methylpyrazol-4-yl)(4-hydroimidazo[1,2-a]-pyrazin-8-yl)]amine

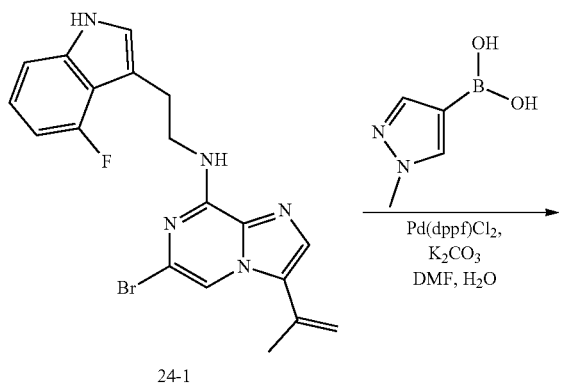

24-1

-continued 25-1

Final Product

Step 1

Into a 8-mL sealed tube, was placed 24-1 (300 mg, 0.72 mmol, 1.00 equiv), 1-methyl-4-(tetramethyl-1,3,2-dioxaborolan-2-yl)-1H-pyrazole (200 mg, 0.96 mmol, 1.33 equiv), potassium carbonate (300 mg, 2.17 mmol, 3.00 equiv), N,N-dimethylformamide (3 mL), water (0.5 mL), and Pd(dppf)Cl₂ (55 mg, 0.08 mmol, 0.10 equiv). The resulting solution was stirred overnight at 80° C. and then quenched with water. The resulting solution was extracted with ethyl acetate and the organic layers combined. Purification by Prep TLC (ethyl acetate/petroleum ether (1:1)) provided 150 mg (50%) of 25-1 as a off-white solid.

Step 2

Final Product was prepared by following the synthetic scheme above and using methods described in preceding examples LCMS (ES, m/z): [M+H]⁺ 418; H-NMR (DMSO, 400 MHz, ppm): δ 1.29-1.33 (dd, 6H), 3.15-3.19 (t, 2H), 3.25-3.33 (m, 1H), 3.82-3.87 (m, 5H), 6.70-6.75 (m, 1H), 7.01-7.05 (m, 1H), 7.16-7.18 (d, 1H), 7.23-7.25 (d, 1H), 7.32-7.35 (t, 1H), 7.88-7.89 (d, 1H), 7.93-7.94 (d, 1H), 8.02-8.04 (d, 1H), 11.10 (s, 1H).

Example 26

Synthesis of [2-(4-fluoroindol-3-yl)ethyl][6-(5-fluoro-6-methyl(3-pyridyl)-3-isopropyl(4-hydroimidazo[1,2-a]pyrazin-8-yl)]amine

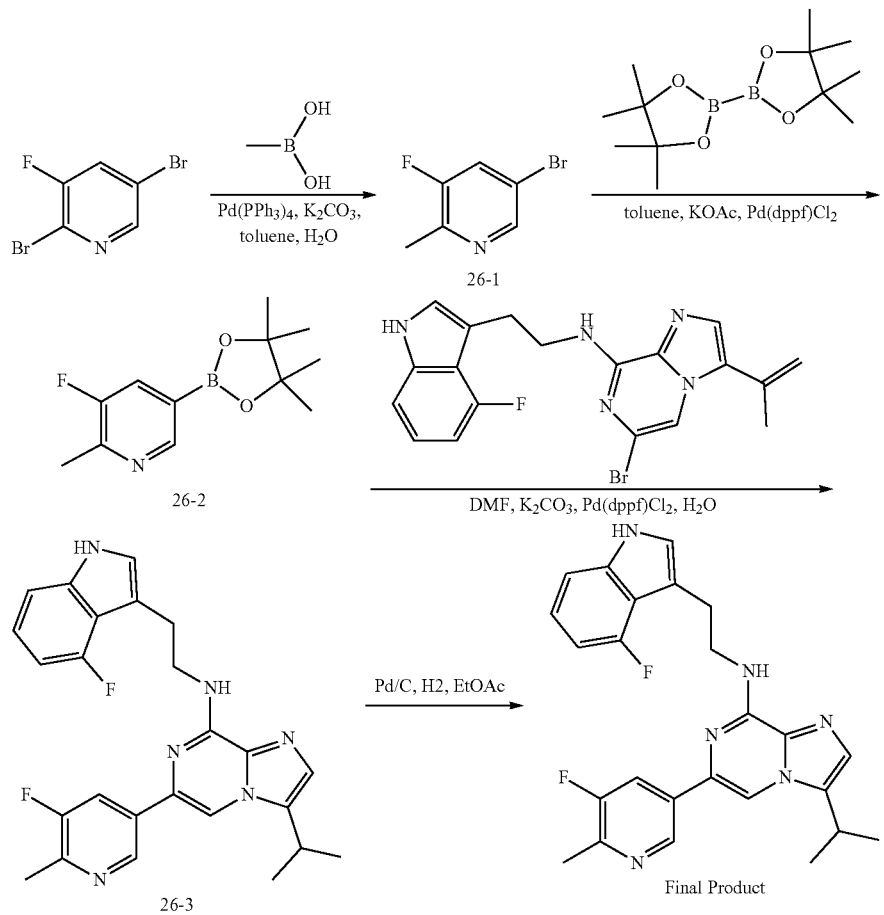

Step 1

Into a 250-mL 3-necked round-bottom flask, was placed 2,5-dibromo-3-fluoropyridine (5 g, 19.62 mmol, 1.00 equiv), methylboronic acid (8.3 g, 138.66 mmol, 7.00 equiv), potassium carbonate (10.96 g, 79.30 mmol, 4.00 equiv), toluene (150 mL), water (15 mL), and Pd(PPh$_3$)$_4$ (3.4 g, 2.94 mmol, 0.15 equiv). The resulting solution was stirred for 7 days at 60° C. The resulting mixture was concentrated under vacuum to give crude 26-1 in toluene (150 mL).

Step 2

Into a 250-mL 3-necked round-bottom flask, was placed 26-1 (150 mL toluene solution), 4,4,5,5-tetramethyl-2-(tetramethyl-1,3,2-dioxaborolan-2-yl)-1,3,2-dioxaborolane (4.44 g, 17.48 mmol, 1.10 equiv), KOAc (4.7 g, 47.89 mmol, 3.00 equiv), and Pd(dppf)Cl$_2$ (600 mg, 0.82 mmol, 0.05 equiv). The resulting solution was stirred overnight at 100° C. and then diluted with petroleum ether. The solids were filtered out. Purification by Prep TLC (ethyl acetate/petroleum ether (1:5)) provided 700 mg (19%) 26-2 as a yellow solid.

Step 3

Into a 8-mL sealed tube, was placed 24-1 (200 mg, 0.48 mmol, 1.00 equiv), 26-2 (230 mg, 0.97 mmol, 2.00 equiv), potassium carbonate (200 mg, 1.45 mmol, 3.00 equiv), N,N-dimethylformamide (4 mL), water (1 mL), and Pd(dppf)Cl$_2$ (40 mg, 0.05 mmol, 0.10 equiv). The resulting solution was stirred for 3 h at 80° C. and then quenched with water. The resulting solution was extracted with dichloromethane and the organic layers combined. Purification by Prep TLC (dichloromethane/methanol (10:1)) provided 70 mg (33%) of 26-3 as a off-white solid.

Step 4

Into a 50-mL round-bottom flask, was placed 26-3 (70 mg, 0.16 mmol, 1.00 equiv), Palladium on carbon (14 mg), and ethyl acetate (20 mL). H$_2$(g) was introduced and the resulting solution was stirred for 5 h at room temperature. The solids were filtered out. Purification by Prep. TLC (dichloromethane/methanol (10:1)) provided 9.5 mg (14%) of Final Product as a white solid. LCMS (ES, m/z): [M+H]$^+$ 447; H-NMR (DMSO, 400 MHz, ppm): δ 1.32-1.34 (d, 6H), 2.49 (s, 3H), 3.16-3.21 (t, 2H), 3.39-3.42 (m, 1H), 3.85-3.91 (m, 2H), 6.68-6.73 (m, 1H), 6.99-7.04 (m, 1H), 7.15-7.17 (d, 1H), 7.21 (d, 1H), 7.22-7.33 (d, 1H), 7.66-7.69 (t, 1H), 8.22-8.26 (m, 1H), 8.34 (s, 1H), 9.05 (s, 1H), 11.2 (s, 1H).

Example 27

Synthesis of [2-(4-fluoroindol-3-yl)ethyl][3-isopropyl-6-(2-methylpyrimidin-5-yl)(4-hydroimidazo[1,2-a]pyrazin-8-yl)]amine

Example 28

Synthesis of [6-(5-fluoro(3-pyridyl)-3-isopropyl(4-hydroimidazo[1,2-a]pyrazin-8-yl)](indol-4-ylmethyl)amine

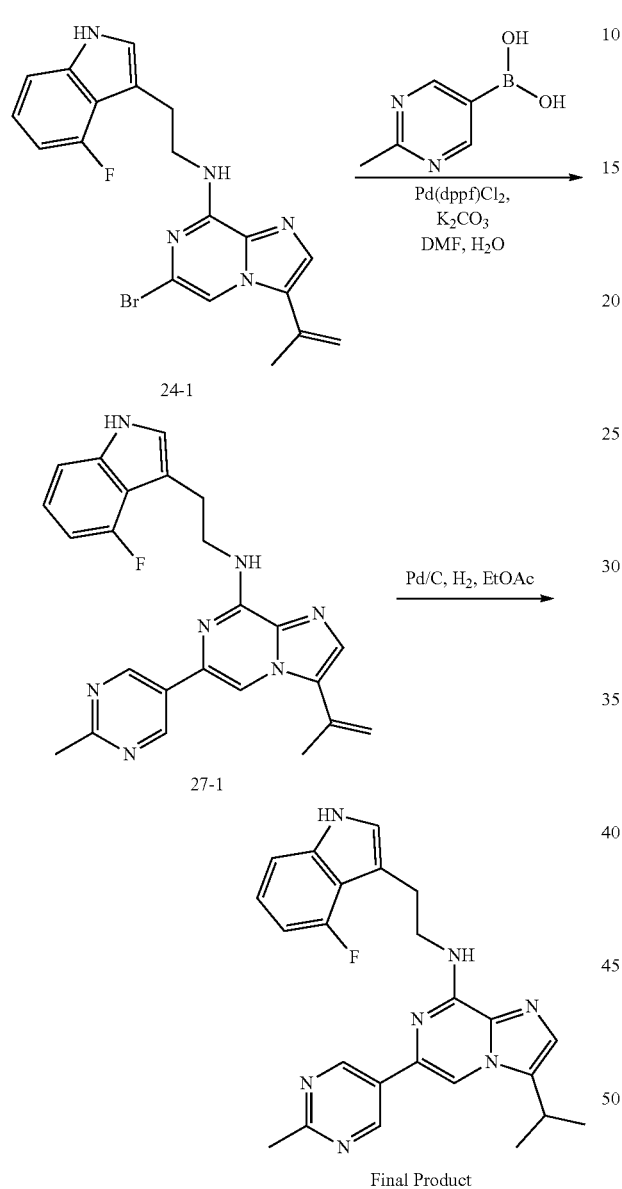

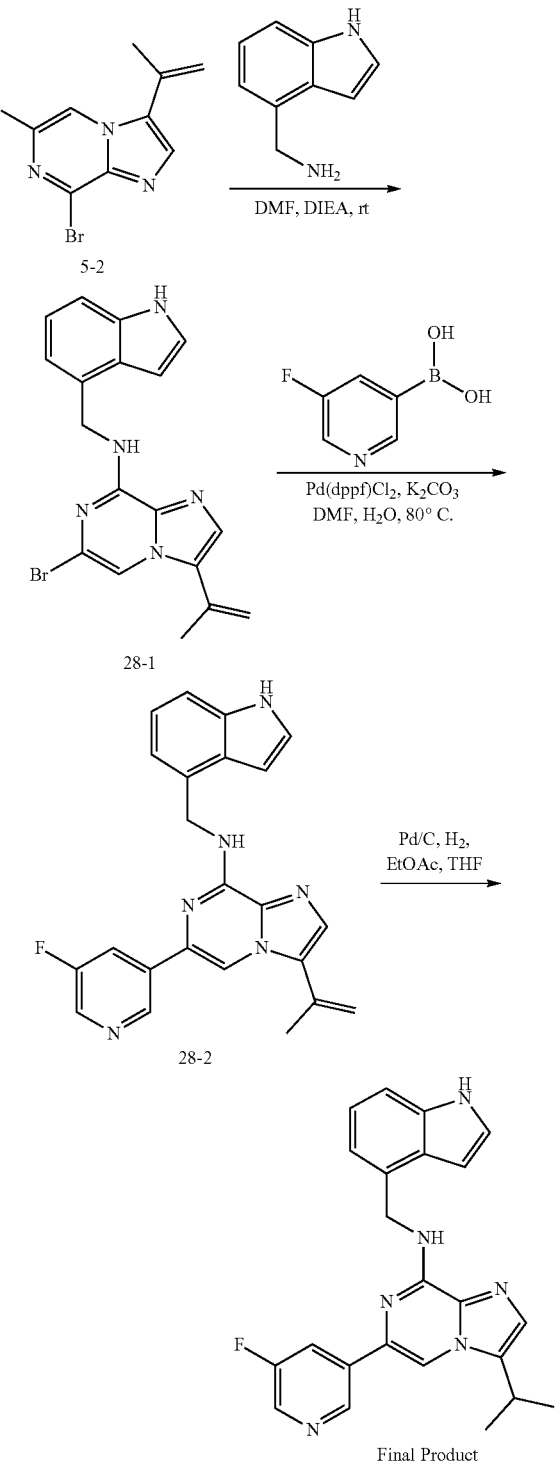

Final Product was prepared by following the synthetic scheme above and using methods described in preceding examples. LCMS (ES, m/z): [M+H]+ 430; H-NMR (DMSO, 400 MHz, ppm): δ 1.33-1.34 (d, 6H), 2.67-2.69 (d, 3H), 3.18-3.21 (t, 2H), 3.35-3.42 (m, 1H), 3.86-3.91 (m, 2H), 6.68-6.72 (m, 1H), 6.98-7.03 (m, 1H), 7.15-7.17 (m, 1H), 7.20-7.21 (d, 1H), 7.33 (s, 1H), 7.63-7.69 (m, 1H), 8.32-8.35 (d, 1H), 9.26-7.31 (d, 2H), 11.10 (s, 1H).

Final Product was prepared by following the synthetic scheme above and using methods described in preceding examples. LCMS (ES, m/z): [M+H]+ 401; H-NMR (300 MHz, DMSO-d6, ppm): δ 1.33 (s, 3H), 1.35 (s, 3H), 3.45-3.33 (m, 1H), 5.03-5.02 (d, 2H), 6.74 (s, 1H), 7.02-6.97 (m, 2H), 7.28-7.25 (d, 1H), 7.34-7.31 (d, 1H), 7.37 (s, 1H), 8.23-8.18 (m, 2H), 8.40 (s, 1H), 8.51-8.50 (d, 1H), 9.14 (s, 1H), 11.09 (s, 1H).

Example 29

Synthesis of [6-(5-fluoro(3-pyridyl)-3-isopropyl(4-hydroimidazo[1,2-a]pyrazin-8-yl)](2-indolylethyl)amine

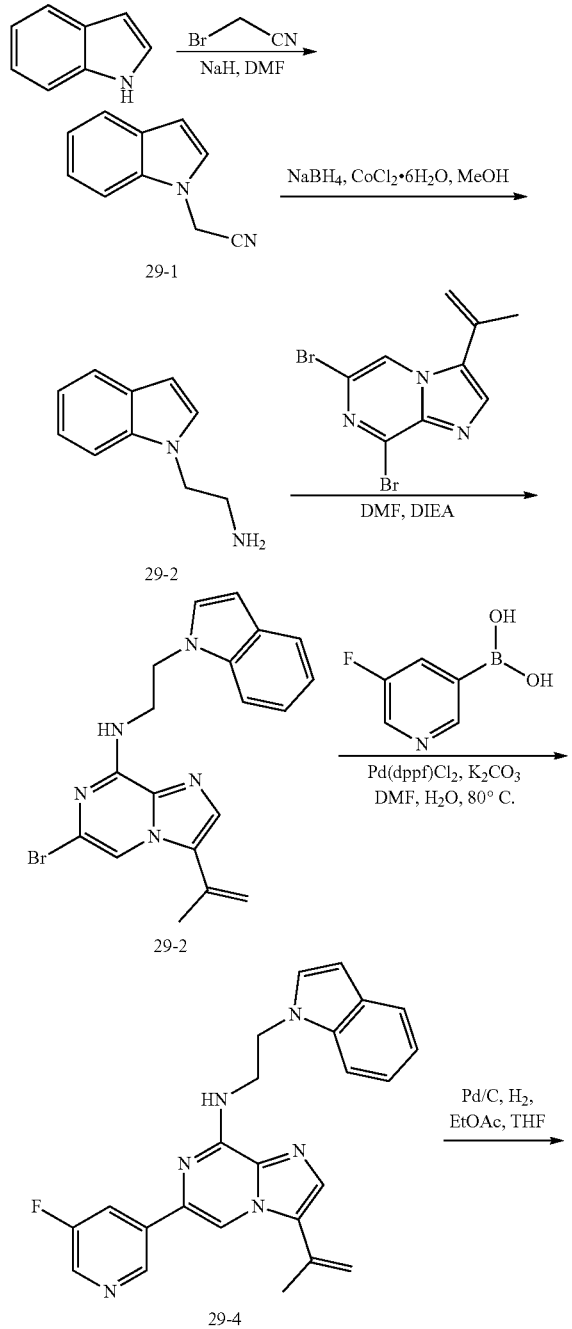

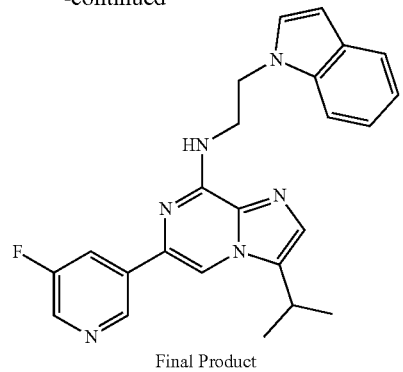

Final Product

Step 1

Into a 50-mL 3-necked round-bottom flask, was placed 1H-indole (1 g, 8.54 mmol, 1.00 equiv) and N,N-dimethylformamide (10 mL). Sodium hydride (380 mg, 15.83 mmol, 1.10 equiv), in portions, followed by addition of 2-bromoacetonitrile (2 g, 16.67 mmol, 2.00 equiv). The resulting solution was stirred overnight at 65° C. in an oil bath. The resulting solution was extracted with ethyl acetate and the organic layers combined and concentrated under vacuum. Purification by Prep-TLC (ethyl acetate/petroleum ether (1:1)) provided 300 mg (23%) of 29-1 as a white solid.

Step 2

Into a 25-mL round-bottom flask, was placed 29-1 (270 mg, 1.73 mmol, 1.00 equiv), methanol (3 mL), CoCl2.6H2O (819.9 mg, 2.00 equiv), and NaBH4 (657.7 mg, 17.39 mmol, 10.00 equiv). The resulting solution was stirred for 3 h at room temperature. The resulting solution was extracted with ethyl acetate and the organic layers combined and concentrated under vacuum. Purification by Prep-TLC (dichloromethane/methanol (10/1)) provided 170 mg (61%) of 29-2 as a white solid.

Step 3

Final Product was prepared by following the synthetic scheme above and using methods described in preceding examples. LCMS (ES, m/z): [M+H]+ 415; H-NMR (300 MHz, DMSO, ppm): δ 1.32-1.35 (d, 6H), 3.43-3.45 (m, 1H), 3.92-3.99 (m, 2H), 4.47-4.51 (t, 2H), 6.35 (s, 1H), 6.95-7.00 (m, 1H), 7.06-7.10 (m, 1H), 7.33-7.36 (t, 2H), 7.47-7.49 (d, 1H), 7.58-7.61 (d, 1H), 7.82-7.85 (t, 1H), 8.17-8.22 (m, 1H), 8.39 (s, 1H), 8.55-8.56 (d, 1H), 9.15 (s, 1H).

Example 30

Synthesis of (2-benzimidazolylethyl)[6-(5-fluoro(3-pyridyl))-3-isopropyl(4-hydroimidazo[1,2-a]pyrazin-8-yl)]amine

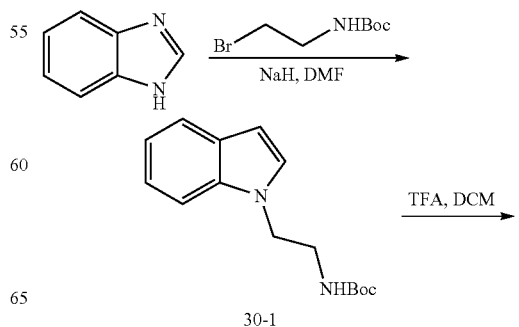

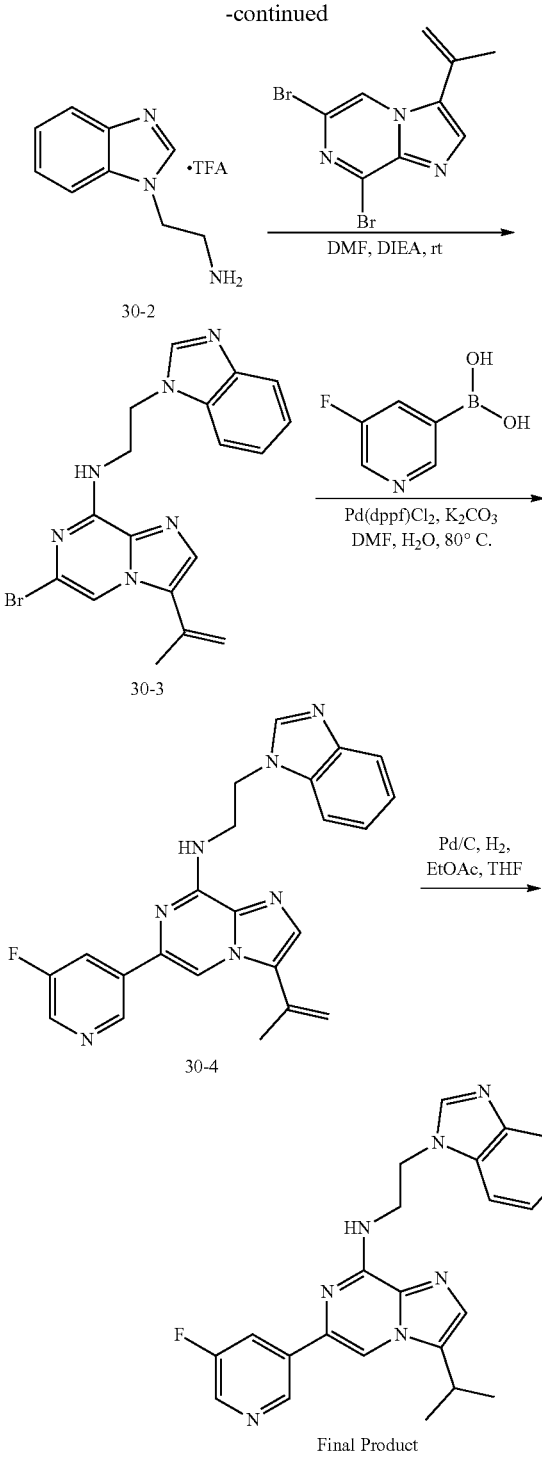

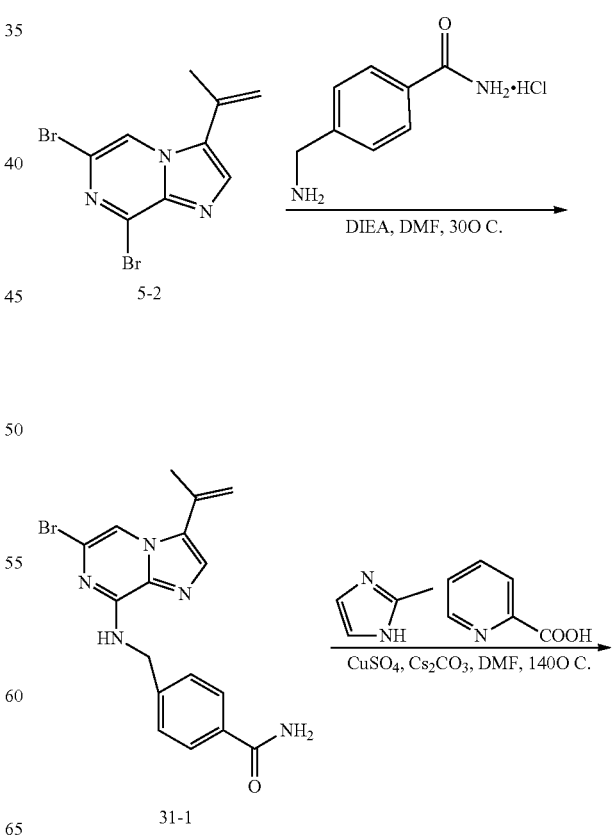

extracted with ethyl acetate and the organic layers combined. Purification by flash chromatography (silica gel column with ethyl acetate/petroleum ether (1:5)) provided 1.1 g (68%) of 30-1 as a white solid.

Step 2

Into a 10-mL round-bottom flask, was placed tert-butyl N-[2-(1H-1,3-benzodiazol-1-yl)ethyl]carbamate (30 mg, 0.11 mmol, 1.00 equiv), and $CF_3COOH$ (0.5 mL), dichloromethane (2 mL). The resulting solution was stirred for 12 h at room temperature. The resulting mixture was concentrated under vacuum to give 25.6 mg (81%) of 30-2 as a white solid.

Step 3

Final Product was prepared by following the synthetic scheme above and using methods described in preceding examples. LCMS (ES, m/z): $[M+H]^+$ 416; H-NMR (300 MHz, DMSO-$d_6$, ppm): δ 1.23 (s, 3H), 1.33 (s, 3H), 3.31-3.29 (m, 1H), 4.01-4.00 (m, 2H), 4.58 (t, 2H), 7.19-7.17 (d, 2H), 7.53-7.51 (d, 1H), 7.67-7.65 (d, 1H), 7.91-7.89 (t, 1H), 8.11-8.09 (m, 2H), 8.36 (s, 1H), 8.53-8.52 (d, 1H), 9.07 (s, 1H).

Example 31

Synthesis of 4-({[3-isopropyl-6-(2-methylimidazolyl)-4-hydroimidazo[1,2-a]pyrazin-8-yl]amino}methyl)benzamide Step 1

Into a 50-mL 3-necked round-bottom flask purged and maintained with an inert atmosphere of nitrogen, was placed 1H-1,3-benzodiazole (1 g, 6.20 mmol, 1.00 equiv), N,N-dimethylformamide (10 mL), and sodium hydride (223 mg, 9.29 mmol, 1.10 equiv). The resulting solution was stirred for 1 h at room temperature, then tert-butyl N-(2-bromoethyl)carbamate (3.8 g, 16.96 mmol, 2.00 equiv) was added. After stirring for 12 h at room temperature, the reaction was quenched with water/ice. The resulting solution was

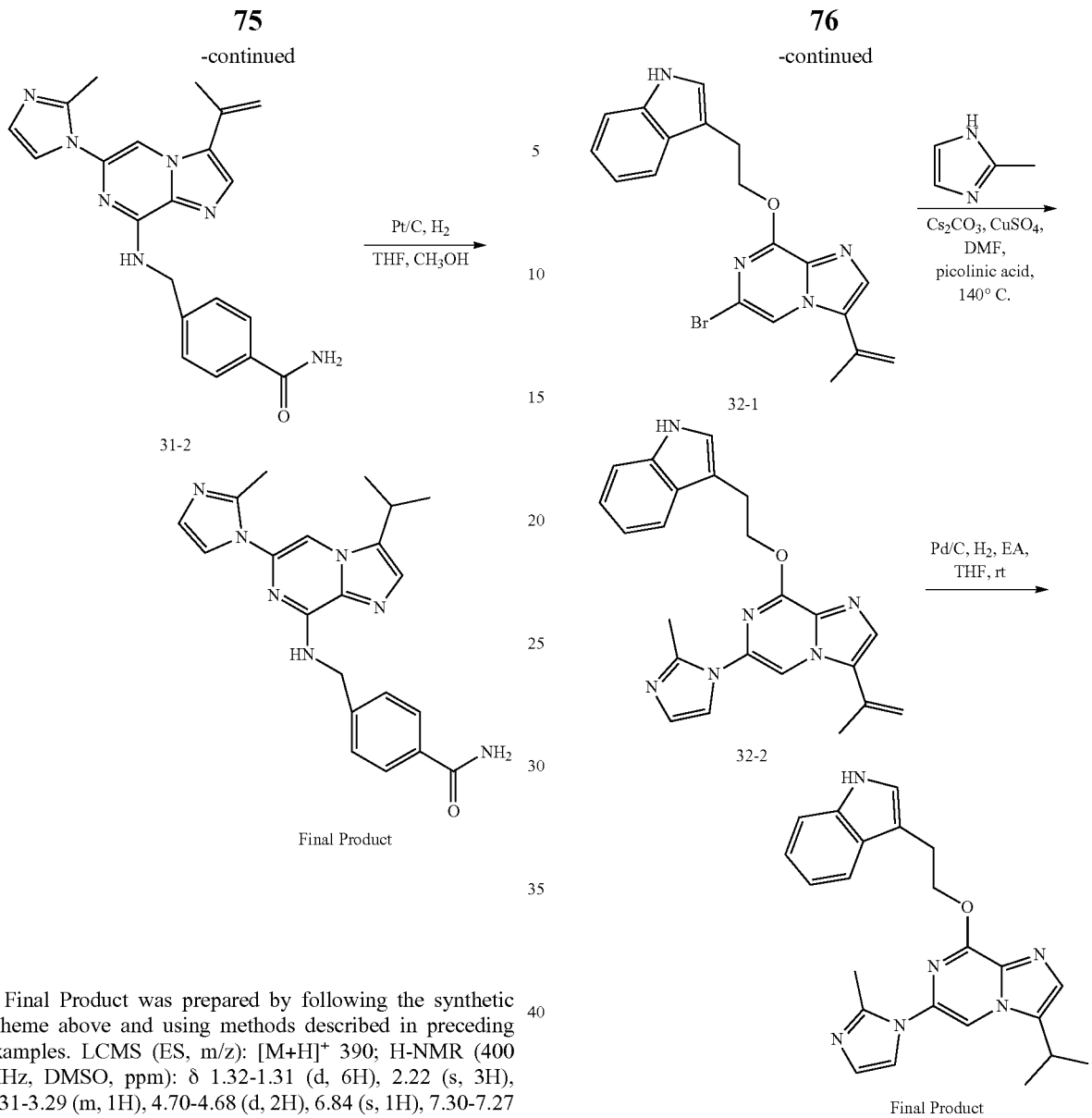

Final Product was prepared by following the synthetic scheme above and using methods described in preceding examples. LCMS (ES, m/z): [M+H]$^+$ 390; H-NMR (400 MHz, DMSO, ppm): δ 1.32-1.31 (d, 6H), 2.22 (s, 3H), 3.31-3.29 (m, 1H), 4.70-4.68 (d, 2H), 6.84 (s, 1H), 7.30-7.27 (m, 2H), 7.43-7.39 (m, 3H), 7.81-7.79 (d, 2H), 7.88 (s, 2H), 8.57-8.53 (t, 1H).

Example 32

Synthesis of 8-(2-indol-3-ylethoxy)-3-(methylethyl)-6-(2-methylimidazolyl)-4-hydroimidazo[1,2-a]pyrazine

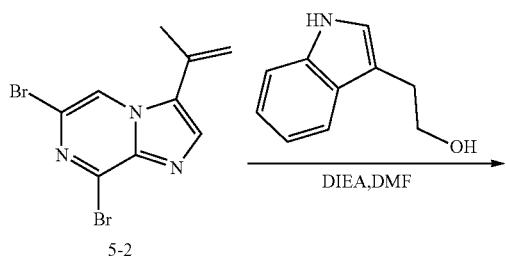

Step 1

To a stirred mixture of 6,8-dibromo-3-(prop-1-en-2-yl) imidazo[1,2-a]pyrazine (850 mg, 2.68 mmol, 1 equiv) and 2-(1H-indol-3-yl)ethanol (432.3 mg, 2.68 mmol, 1 equiv) in DMF (10 mL) was added DIEA (693.1 mg, 5.36 mmol, 2 equiv). The resulting mixture was stirred for overnight at room temperature. The resulting mixture was diluted with water (30 mL). The resulting mixture was extracted with EA (2×30 mL). The combined organic layers were concentrated under reduced pressure. Purification by Prep-TLC (PE/EA=2:1) provided 32-1 (60 mg, 5.63%) as a white solid.

Step 2

Into an 8 mL vial were added 32-1 (60 mg, 0.15 mmol, 1 equiv), 2-methyl-1H-imidazole (24.8 mg, 0.30 mmol, 2 equiv), Cs$_2$CO$_3$ (147.6 mg, 0.45 mmol, 3 equiv), CuSO$_4$ (72.3 mg, 0.45 mmol, 3 equiv), DMF (2 mL), picolinic acid (55.7 mg, 0.45 mmol, 3 equiv). The resulting mixture was stirred for 6 h at 140° C. The resulting mixture was diluted with water (10 mL). The resulting mixture was extracted with EA (2×10 mL). The combined organic layer was concentrated under reduced pressure. Purification by Prep-TLC (CH$_2$Cl$_2$/MeOH=20:1) provided 32-2 (35 mg, 58.16%) as a white solid.

Step 3

To a stirred solution of 32-2 (35 mg, 0.09 mmol, 1 equiv) in THF (2.5 mL) and EA (2.5 mL) were added Pd/C (7 mg). The reaction mixture was stirred for 4 h at room temperature under an atmosphere of hydrogen. The resulting mixture was filtered. The filtrate was concentrated under reduced pressure. Purification by Prep-TLC (CH$_2$Cl$_2$/MeOH=20:1) provided the Final Product (11.7 mg, 33.26%) as a white solid. LC-MS (ES, m/z): [M+H]$^+$401; H-NMR (400 MHz, DMSO, ppm): δ 1.32-1.34 (d, 6H), 2.43 (s, 3H), 3.24-3.28 (t, 2H), 3.35-3.40 (m, 1H), 4.71-4.75 (t, 2H), 6.91-6.97 (m, 2H), 7.05-7.09 (m, 1H), 7.26-7.27 (d, 1H), 7.33-7.35 (d, 1H), 7.44 (s, 1H), 7.57 (s, 1H), 7.61-7.63 (d, 1H), 8.39 (s, 1H), 10.87 (s, 1H).

BIOLOGICAL EXAMPLE

HEPG2 and HEPA1C1C7 cells were maintained in MEM and αMEM without nucleosides supplemented with 10% heat inactivated FBS respectively. Stably integrated DRE-luciferase cell lines were generated by transducing the both cell lines with Cignal XRE luciferase reporter (Qiagen) lentiviral particles according to the manufacturer protocol. For both cell lines stably integrated reporter cell lines were selected for the presence of 2 μg/mL puromycin. Following selection of stably integrated cell line pools, clonal cell lines were isolated by limiting dilution in 96-well plates. Transcriptional assays were performed by seeding 100 μL of cells at a density of 250,000 or 100,000 cells/mL, for HEPG2 and HEPA1C1C7 DRE-Luc cells respectively, into 96-well cell culture plates in OptiMEM supplemented with 0.5% heat inactivated FBS and allowed to attach overnight. For antagonist assays, the compounds were added in a semi-log dose response using a D300e Digital Dispenser (Tecan) followed normalization with vehicle (DMSO). Immediately following compound addition 104 of 2,3,7,8-Tetrachlorodibenzo-p-dioxin (TCDD) was added to the cells to a final concentration of 3 nM or 0.3 nM for the HEPG2 and HEPA1C1C7 DRE-Luc cells respectively. Following 24 h incubation the medium was removed and the cells were lysed in 25 μL of Reporter Lysis Buffer (Promega). Firefly luciferase activity was measured immediately following the addition of 50 μL Luciferase Assay Reagent (Promega). The percent maximal activity for each point was determined using the following equation: 100−(RLU$_{sample}$−RLU$_{vehicle-TCDD}$)/(RLU$_{vehicle+TCDD}$ RLU$_{vehicle-TCDD}$)*100. The relative IC50, defined as the compound concentration required to reduce the TCDD induced response between the top and bottom plateau of each individual dose response curve by half, for each compound was determined using Prism 7 (GraphPad Software).

TABLE 1

| Example | IC50 hAhR (antagonist mode) | HEPG2 % Max Inhibition |
|---|---|---|
| 1 | ++ | 100 |
| 2 | ++++ | 100 |
| 3 | ++++ | 100 |
| 4 | ++++ | 100 |
| 5 | ++ | 65 |
| 6 | +++ | 100 |
| 7 | ++++ | 100 |
| 8 | ++++ | 100 |

TABLE 1-continued

| Example | IC50 hAhR (antagonist mode) | HEPG2 % Max Inhibition |
|---|---|---|
| 9 | +++ | 100 |
| 10 | + | 47 |
| 11 | ++++ | 100 |
| 12 | ++++ | 100 |
| 13 | | 99 |
| 14 | ++++ | 100 |
| 15 | + | 73 |
| 16 | + | 83 |
| 17b | + | 81.3 |
| 17a | ++ | 100 |
| 18 | + | 77 |
| 19 | ++++ | 100 |
| 20 | ++++ | 100 |
| 21 | ++++ | 100 |
| 22 | ++++ | 100 |
| 23 | + | 12 |
| 24 | ++++ | 100 |
| 25 | ++++ | 100 |
| 26 | +++ | 98 |
| 27 | +++ | 100 |
| 28 | ++ | 33 |
| 29 | ++ | 100 |
| 30 | + | 94 |
| 31 | + | 31 |
| 32 | +++ | 100 |

(+) IC50 = 10 uM-1 uM
(++) IC50 = 1 uM-500 nM
(+++) IC50 = 500 nM-200 nM
(++++) IC50 < 200 nM

What is claimed is:

1. A compound having formula Ib or formula Id:

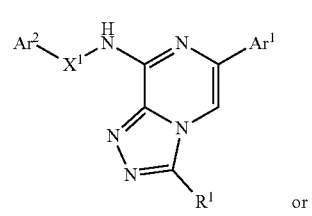

Ib

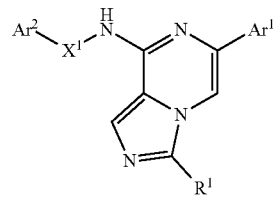

Id

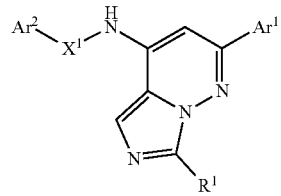

Ij or a pharmaceutically acceptable salt thereof,
wherein:
X$^1$ is C$_{1-6}$ alkylene;
Ar$^1$ is a 5- to 9-membered heteroaryl, wherein the 5- to 9-membered heteroaryl contains at least one N heteroatom, and further wherein the 5- to 9-membered heteroaryl is substituted with 0, 1, 2, or 3 substituents independently selected from the group consisting of deuterium, halogen, CN, $C_{1-4}$ alkyl, $C_{1-4}$ deuteroalkyl, $C_{1-4}$ haloalkyl, $C(O)R^a$, $C(O)NR^aR^b$, $C(O)OR^a$, $NR^aR^b$, $NR^bC(O)R^a$, $NR^aC(O)NR^aR^b$, $NR^bC(O)OR^c$, $OR^a$, $OC(O)R^a$, $OC(O)NR^aR^b$, $S(O)_{0-2}R^a$, and $S(O)_2NR^aR^b$;

$Ar^2$ is phenyl or a 5- to 9-membered heteroaryl, wherein the phenyl is substituted with 0, 1, 2, or 3 substituents independently selected from the group consisting of deuterium, halogen, CN, $C_{1-4}$ alkyl, $C_{1-4}$ deuteroalkyl, $C_{1-4}$ haloalkyl, $C(O)R^c$, $C(O)NR^aR^b$, $C(O)OR^a$, $NR^aR^b$, $NR^bC(O)R^a$, $NR^aC(O)NR^aR^b$, $NR^bC(O)OR^c$, $OR^a$, $OC(O)R^a$, $OC(O)NR^aR^b$, $S(O)_{0-2}R^a$, and $S(O)_2NR^aR^b$, and further wherein the 5- to 9-membered heteroaryl is substituted with 0, 1, 2, or 3 substituents independently selected from the group consisting of deuterium, halogen, CN, $C_{1-4}$ alkyl, $C_{1-4}$ deuteroalkyl, $C_{1-4}$ haloalkyl, $C(O)R^c$, $C(O)NR^aR^b$, $C(O)OR^a$, $NR^aR^b$, $NR^bC(O)R^a$, $NR^aC(O)NR^aR^b$, $NR^bC(O)OR^c$, $OR^a$, $OC(O)R^a$, $OC(O)NR^aR^b$, $S(O)_{0-2}R^a$, and $S(O)_2NR^aR^b$;

$R^1$ is $C_{1-6}$ alkyl, $C_{1-6}$ haloalkyl, $C_{1-6}$ hydroxyalkyl, $C_{3-7}$ cycloalkyl, or $C_{3-7}$ heterocycloalkyl;

each $R^a$ is independently H, $C_{1-4}$ alkyl, or $C_{1-4}$ haloalkyl;
each $R^b$ is independently H, $C_{1-4}$ alkyl, or $C_{1-4}$ haloalkyl; or each $R^a$ and $R^b$, together with the N heteroatom to which they are attached, independently forms a 4- to 6-membered ring, wherein each 4- to 6-membered ring independently contains 0, 1, or 2 additional ring heteroatoms or ring heteroatomic groups independently selected from the group consisting of N, O, S, S(O), and $S(O)_2$; and each $R^c$ is independently $C_{1-4}$ alkyl or $C_{1-4}$ haloalkyl.

2. The compound of claim 1, or a pharmaceutically acceptable salt thereof, wherein $X^1$ is —$CH_2$—.

3. The compound of claim 1, or a pharmaceutically acceptable salt thereof, wherein $X^1$ is —$CH_2CH_2$—.

4. The compound of claim 1, or a pharmaceutically acceptable salt thereof, wherein $X^1$ is —$CH(CH_3)CH_2$—.

5. The compound of claim 1, or a pharmaceutically acceptable salt thereof, wherein $Ar^1$ is pyrazolyl, imidazolyl, 1,2,3-triazolyl, 1,2,4-triazolyl, tetrazolyl, pyridinyl, pyridazinyl, pyrimidinyl, or pyrazinyl, wherein the pyrazolyl, imidazolyl, 1,2,3-triazolyl, 1,2,4-triazolyl, tetrazolyl, pyridinyl, pyridazinyl, pyrimidinyl, or pyrazinyl is substituted with 0, 1, 2, or 3 substituents independently selected from the group consisting of deuterium, halogen, CN, $C_{1-4}$ alkyl, $C_{1-4}$ deuteroalkyl, $C_{1-4}$ haloalkyl, $C(O)R^a$, $C(O)NR^aR^b$, $C(O)OR^a$, $NR^aR^b$, $NR^bC(O)R^a$, $NR^aC(O)NR^aR^b$, $NR^bC(O)OR^c$, $OR^a$, $OC(O)R^a$, $OC(O)NR^aR^b$, $S(O)_{0-2}R^a$, and $S(O)_2NR^aR^b$.

6. The compound of claim 5, or a pharmaceutically acceptable salt thereof, wherein $Ar^1$ is:

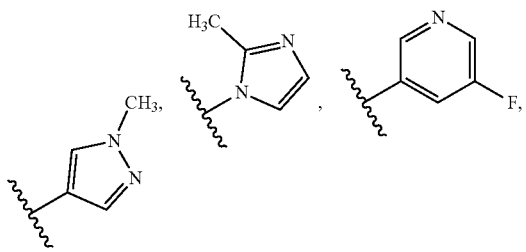

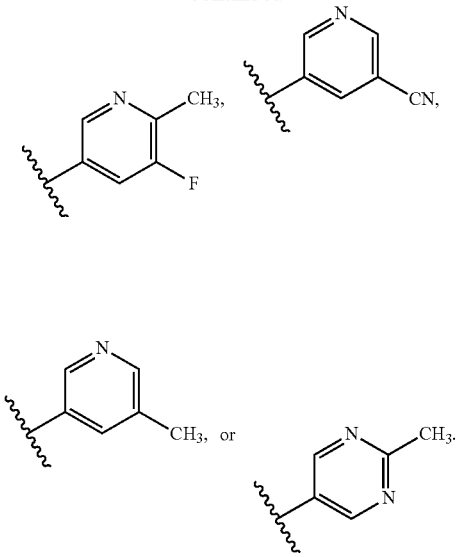

7. The compound of claim 1, or a pharmaceutically acceptable salt thereof, wherein $Ar^2$ is phenyl, wherein the phenyl is substituted with 0, 1, 2, or 3 substituents independently selected from the group consisting of deuterium, halogen, CN, $C_{1-4}$ alkyl, $C_{1-4}$ deuteroalkyl, $C_{1-4}$ haloalkyl, $C(O)R^c$, $C(O)NR^aR^b$, $C(O)OR^a$, $NR^aR^b$, $NR^bC(O)R^a$, $NR^aC(O)NR^aR^b$, $NR^bC(O)OR^c$, $OR^a$, $OC(O)R^a$, $OC(O)NR^aR^b$, $S(O)_{0-2}R^a$, and $S(O)_2NR^aR^b$.

8. The compound of claim 7, or a pharmaceutically acceptable salt thereof, wherein the phenyl is substituted with 0, 1, 2, or 3 substituents independently selected from the group consisting of $C_{1-4}$ alkyl, $C(O)NR^aR^b$, $C(O)OR^a$, $NR^aR^b$, $NR^bC(O)R^a$, $NR^bC(O)OR^c$, $OR^a$, $OC(O)R^a$, and $OC(O)NR^aR^b$.

9. The compound of claim 7, or a pharmaceutically acceptable salt thereof, wherein the phenyl is substituted with 0, 1, 2, or 3 substituents independently selected from the group consisting of $C(O)NH_2$ and OH.

10. The compound of claim 1, or a pharmaceutically acceptable salt thereof, wherein $Ar^2$ is a 5- to 9-membered heteroaryl, wherein the 5- to 9-membered heteroaryl is substituted with 0, 1, 2, or 3 substituents independently selected from the group consisting of deuterium, halogen, CN, $C_{1-4}$ alkyl, $C_{1-4}$ deuteroalkyl, $C_{1-4}$ haloalkyl, $C(O)R^c$, $C(O)NR^aR^b$, $C(O)OR^a$, $NR^aR^b$, $NR^bC(O)R^a$, $NR^aC(O)NR^aR^b$, $NR^bC(O)OR^c$, $OR^a$, $OC(O)R^a$, $OC(O)NR^aR^b$, $S(O)_{0-2}R^a$, and $S(O)_2NR^aR^b$.

11. The compound of claim 10, or a pharmaceutically acceptable salt thereof, wherein $Ar^2$ is pyrrolyl, indolyl, benzopyrazolyl, benzimidazolyl, 1H-pyrrolo[2,3-b]pyridinyl, or 1H-pyrrolo[3,2-b]pyridinyl, wherein the pyrrolyl, indolyl, benzopyrazolyl, benzimidazolyl, 1H-pyrrolo[2,3-b]pyridinyl, or 1H-pyrrolo[3,2-b]pyridinyl is substituted with 0, 1, 2, or 3 substituents independently selected from the group consisting of deuterium, halogen, CN, $C_{1-4}$ alkyl, $C_{1-4}$ deuteroalkyl, $C_{1-4}$ haloalkyl, $C(O)R^c$, $C(O)NR^aR^b$, $C(O)OR^a$, $NR^aR^b$, $NR^bC(O)R^a$, $NR^aC(O)NR^aR^b$, $NR^bC(O)OR^c$, $OR^a$, $OC(O)R^a$, $OC(O)NR^aR^b$, $S(O)_{0-2}R^a$, and $S(O)_2NR^aR^b$.

12. The compound of claim 10, or a pharmaceutically acceptable salt thereof, wherein $Ar^2$ is:

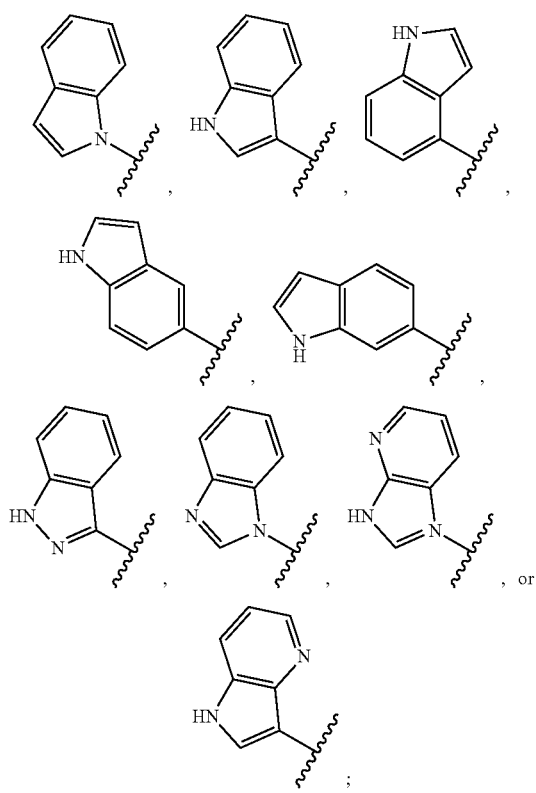

wherein each is substituted with 0, 1, 2, or 3 substituents independently selected from the group consisting of halogen, CN, $C_{1-4}$ alkyl, $C_{1-4}$ haloalkyl, $C(O)R^c$, $C(O)NR^aR^b$, $C(O)OR^a$, $OR^a$, and $OC(O)NR^aR^b$.

13. The compound of claim 10, or a pharmaceutically acceptable salt thereof, wherein $Ar^2$ is pyrrolyl, wherein the pyrrolyl is substituted with 0, 1, 2, or 3 substituents independently selected from the group consisting of halogen, CN, $C_{1-4}$ alkyl, $C_{1-4}$ haloalkyl, $C(O)R^c$, $C(O)NR^aR^b$, $C(O)OR^a$, $OR^a$, and $OC(O)NR^aR^b$.

14. The compound of claim 1, or a pharmaceutically acceptable salt thereof, wherein $R^1$ is $CH(CH_3)_2$ or $CH_3CHCH_2OH$.

15. The compound of claim 1, or a pharmaceutically acceptable salt thereof, wherein $R^1$ is $CH(CH_3)_2$.

16. The compound of claim 1, wherein the compound is selected from the group consisting of:

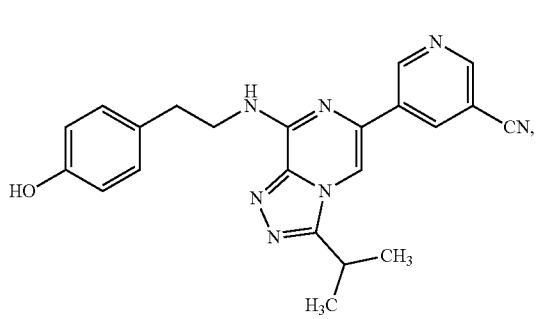

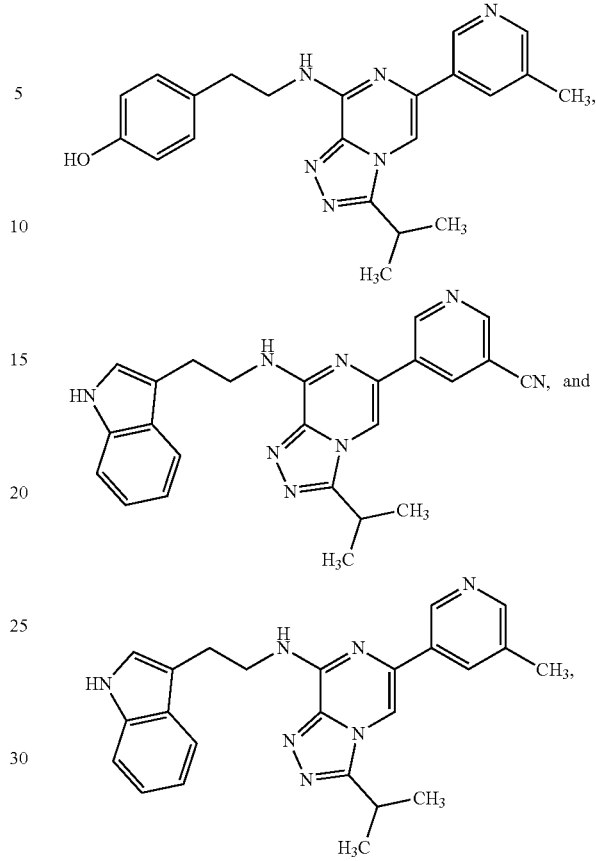

or a pharmaceutically acceptable salt thereof.

17. The compound of claim 1, wherein the compound is selected from the group consisting of:

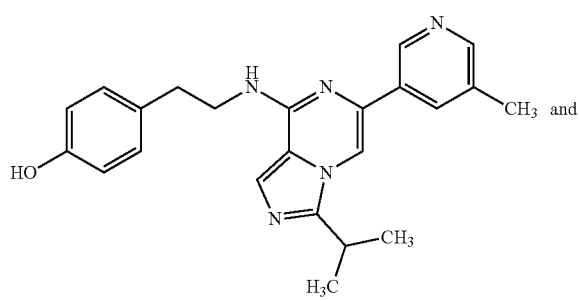

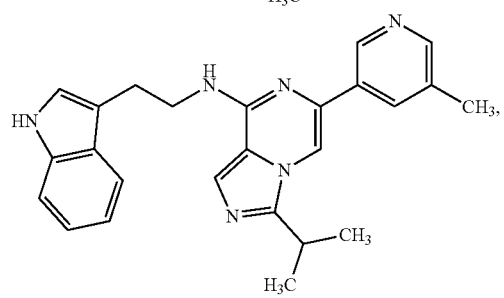

or a pharmaceutically acceptable salt thereof.

18. A pharmaceutical composition comprising a pharmaceutically acceptable excipient and a compound of claim 1, or a pharmaceutically acceptable salt thereof.

19. A method for modulating aryl hydrocarbon receptor activity in a subject in need thereof, wherein the method comprises administering to the subject an effective amount of a compound of claim 1, or a pharmaceutically acceptable salt thereof.

20. The method of claim 19, wherein the subject has cancer.

21. The method of claim 20, wherein the compound of claim 1, or a pharmaceutically acceptable salt thereof, is administered in combination with at least one additional anticancer therapy.

* * * * *